United States Patent
Chang et al.

(10) Patent No.: US 12,202,825 B2
(45) Date of Patent: Jan. 21, 2025

(54) PYRIMIDINE COMPOUNDS AND USE THEREOF

(71) Applicants: National Health Research Institutes, Miaoli County (TW); National Cheng Kung University, Tainan (TW)

(72) Inventors: Jang-Yang Chang, Taipei (TW); Meng-Ru Shen, Tainan (TW); Kak-Shan Shia, Taipei (TW); Chien-Huang Wu, New Taipei (TW)

(73) Assignees: National Health Research Institutes, Miaoli County (TW); National Cheng Kung University, Tainan (TW)

( * ) Notice: Subject to any disclaimer, the term of this patent is extended or adjusted under 35 U.S.C. 154(b) by 66 days.

(21) Appl. No.: 17/877,163

(22) Filed: Jul. 29, 2022

(65) Prior Publication Data

US 2023/0085362 A1  Mar. 16, 2023

Related U.S. Application Data

(60) Provisional application No. 63/228,586, filed on Aug. 2, 2021.

(51) Int. Cl.
| C07D 413/14 | (2006.01) |
| A61P 23/00 | (2006.01) |
| A61P 25/02 | (2006.01) |
| C07D 403/14 | (2006.01) |

(52) U.S. Cl.
CPC ............ *C07D 413/14* (2013.01); *A61P 25/02* (2018.01); *C07D 403/14* (2013.01)

(58) Field of Classification Search
CPC ...... C07D 403/14; C07D 413/14; A61P 23/00
See application file for complete search history.

(56) References Cited

U.S. PATENT DOCUMENTS

| 2006/0293324 A1 | 12/2006 | Yen et al. |
| 2016/0158231 A1 | 6/2016 | Jarpe et al. |

FOREIGN PATENT DOCUMENTS

| WO | WO-2021/178485 A1 | 9/2021 |

OTHER PUBLICATIONS

Chen et al "Discovery of Potential Neuroprotective Agents Against Paclitaxel-Induced Peripheral Neuropathy" Journal of Medicinal Chemistry vol. 65, pp. 4767-4782, Mar. 2, 2022.
Pubchem "SID 437065006" Nov. 23, 2020.

*Primary Examiner* — Yong S. Chong
(74) *Attorney, Agent, or Firm* — Morse, Barnes-Brown & Pendleton, P.C.; Martin Z. Zhang, Esq.

(57) ABSTRACT

Pyrimidine compounds of formula (I) shown herein. Also disclosed are pharmaceutical compositions containing one of the pyrimidine compounds and methods of using the pyrimidine compounds to treat or prevent chemotherapy-induced peripheral neuropathy.

20 Claims, No Drawings

PYRIMIDINE COMPOUNDS AND USE THEREOF

CROSS-REFERENCE TO RELATED APPLICATIONS

This application claims the benefit of priority based on U.S. Provisional Application No. 63/228,586, filed Aug. 2, 2021, the entire content and disclosure of which is incorporated herein by reference in its entirety.

BACKGROUND

Chemotherapy-induced peripheral neuropathy ("CIPN") is an adverse effect of certain anticancer drugs.

Affecting 30-70% of patients receiving chemotherapy, CIPN is one of the main reasons for dose reduction or early discontinuation in life-saving cancer treatments. Its symptoms include sensory disturbances (e.g., an increased sensitivity to pain), which leads to poor quality of life for years.

No drug has been approved for treating or preventing CIPN by the US Food and Drug Administration. Further, recent clinical trials are not promising. See Poupon et al., "Minimizing chemotherapy-induced peripheral neuropathy: Preclinical and clinical development of new perspectives", *Expert Opin. Drug Saf.* (2015) 14(8).

There is a need to develop a method of treating and preventing CIPN.

SUMMARY

The present invention is based on an unexpected discovery that certain pyrimidine compounds are effective in treating and preventing CIPN.

In one aspect, this invention relates to the pyrimidine compounds of formula (I):

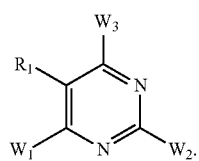

In this formula, each of $R_1$, $W_1$, $W_2$, and $W_3$ are defined below.

$R_1$ is H, halo, nitro (i.e., —$NO_2$), cyano (—CN), amino, $C_{1-6}$ alkyl, $C_{1-6}$ alkoxy, $C_{3-10}$ cycloalkyl, $C_{1-10}$ hetero-cycloalkyl, aryl, or heteroaryl.

$W_1$ is $C_{1-10}$ heterocycloalkyl or NH—$CH_2$—Ar1-$(CH_2)_m$-A1.

One of $W_2$ and $W_3$ is $NR_aR_b$, and the other of $W_2$ and $W_3$ is NH—$CH_2$—Ar2 $(CH_2)_n$-A2.

In which, each of Ar1 and Ar2, independently, is five-membered heteroaryl;

each of A1 and A2, independently, is H, OH, SH, $CO_2R_c$, $PO_3R_cR_d$, $NH_2$, benzylamino, isopropylamino, ethanolamino, carbamido (i.e., —$NHCONH_2$), guanidinyl (i.e., —$NHC(NH)NH_2$), $C_{1-6}$ alkoxy, $C_{3-10}$ cycloalkyl, $C_{3-10}$ cycloalkyloxy, $C_{1-10}$ heterocycloalkyl, $C_{1-10}$ heterocycloalkyloxy, aryl, aryloxy, heteroaryl, heteroaryloxy, or $NCOR_c$;

each of $R_a$ and $R_b$, independently, is H, $C_{1-6}$ alkyl, $C_{3-10}$ cycloalkyl, $C_{1-10}$ hetero-cycloalkyl, or $R_a$ and $R_b$, together with the nitrogen atom to which they are bonded, are $C_{1-10}$ heterocycloalkyl;

each of $R_c$ and $R_d$, independently, is H, $C_{1-6}$ alkyl, $C_{3-10}$ cycloalkyl, $C_{1-10}$ hetero-cycloalkyl, aryl, or heteroaryl;

each of $C_{1-6}$ alkyl, $C_{1-6}$ alkoxy, $C_{3-10}$ cycloalkyl, $C_{3-10}$ cycloalkyloxy, $C_{1-10}$ hetero-cycloalkyl, $C_{1-10}$ heterocycloalkyloxy, aryl, heteroaryl, aryloxy, heteroaryloxy, ethanolamino, benzylamino, and carbamido is optionally substituted with hydroxyl, halo, nitro, cyano, amino, $C_{1-6}$ alkyl, arylalkyl, $C_{1-6}$ alkoxyl, $C_{1-6}$ carboxyalkyl, aryl, heteroaryl, $PO_3R_eR_f$, $NCOR_e$, $NC(O)OR_e$, $C(O)OR_e$, $COR_e$, $(CH_2)_x$—$PO_3R_eR_f$, $(CH_2)_x$—$NCOR_e$, or $(CH_2)_x$—$C(O)OR_e$;

each of $R_e$ and $R_f$, independently, is H, $C_{1-6}$ alkyl, $C_{3-10}$ cycloalkyl, $C_{1-10}$ hetero-cycloalkyl, aryl, or heteroaryl;

each of m and n, independently, is 0, 1, 2, 3, 4, or 5; and x is 1, 2, 3, or 4.

Preferred features include $R_1$ being H, $W_1$ being morpholino, $W_2$ being NH $CH_2$—Ar2-$(CH_2)_n$-A2, and $W_3$ being $NR_aR_b$. Typically, each of A1 and A2, independently, is H, OH, $C_{1-6}$ alkyl, $C_{1-6}$ alkoxy, or $NCOR_c$; $R_a$ is H or $R_a$ and $R_b$, together with the nitrogen atom to which they are bonded, are six-membered heterocycloalkyl; $R_b$ is six-membered heterocycloalkyl or $R_b$ and $R_a$, together with the nitrogen atom to which they are bonded, are six-membered heterocycloalkyl; $R_c$ is $C_{1-6}$ alkyl; each of $C_{1-6}$ alkyl, $C_{1-6}$ alkoxy, and $C_{1-10}$ hetero-cycloalkyl is optionally substituted with hydroxyl, $NH_2$, $(CH_2)_x$—$PO_3R_eR_f$, $C(O)OR_e$, or $(CH_2)_x$—$NCOR_e$; each of $R_e$ and $R_f$, independently, is H, $C_{1-6}$ alkyl, $C_{3-10}$ cycloalkyl, $C_{1-10}$ hetero-cycloalkyl, aryl, or heteroaryl; each of m and n, independently, is 2, 3, or 4; and x is 1, 2, 3, or 4.

Another aspect of this invention relates to a method of treating or preventing chemotherapy-induced peripheral neuropathy. The method includes administering to a subject in need thereof an effective amount of any one of the compounds described above. Optionally, the method includes a further step of administering to the subject an anticancer agent (e.g., paclitaxel), preferably after the administration of a compound of this invention.

Also within the scope of this invention is a pharmaceutical composition containing one of the above-described compounds and a pharmaceutically acceptable carrier.

The term "alkyl" herein refers to a straight or branched hydrocarbon group, containing 1-20 (e.g., 1-10 and 1-6) carbon atoms. Exemplary alkyl groups are methyl ("Me"), ethyl ("Et"), n-propyl, iso-propyl, n-butyl, iso-butyl, and tert-butyl. Alkyl includes its halo substituted derivatives, i.e., haloalkyl, which refers to alkyl substituted with one or more halogen (chloro, fluoro, bromo, or iodo) atoms. Examples include trifluoromethyl, bromomethyl, and 4,4,4-trifluorobutyl. The term "alkoxy" refers to an —O-alkyl group (e.g., methoxy, ethoxy, propoxy, and isopropoxy). Alkoxy includes haloalkoxy, namely, alkoxy substituted with one or more halogen atoms, e.g., —O—$CH_2Cl$ and —O—$CHClCH_2Cl$.

The term "cycloalkyl" refers to a saturated and partially unsaturated monocyclic, bicyclic, tricyclic, or tetracyclic hydrocarbon group having 3 to 12 carbons (e.g., $C_{3-10}$).

Examples are cyclopropyl, cyclobutyl, cyclopentyl, cyclopentenyl, cyclohexyl, cyclohexenyl, cycloheptyl, and cyclooctyl. The term "cycloalkyloxy" refers to an —O—cycloalkyl group, e.g., cyclohexyloxy. Cycloalkyloxy includes halocycloalkyloxy, referring to cycloalkyloxy substituted with one or more halogen atoms.

The term "heterocycloalkyl" refers to a nonaromatic 3-8 membered monocyclic, 8-12 membered bicyclic, or 11-14 membered tricyclic ring system having one or more heteroatoms (e.g., O, N, P, and S). Examples of heterocycloalkyl groups include piperazinyl, piperidinyl, imidazolidinyl, azepanyl, pyrrolidinyl, dihydrothiadiazolyl, dioxanyl, morpholinyl, thiomorpholinyl, 1,1-dioxide thiomorpholinyl, tetrahydropyranyl, and tetrahydrofuranyl. The term "heterocycloalkyloxy" refers to an —O-heterocycloalkyl. Each of hetercycloalkyl and heterocycloalkyloxy include its halogenated versions, i.e., those having one or more substitutions of halogen atoms.

The term "aryl" refers to a 6-carbon monocyclic, 10-carbon bicyclic, 14-carbon tricyclic aromatic ring system wherein each ring can have 1 to 5 substituents. Examples include phenyl, naphthyl, and anthracenyl. The term "aralkyl" refers to alkyl substituted with an aryl group. The term "aryloxy" refers to an —O-aryl group, e.g., phenoxy.

The term "heteroaryl" refers to an aromatic 5-8 membered monocyclic, 8-12 membered bicyclic, or 11-14 membered tricyclic ring system having one or more heteroatoms (e.g., O, N, P, and S). Examples include triazolyl, oxazolyl, thiadiazolyl, tetrazolyl, oxazolyl, isoxazolyl, pyrazolyl, pyridyl, carbazolyl, furyl, imidazolyl, benzimidazolyl, pyrimidinyl, thienyl, quinolinyl, indolyl, thiazolyl, and benzothiazolyl. The term "heteroaryl alkyl" refers to an alkyl group substituted with a heteroaryl group. The term "heteroaryloxy" refers to an —O-heteroaryl group.

The terms "halo" refers to a fluoro, chloro, bromo, or iodo radical. The term "amino" refers to a radical derived from amine, which is unsubstituted or mono-/di-substituted with alkyl, aryl, cycloalkyl, heterocycloalkyl, or heteroaryl. The term "alkylamino" refers to alkyl-NH—. The term "dialkylamino" refers to alkyl-N(alkyl)-.

Alkyl, cycloalkyl, heterocycloalkyl, aryl, heteroaryl, aralkyl, heteroaralkyl, alkoxy, and aryloxy mentioned herein include both substituted and unsubstituted moieties. Examples of a substituent include halo, hydroxyl, amino, cyano, nitro, mercapto, alkoxycarbonyl, amido, carboxy, alkanesulfonyl, alkylcarbonyl, carbamido, carbamyl, carboxyl, thioureido, thiocyanato, sulfonamido, alkyl, alkenyl, alkynyl, alkyloxy, aryl, heteroaryl, cycloalkyl, and heterocycloalkyl, in which alkyl, alkenyl, alkynyl, alkyloxy, aryl, heteroaryl, cycloalkyl, and heterocycloalkyl may further substituted.

The term "compound", when referring to a compound of formula (I), also includes its salts, solvates, and prodrugs. A salt can be formed between an anion and a positively charged group (e.g., amino) on a compound. Examples of a suitable anion are chloride, bromide, iodide, sulfate, nitrate, phosphate, citrate, methanesulfonate, trifluoroacetate, acetate, malate, tosylate, tartrate, fumurate, glutamate, glucuronate, lactate, glutarate, and maleate. A salt can also be formed between a cation and a negatively charged group. Suitable cations include sodium ion, potassium ion, magnesium ion, calcium ion, and ammonium cation such as tetramethyl-ammonium ion. Further, a salt can contain quaternary nitrogen atoms. A solvate refers to a complex formed between an active compound and a pharmaceutically acceptable solvent. Examples of a pharmaceutically acceptable solvent include water, ethanol, isopropanol, ethyl acetate, acetic acid, and ethanolamine. A prodrug refers to a compound that, after administration, is metabolized into a pharmaceutically active drug. Examples of a prodrug include esters and other pharmaceutically acceptable derivatives.

The compounds may contain one or more non-aromatic double bonds or asymmetric centers. Each of them occurs as a racemate or a racemic mixture, a single R enantiomer, a single S enantiomer, an individual diastereomer, a diastereometric mixture, a cis-isomer, or a trans-isomer. Compounds of such isomeric forms are within the scope of this invention. They can be present as a mixture or can be isolated using chiral synthesis or chiral separation technologies.

This invention also features use of one or more of the above-described pyrimidine compounds of formula (I) for the manufacture of a medicament for treating and preventing CIPN.

The term "treating" or "treatment" refers to administering one or more of the pyrimidine compounds to a subject, who receives chemotherapy, or has a predisposition toward CIPN, with the purpose to confer a therapeutic effect, e.g., to cure, relieve, alter, affect, ameliorate, or prevent CIPN, its symptoms, or the predisposition toward it. "An effective amount" refers to the amount of a compound that is required to confer the therapeutic effect. Effective doses will vary, as recognized by those skilled in the art, depending on the types of symptoms treated, route of administration, excipient usage, and the possibility of co-usage with other therapeutic treatment.

To practice the method of the present invention, a composition having one or more of the above-described pyrimidine compounds can be administered parenterally, orally, nasally, rectally, topically, or buccally. The term "parenteral" as used herein refers to subcutaneous, intracutaneous, intravenous, intraperitoneal, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or di-glycerides).

Fatty acid, such as oleic acid and its glyceride derivatives, are useful in the preparation of injectables, as are natural pharmaceutically acceptable oils, such as olive oil and castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens and Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents.

A composition having one or more of the above-described pyrimidine compounds can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active compound. Examples include colloidal silicon oxide, magnesium stearate, cellulose, sodium lauryl sulfate, and D&C Yellow #10.

The details of one or more embodiments of the invention are set forth in the description below. Other features, objects, and advantages of the invention will be apparent from the description and from the claims.

DETAILED DESCRIPTION

The peripheral nervous system ("PNS") consists of sensory neurons and motor neurons. In chemotherapy, an anticancer drug can impair both sensory and motor neurons. CIPN Symptoms typically start in hands/feet and then arms/legs, spanning from tingling or numbness (e.g., paresthesia) to sharp, stabbing pain or burning sensitivity to temperature (e.g., dysesthesia, pain, thermal hypersensitivity, and thermal hyposensitivity). In certain cases, CIPN leads to hearing loss, blurred vision, change in taste, mechanical hypersensitivity, mechanical hyposensitivity, and autonomic disturbances.

As these symptoms are induced by an anticancer drug in chemotherapy, the type of the anticancer drug (e.g., paclitaxel, oxaliplatin platinum salts, *vinca* alkaloids, bortezomib, thalidomide, epothilones, and eribulin) and the cumulative dose may impact the incidence of one or more symptoms and the severity/grade of neuropathy. Further, treatments of different cancers (e.g., colorectal cancer, lung cancer, breast cancer, and prostate cancer) lead to different symptoms and severity, e.g., neuropathic pain.

Numerous anticancer drugs cause CIPN. Examples are epothilones (e.g., ixabepilone available as Ixempra® from Bristol-Myers Squibb, New York, New York), arsenic trioxide (Trisenox®, Teva Pharmaceuticals USA, Parsippany, New Jersey), cytarabine (Cytosar-U® and Depocyt®), etoposide, hexamethylmelamine, ifosfamide (Ifex®), methotrexate (Trexall®), procarbazine (Matulane®), and vinblastine. The chemotherapeutic drugs that most commonly elicit CIPN include platinum compounds (cisplatin, carboplatin, oxaliplatin), vincristine, taxanes (docetaxel, paclitaxel), bortezomib (Velcade®), thalidomide (Thalomid®), and lenalidomide.

A compound of formula (I) is suitable for treating or preventing one or more CIPN symptoms.

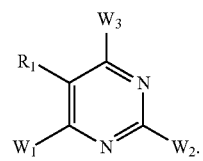

(I)

The compound can be used together with one of the above-mentioned anticancer drugs, preferably by administering the compound to a patient prior to the administration of the anticancer drug, e.g., at least 10 minutes (e.g., at least 30 minutes, at least 1 hour, and at least 2 hours) before the administration of the anticancer drug.

Referring to formula (I) above, preferred subsets of compounds having the features as described below.

In one subset of the compounds of formula (I), $W_1$ is $C_{1-10}$ (e.g., $C_{4-5}$) nitrogen containing heterocycloalkyl including (i) morpholino optionally substituted with one or more $C_{1-6}$ alkyl, e.g.,

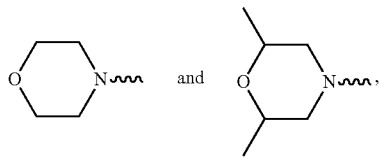

(ii) thiomorpholino or 1,1-dioxide thiomorpholino, e.g.,

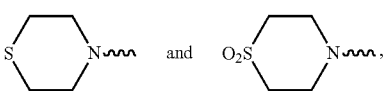

(iii) piperidino optionally substituted with one or more $C_{1-6}$ alkyl and halo, e.g.,

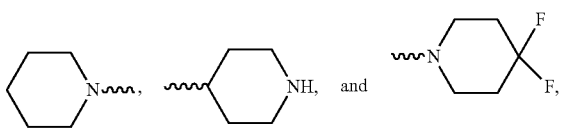

and (iv) piperazino optionally substituted with one or more $C_{1-6}$ alkyl such as

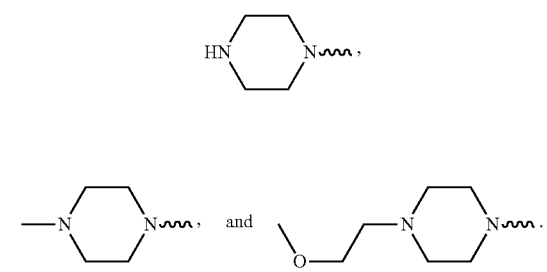

Alternatively $W_1$ is $NH-CH_2-Ar1-(CH_2)_m-A1$, e.g.,

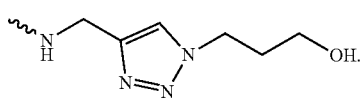

In another subset of the compounds, one of $W_2$ and $W_3$ is $NH-CH_2-Ar2-(CH_2)_n-A2$. Examples include:

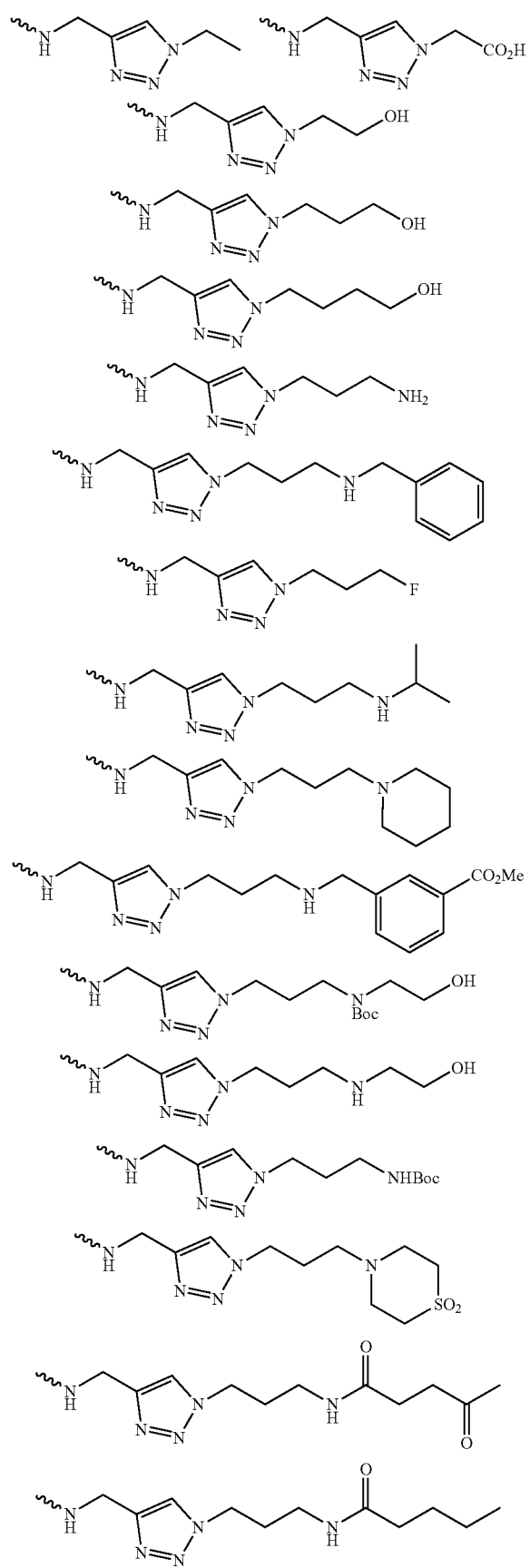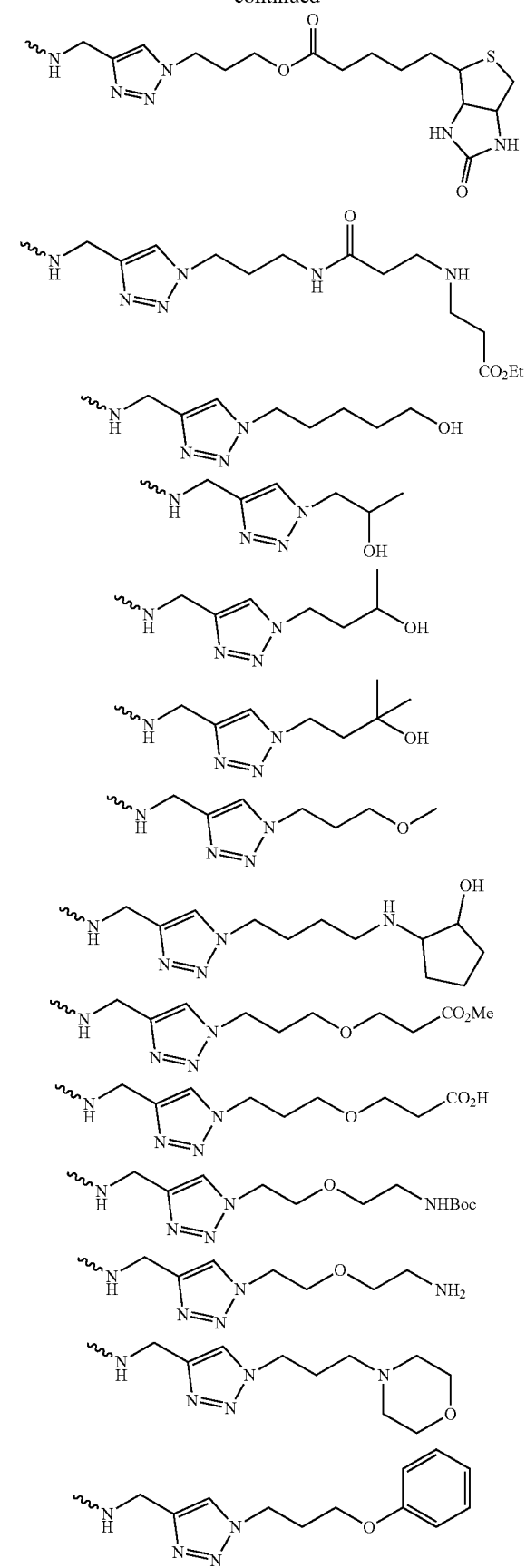

-continued
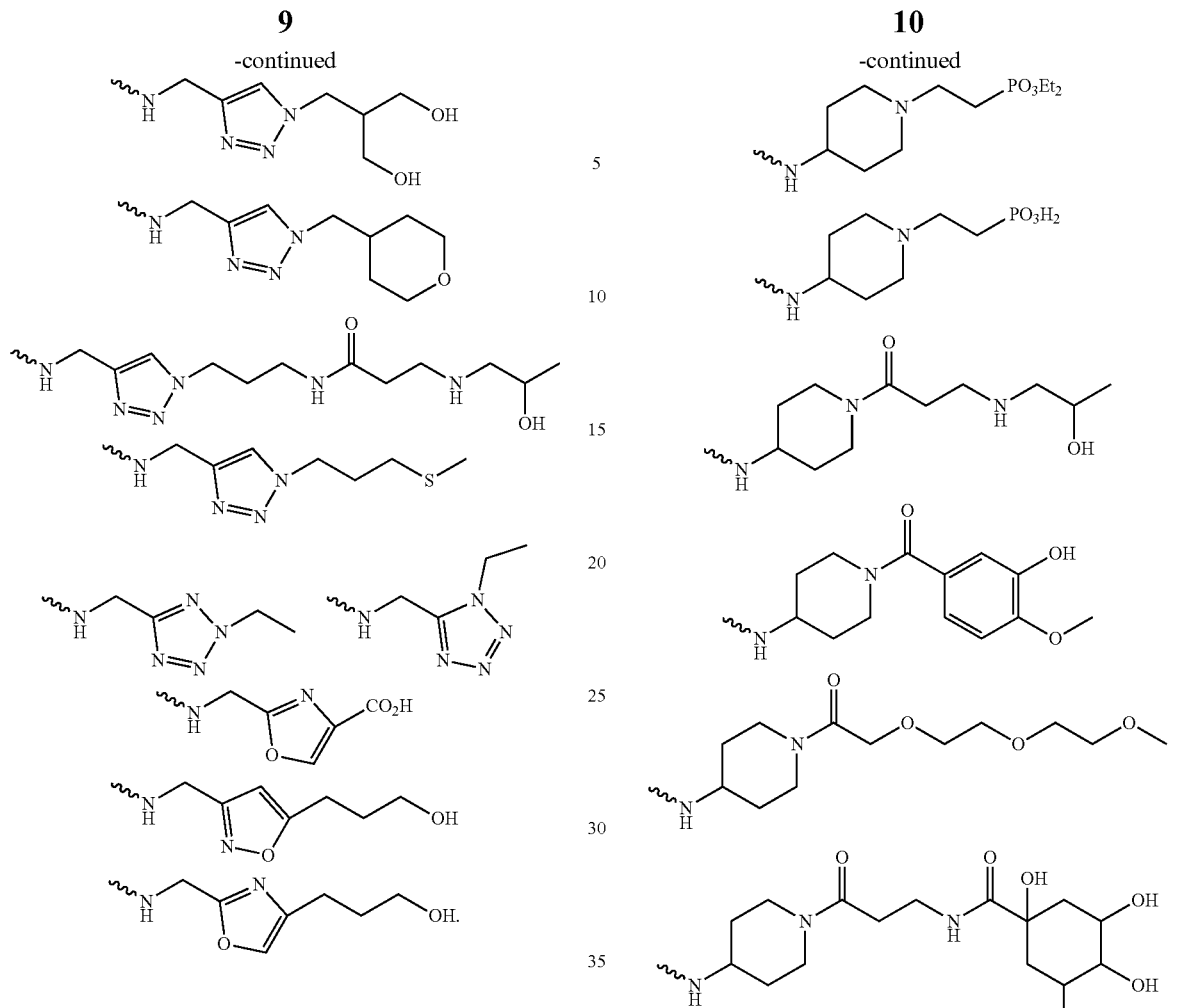
The other one of $W_2$ and $W_3$ is $NR_aR_b$. Examples include:
-continued
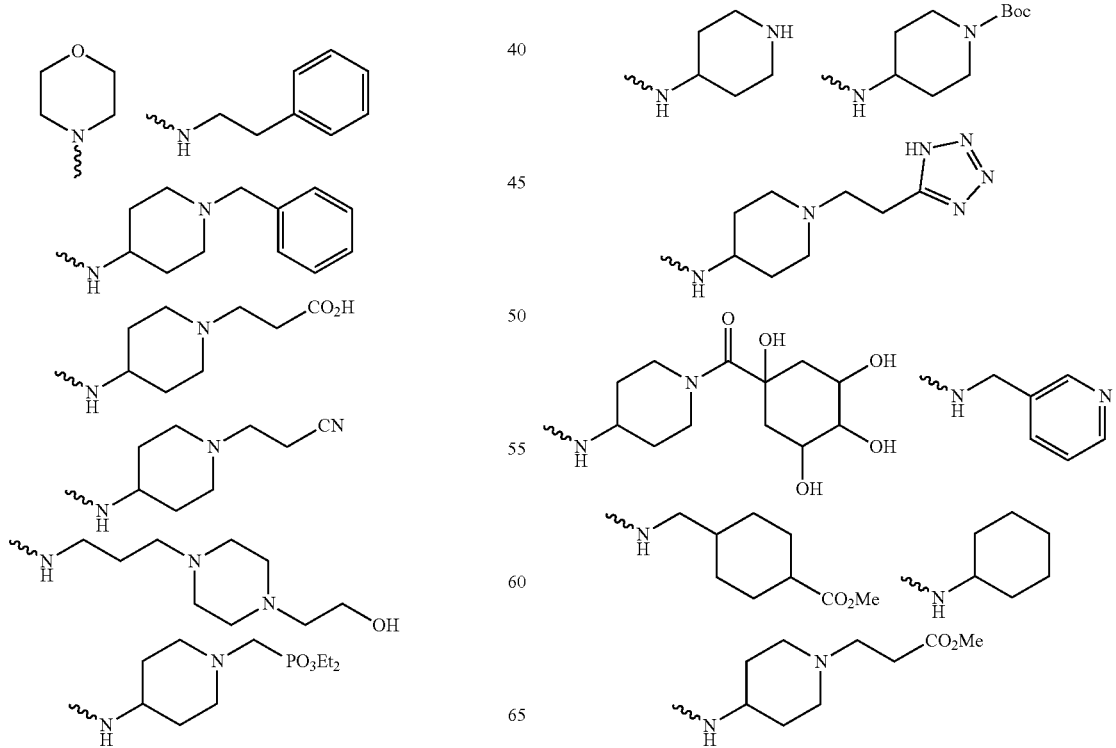

-continued
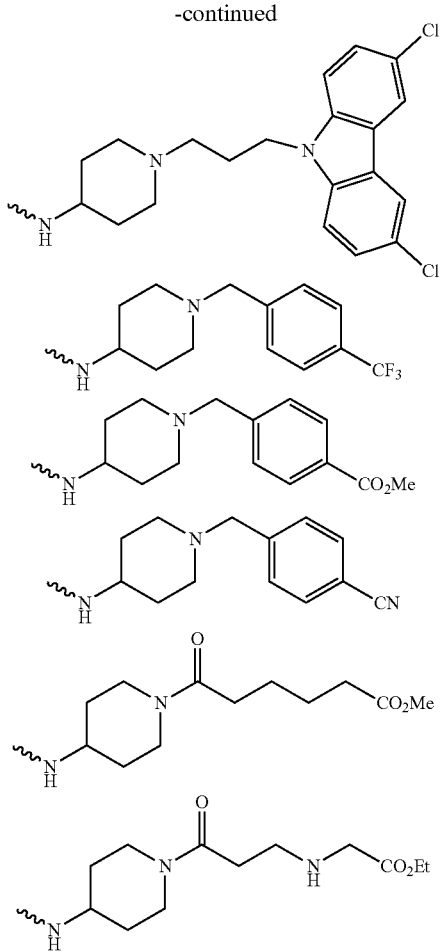
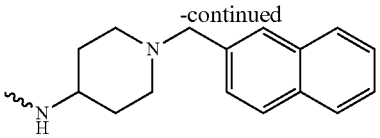
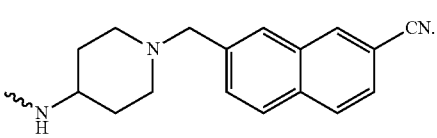
The compounds of formula (II) below are also a preferred subset of the compounds of formula (I).
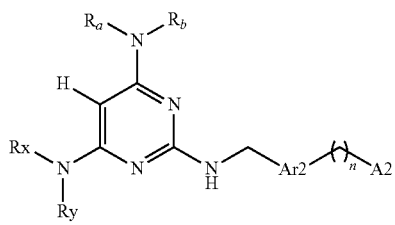
$R_a$, $R_b$, Ar2, A2 and n are defined above.
Rx and Ry, together with the nitrogen atom to which they are bonded, are a five to eight-membered hetercycloalkyl (e.g., morpholino, piperidino, and piperazino).
Provided below are Compounds 1-148 as exemplary compounds of formula (I):
1
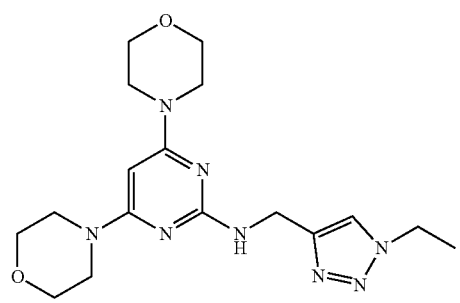
2
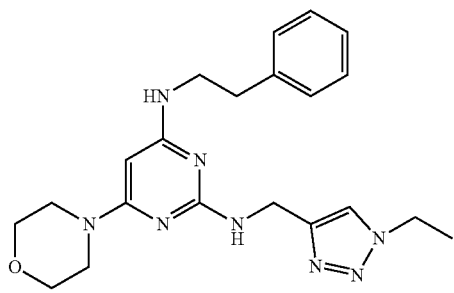
3
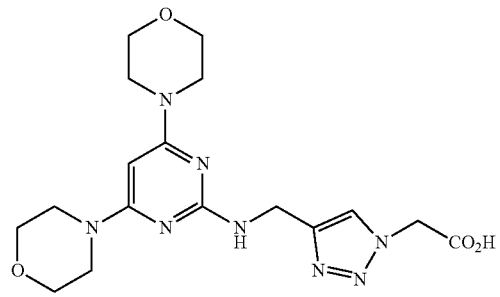
4
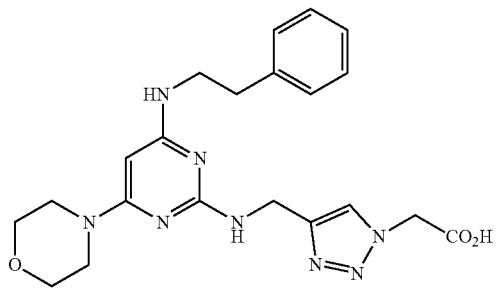

-continued
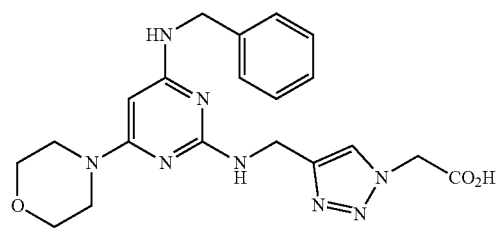
5
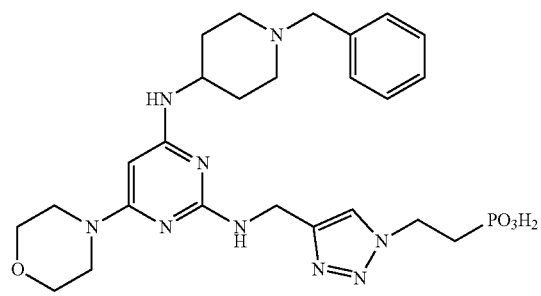
7
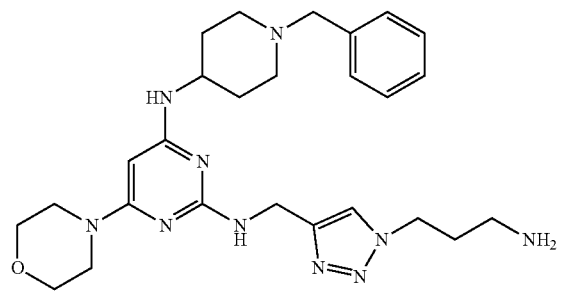
9
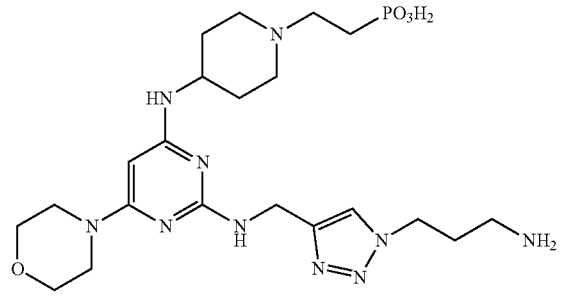
11
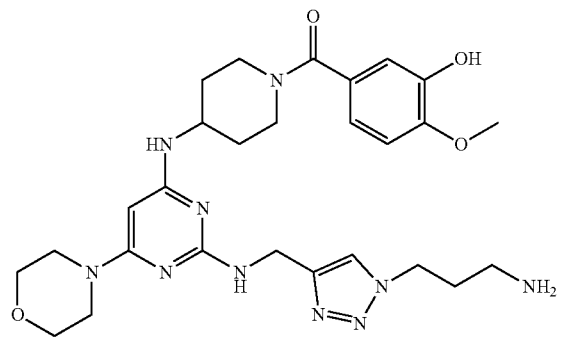
13
6
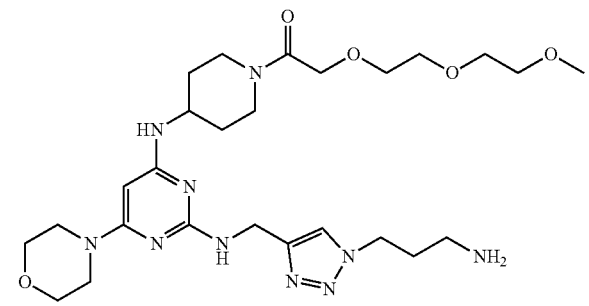

-continued
15
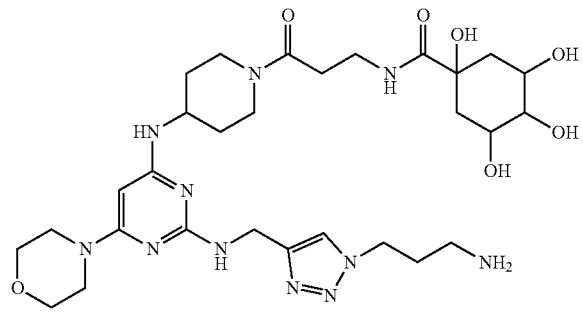
16
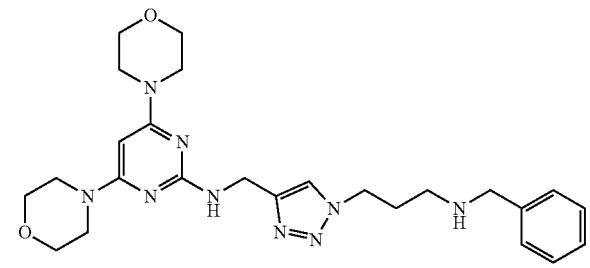
17
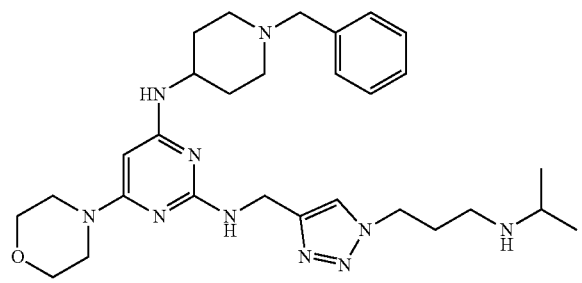
18
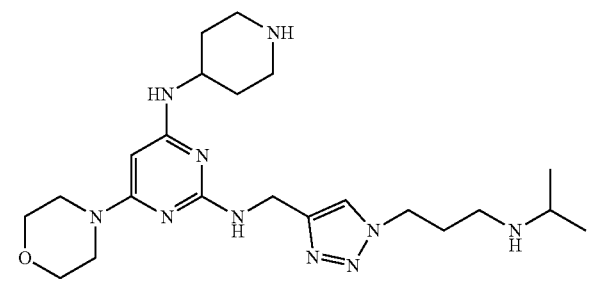
19
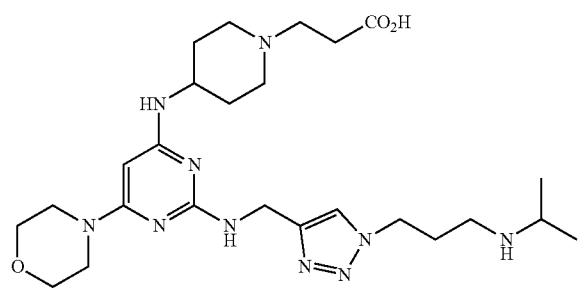
20
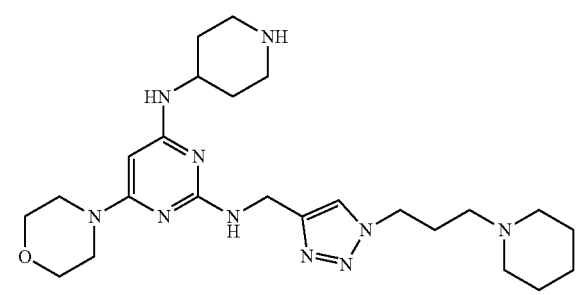
21
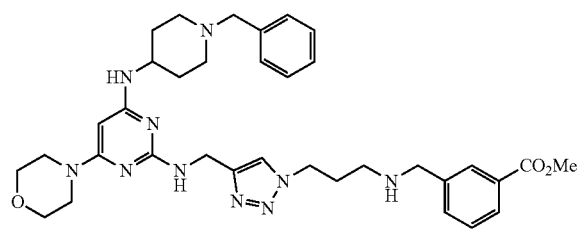
22
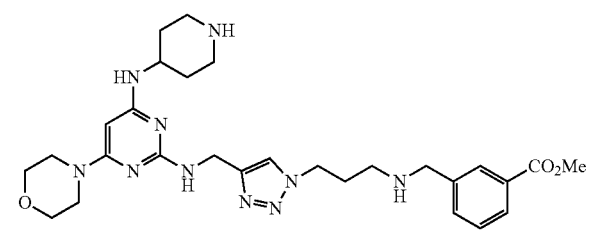
23
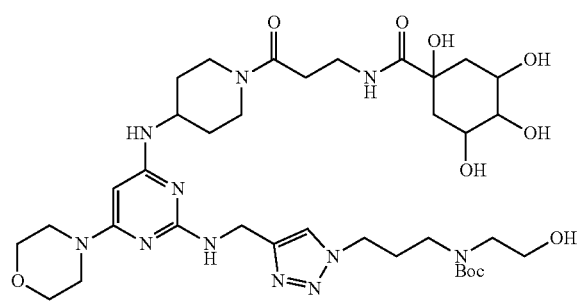
24
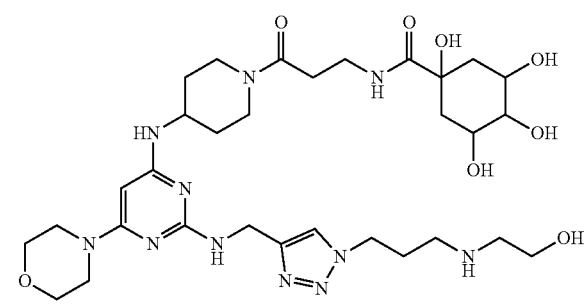

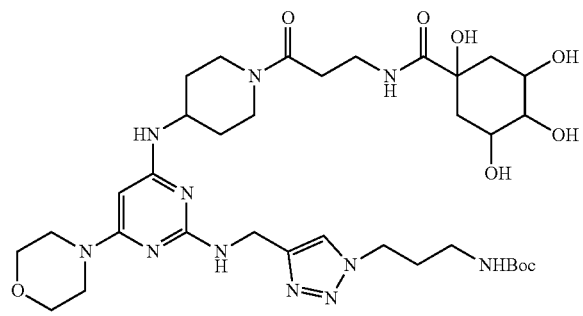
25
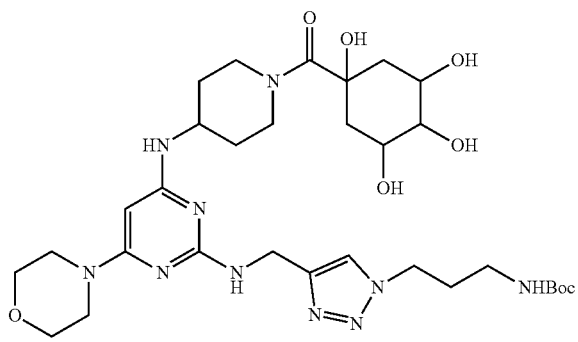
26
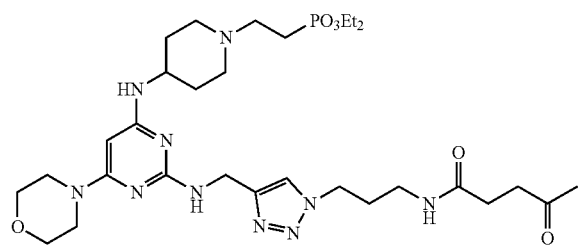
27
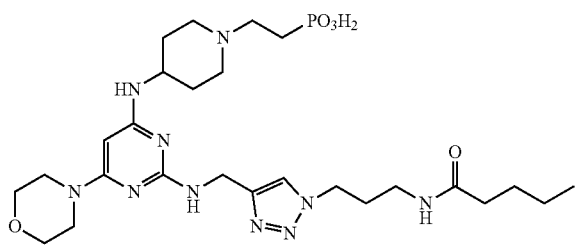
28
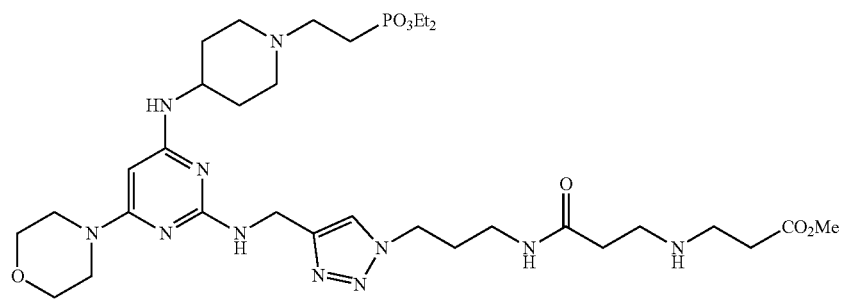
29
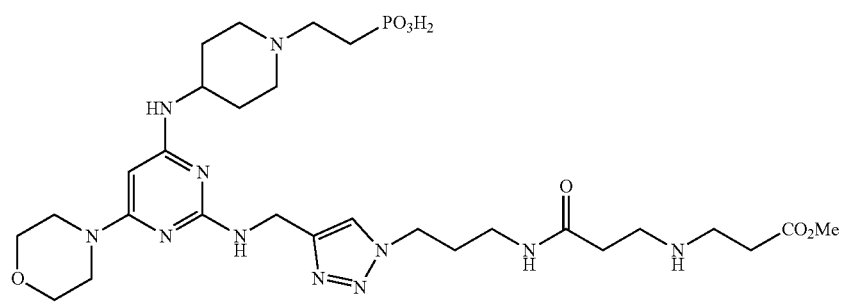
30
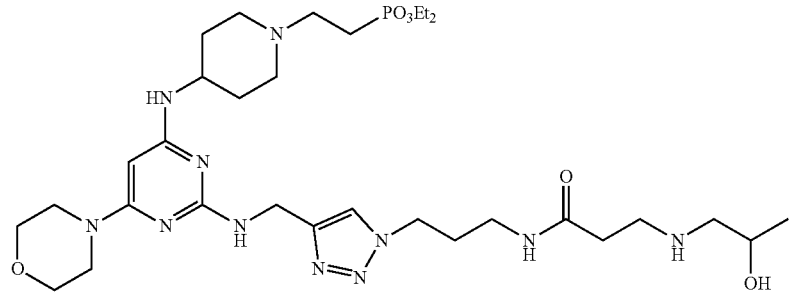
31

-continued
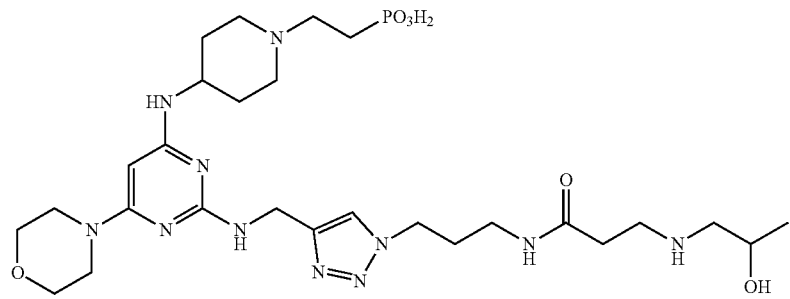
32
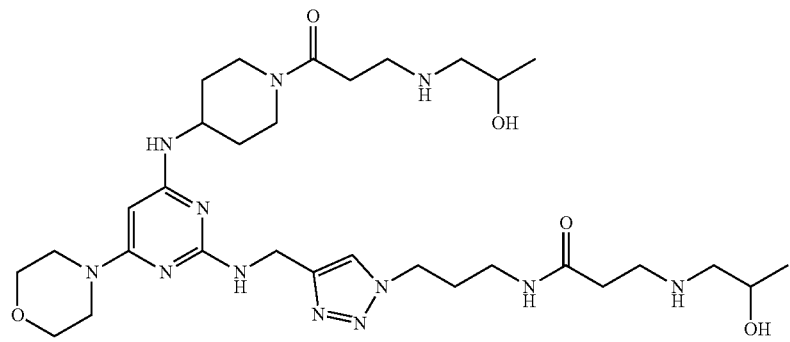
33
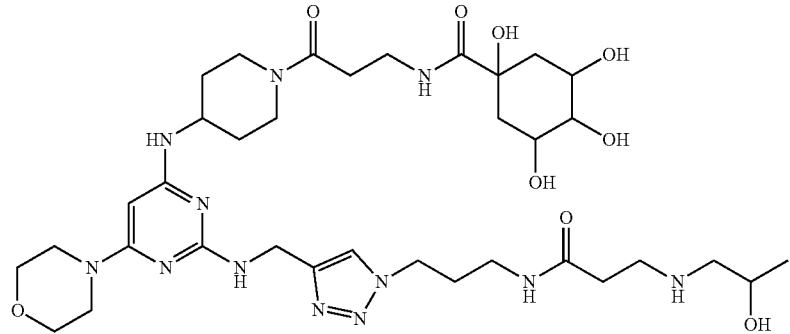
34
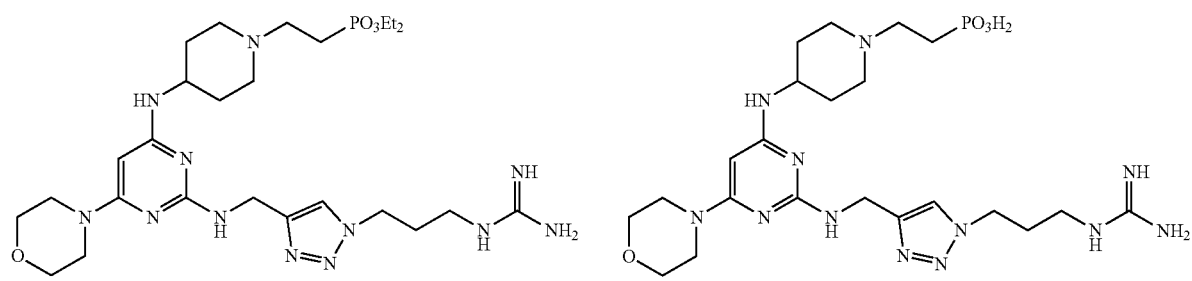
35  36
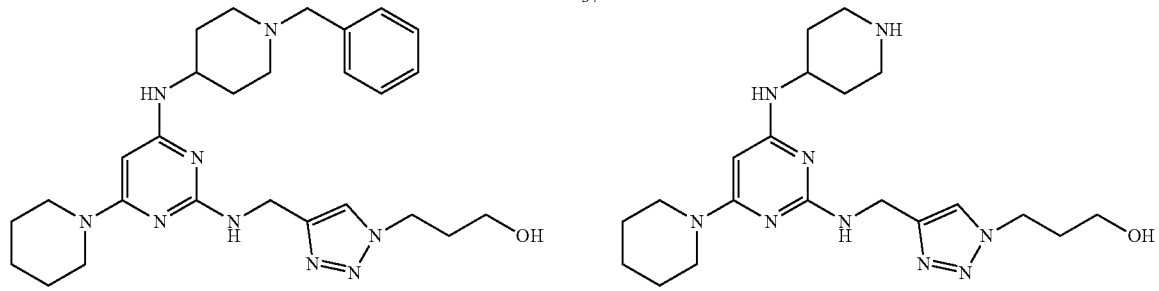
37  38

-continued
39
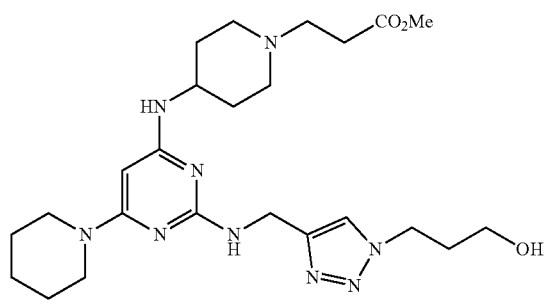
40
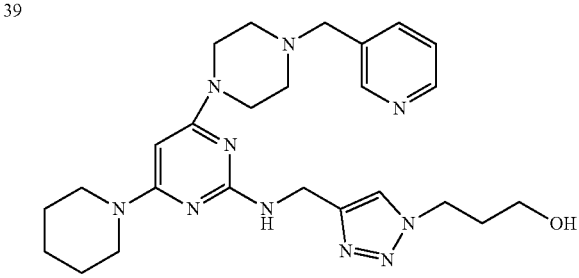
41
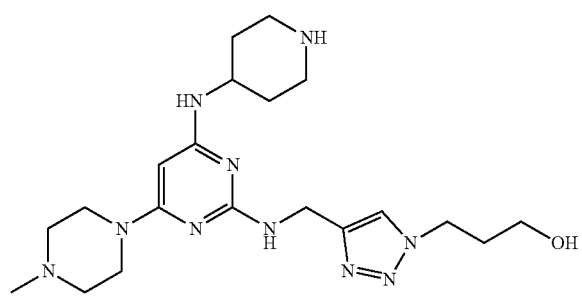
42
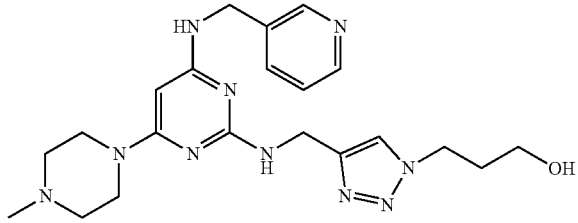
43
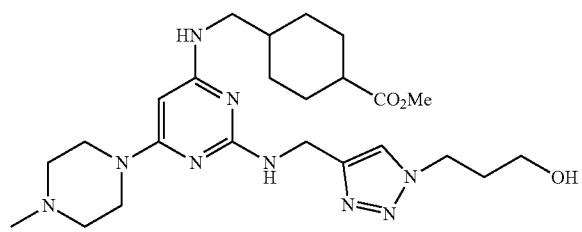
44
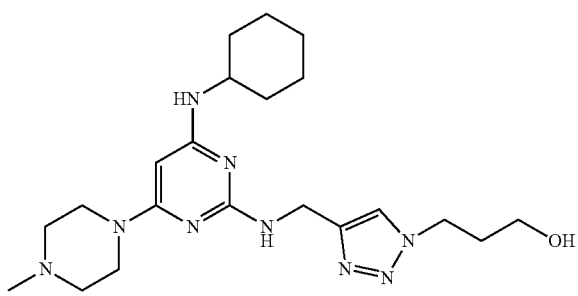
45
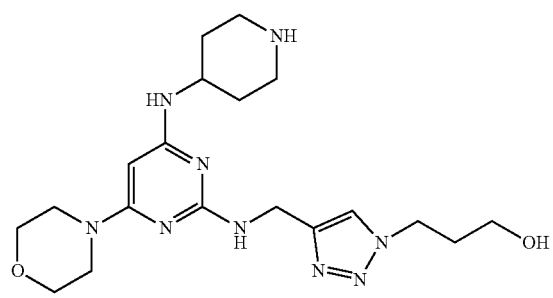
46
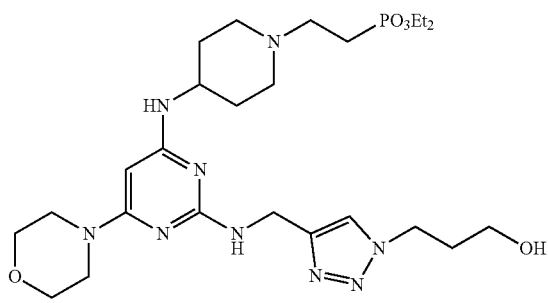
47
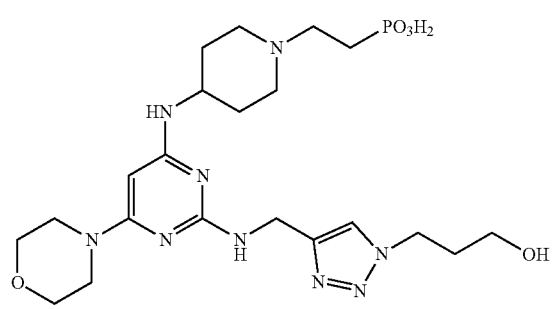
48
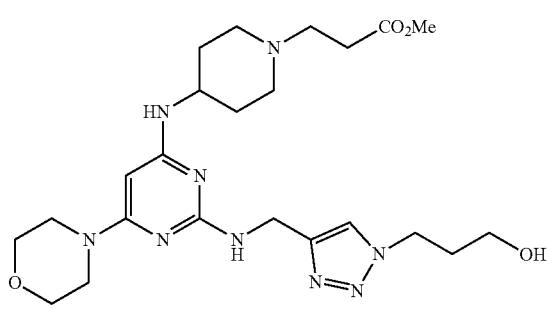

-continued
49
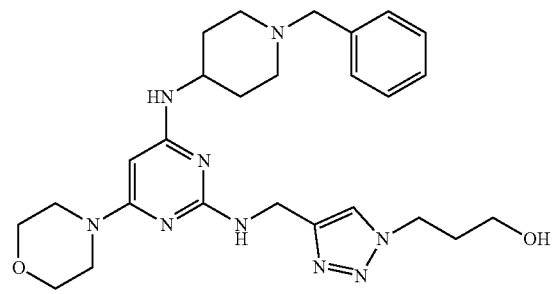
50
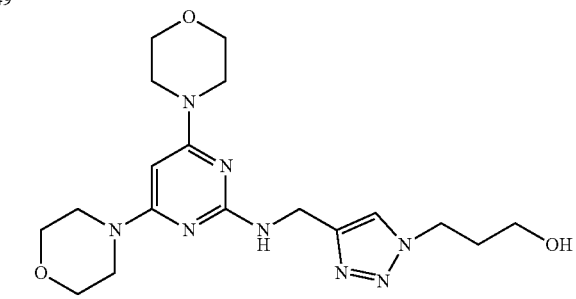
51
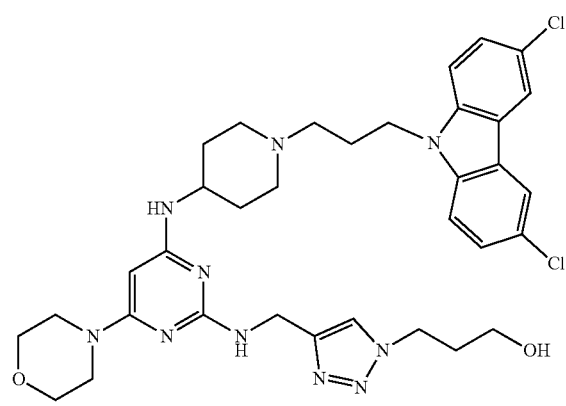
52
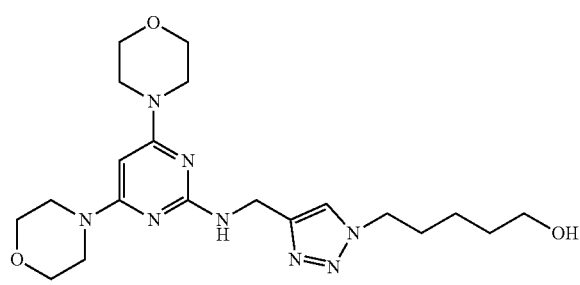
53
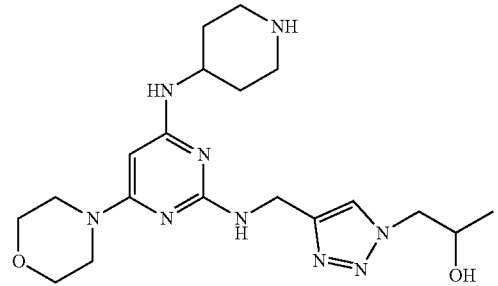
54
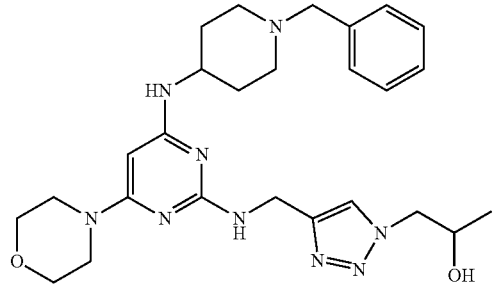
55
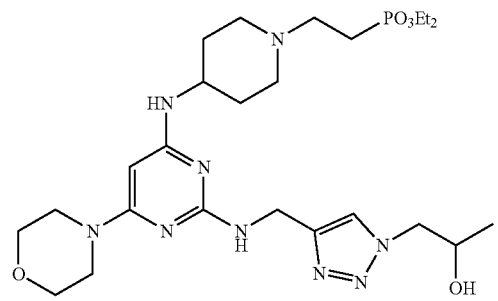
56
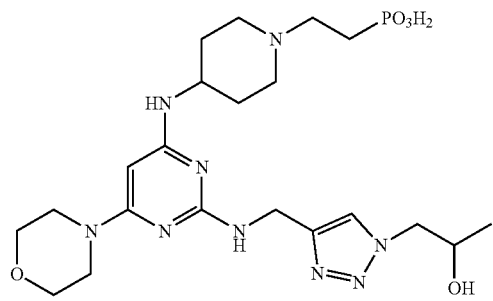
57
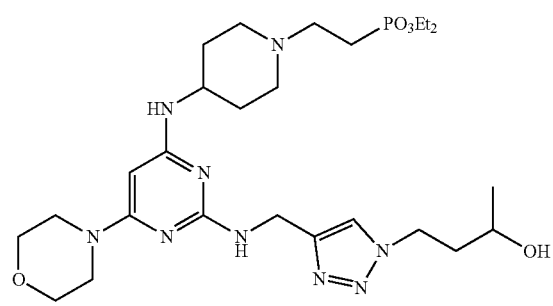
58
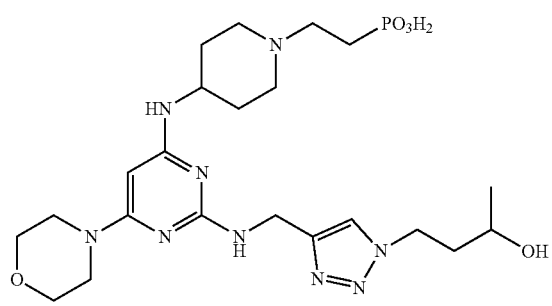

-continued
59
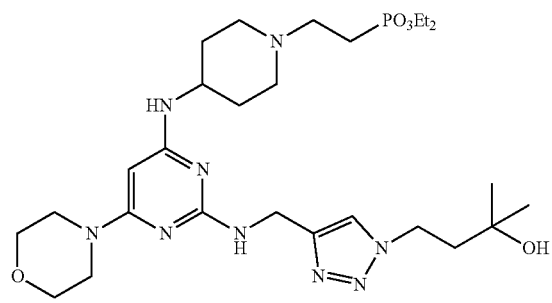
60
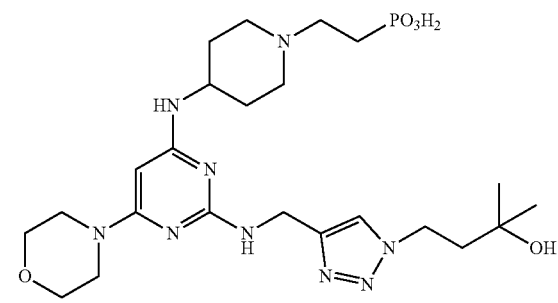
61
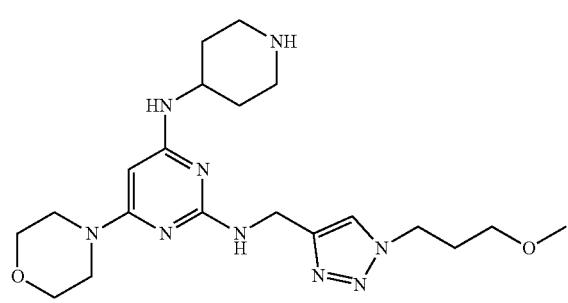
62
63
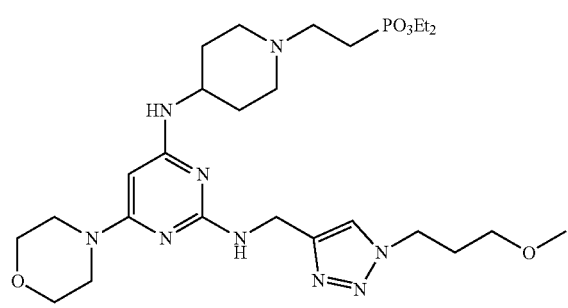
64
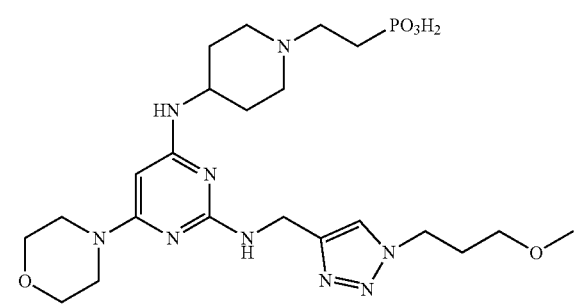
65
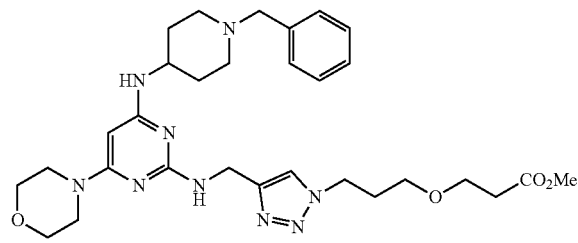
66
67
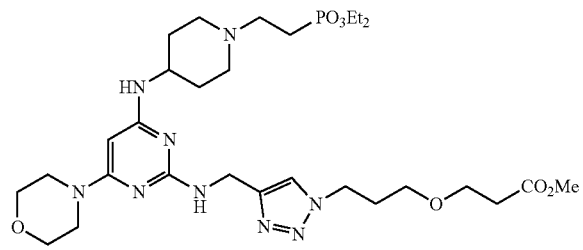
68
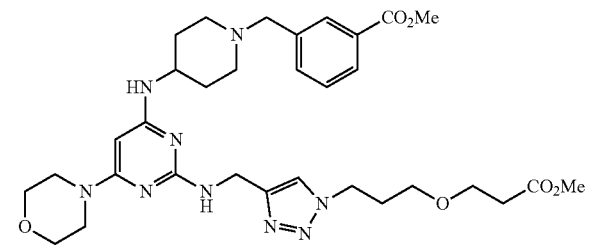

-continued
69
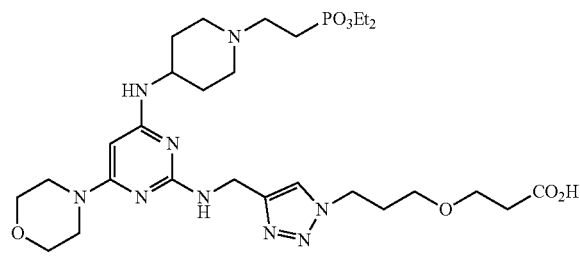
70
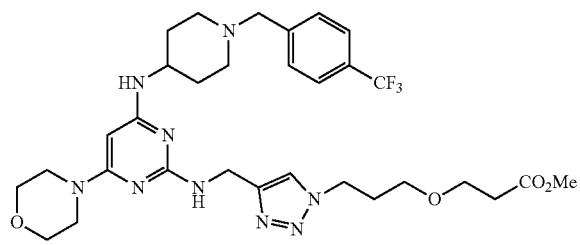
71
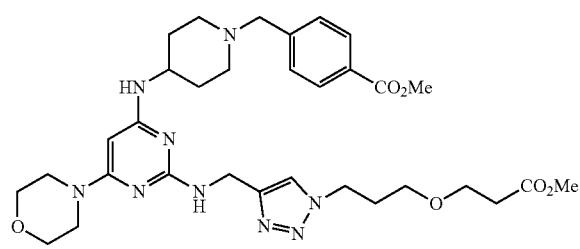
72
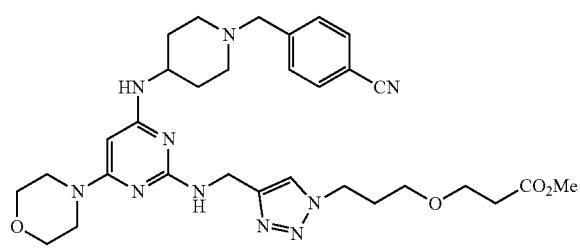
73
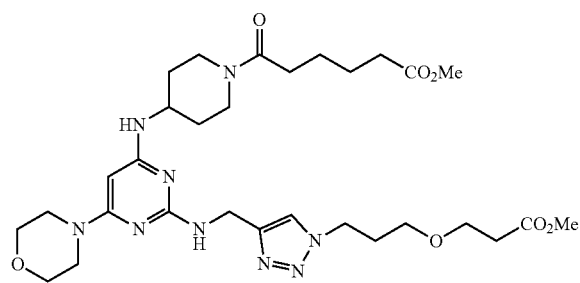
74
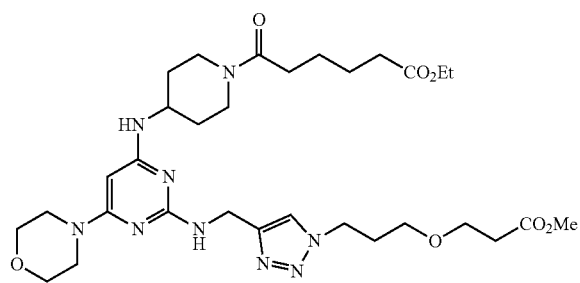
75
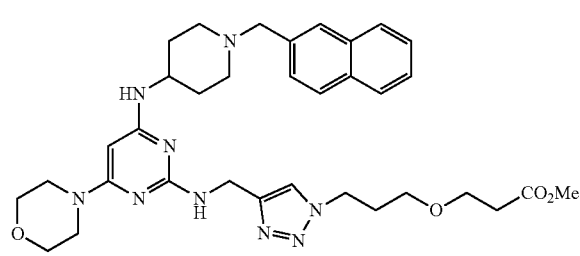
76
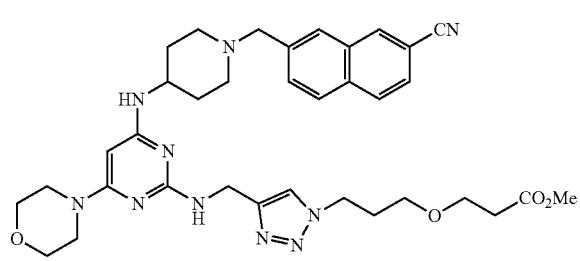
77
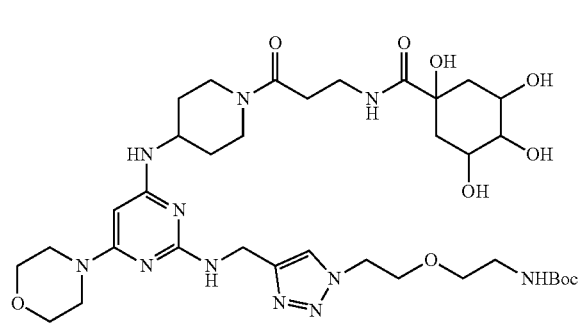
78
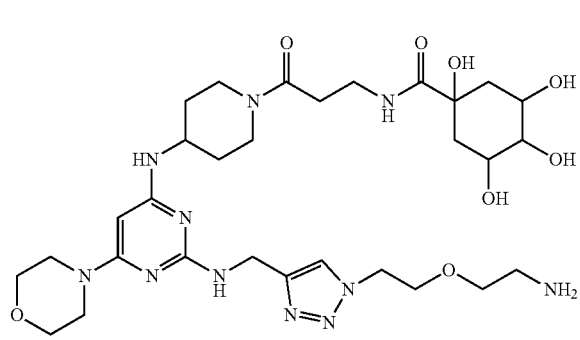

-continued
79
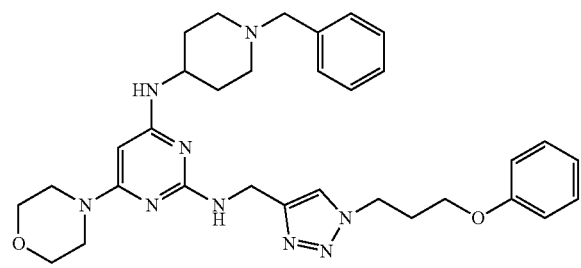
80
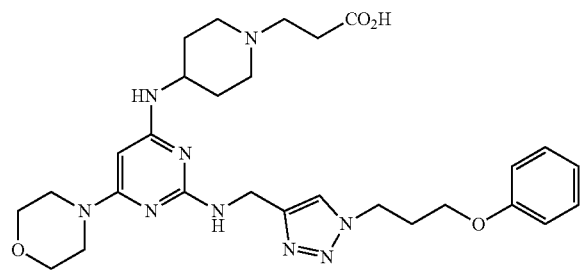
81
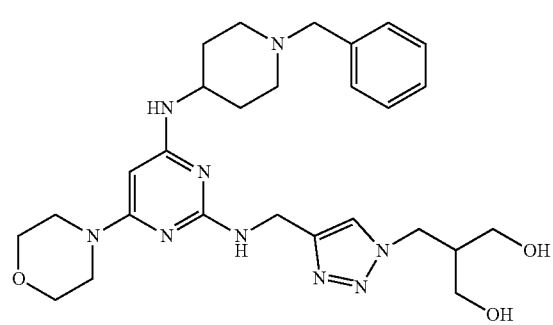
82
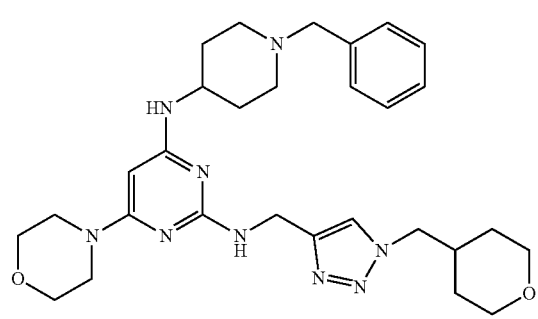
83
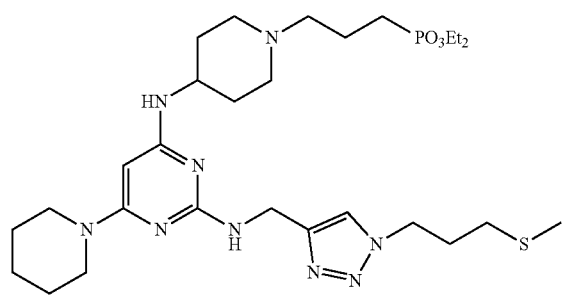
84
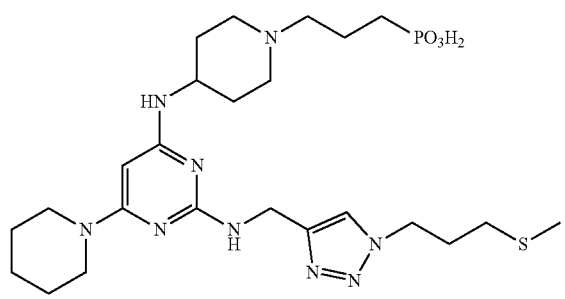
85
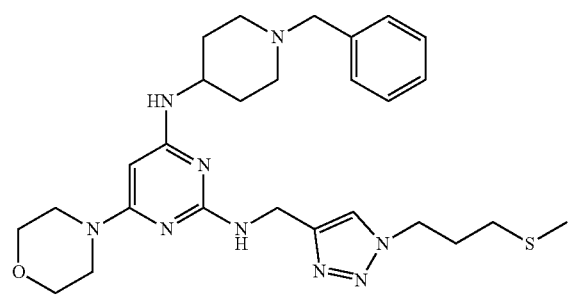
86
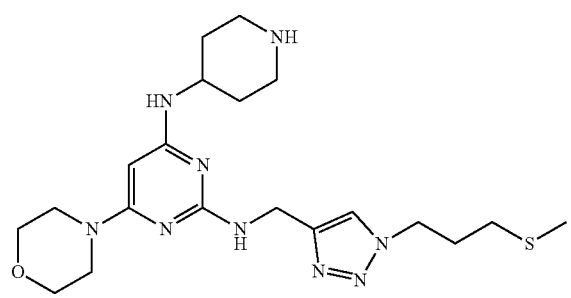

-continued
87
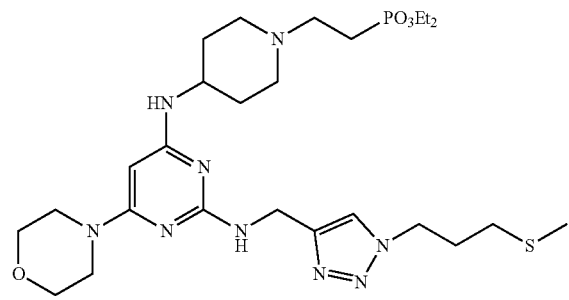
88
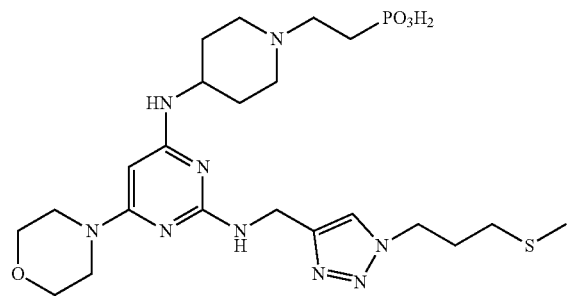
89
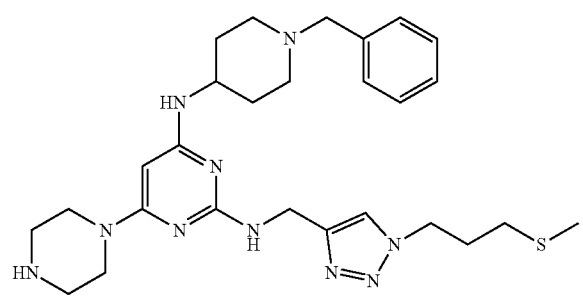
90
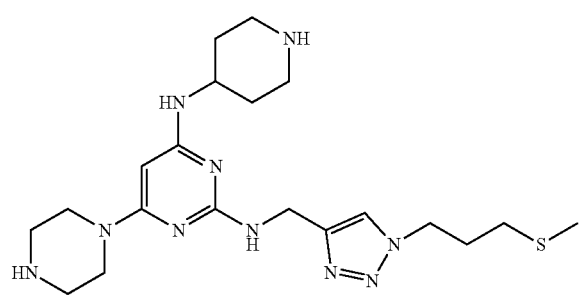
91
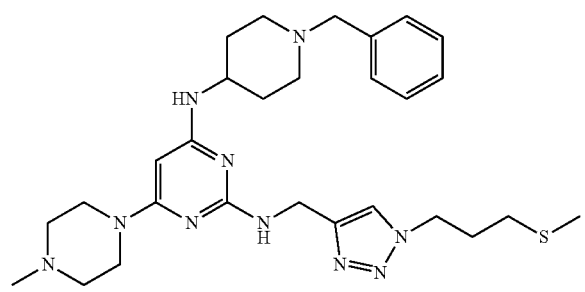
92
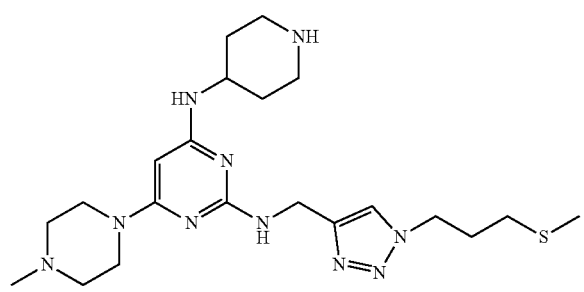
93
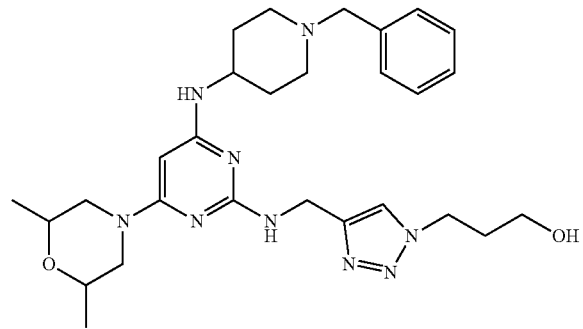
94
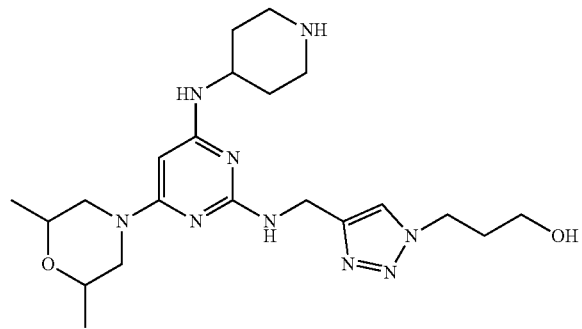
95
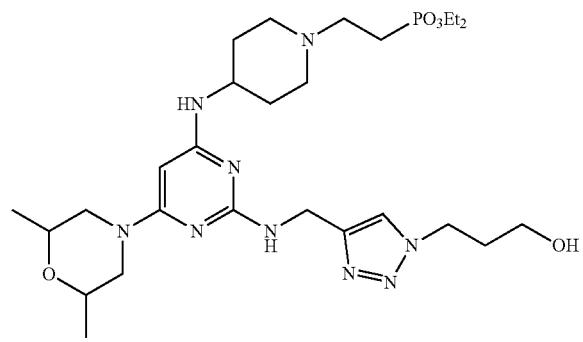
96
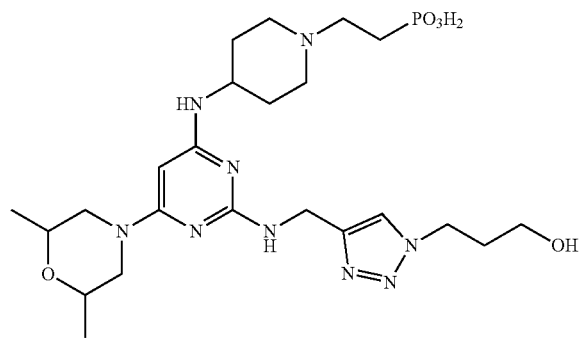

-continued
97
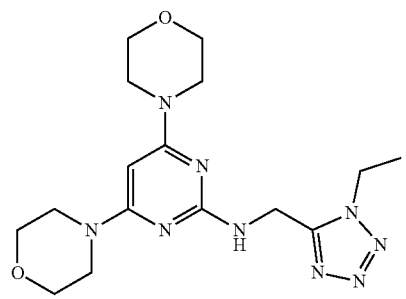
98
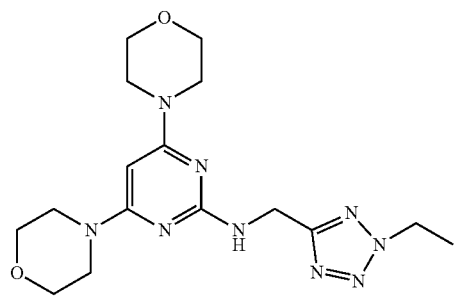
99
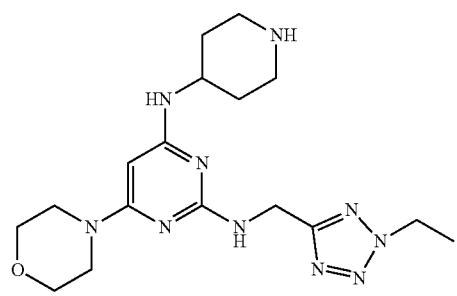
100
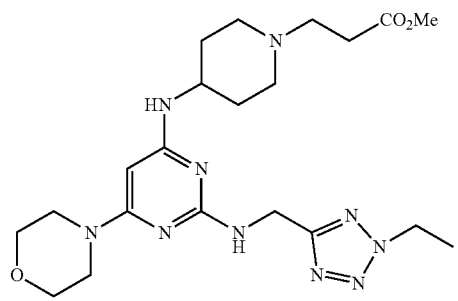
101
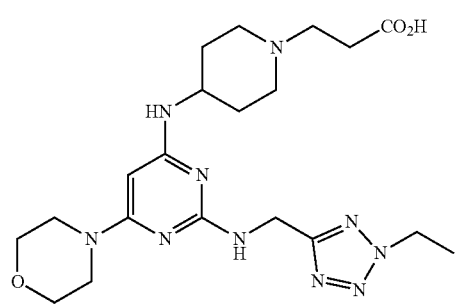
102
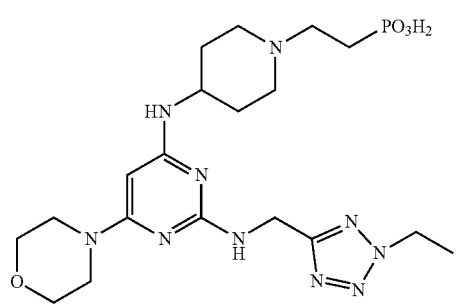
103
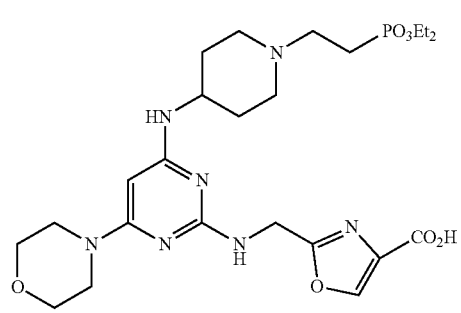
104
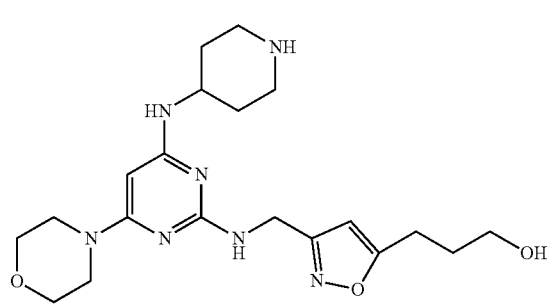
105
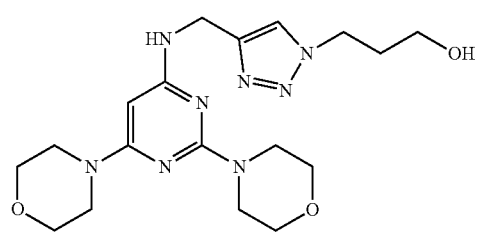
106
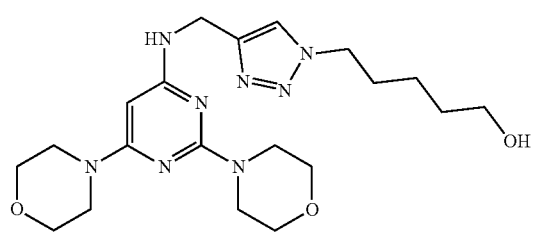

-continued
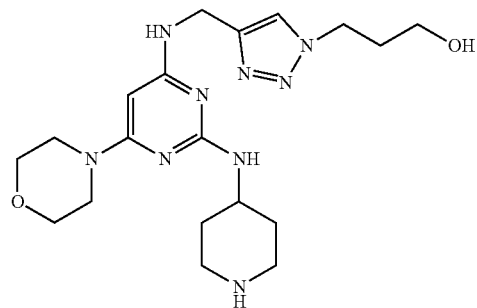
107
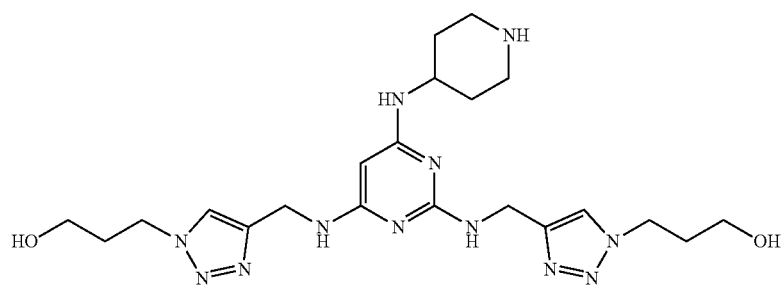
108
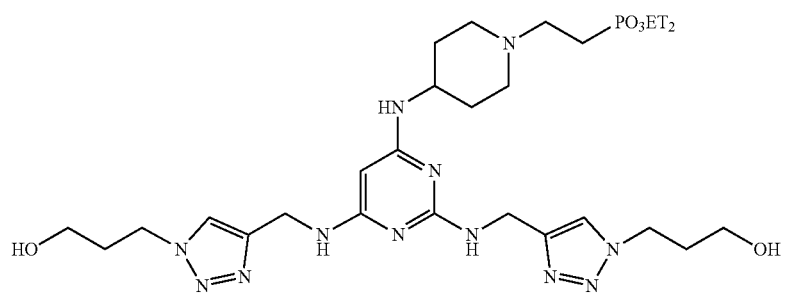
109
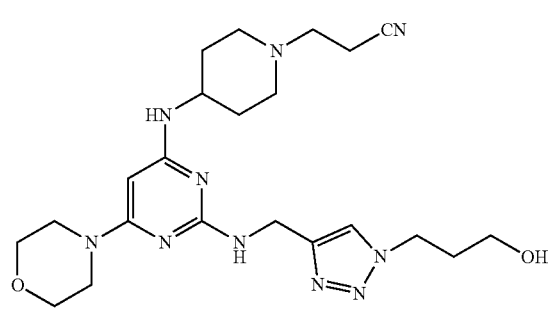
110
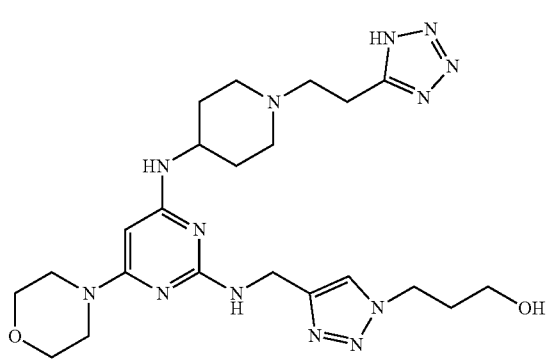
111
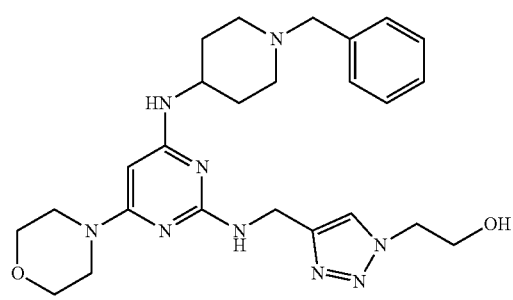
112
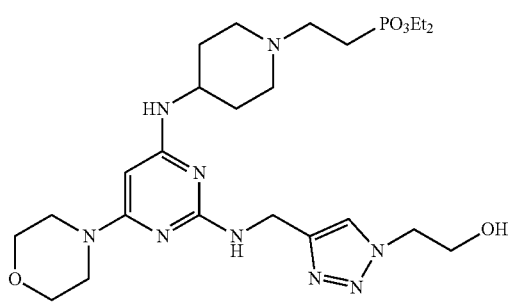
113

-continued
114
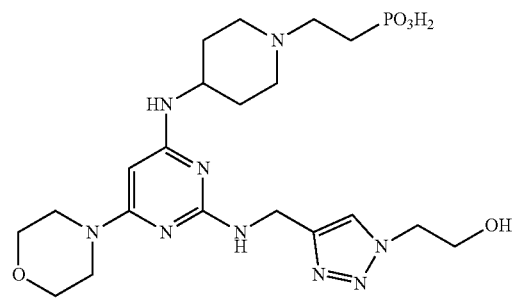
115
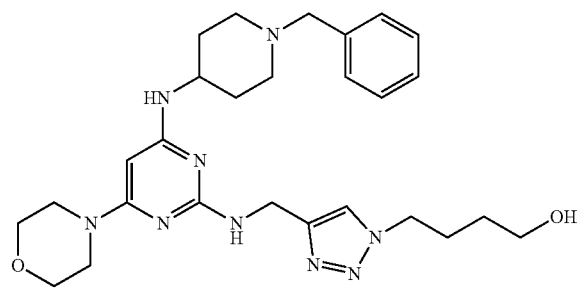
116
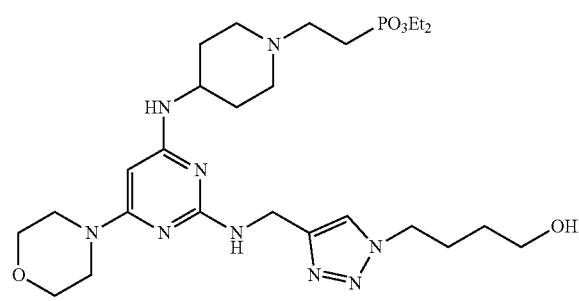
117
118
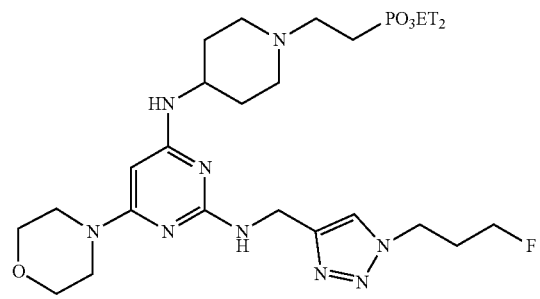
119
120
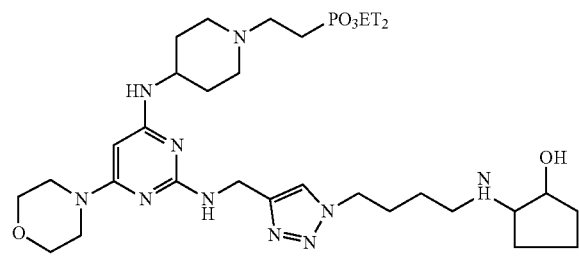
121
122
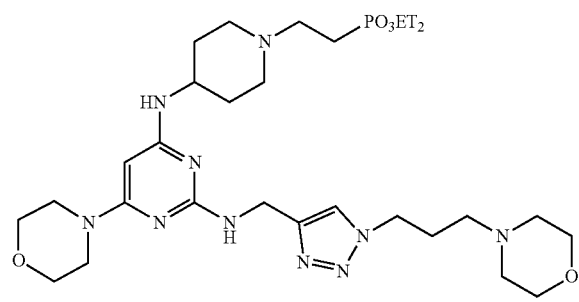
123
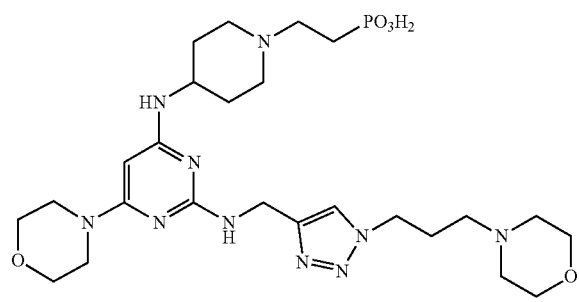

-continued
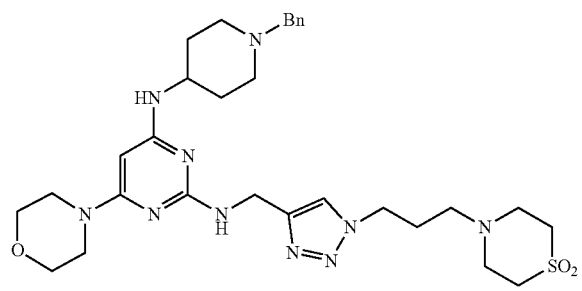
124
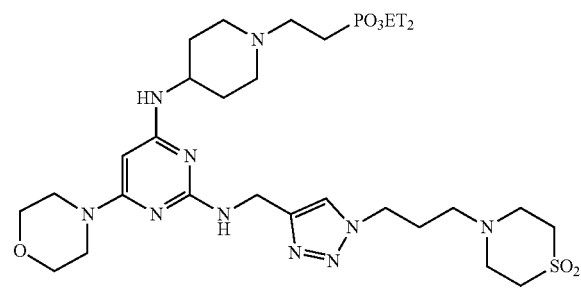
125
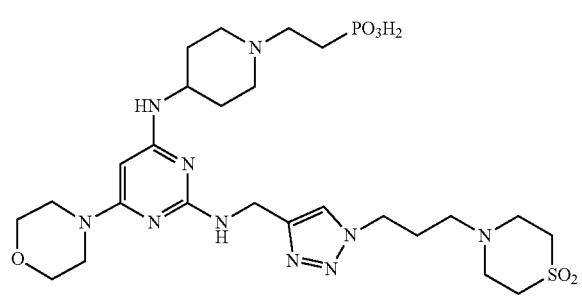
126
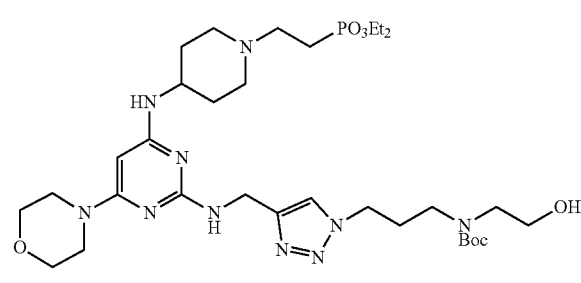
127
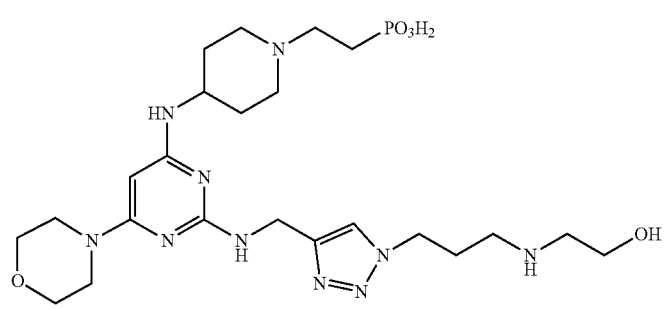
128
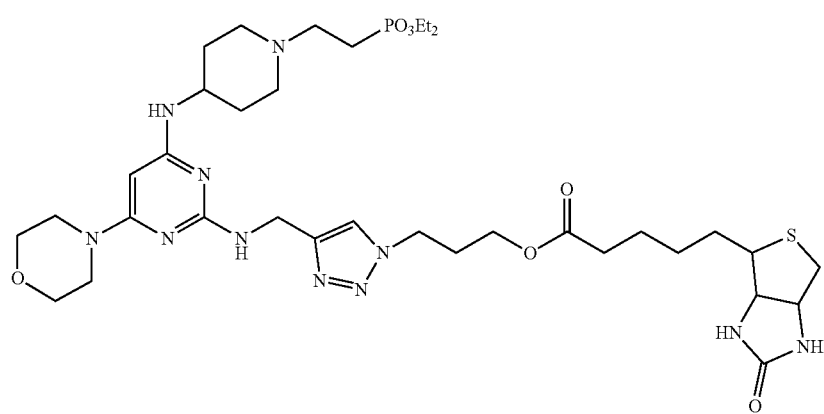
129

-continued
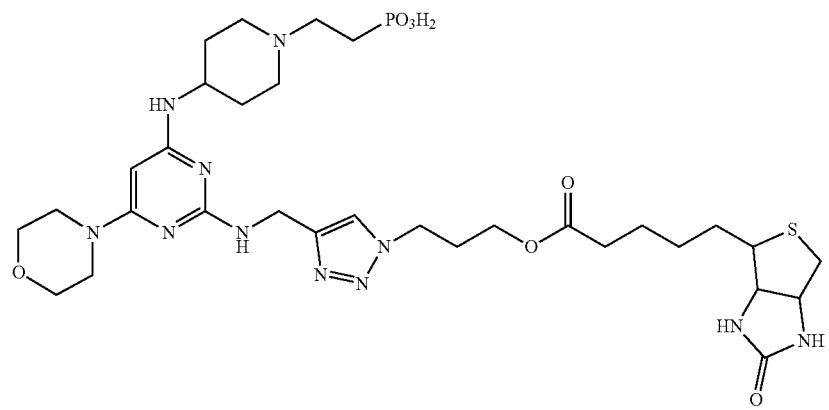
130
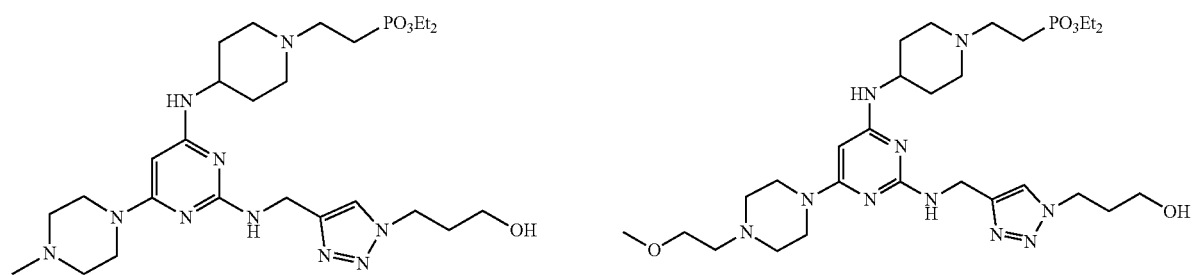
131
132
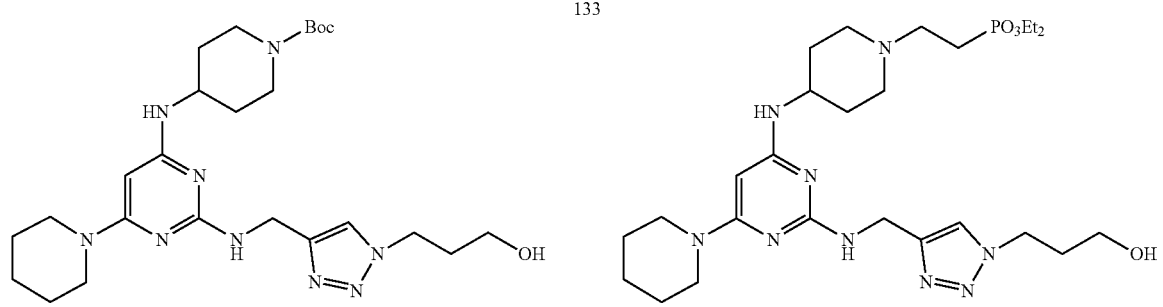
133
134
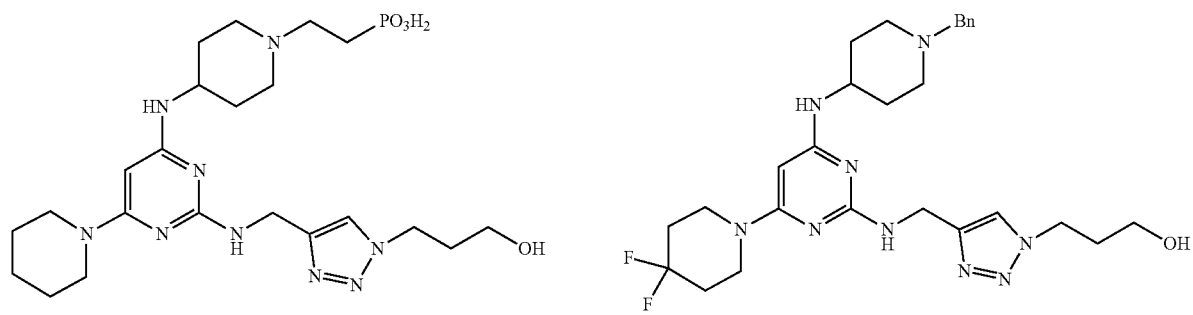
135
136

-continued
137
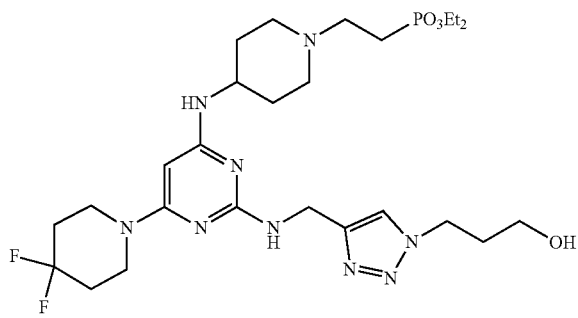
138
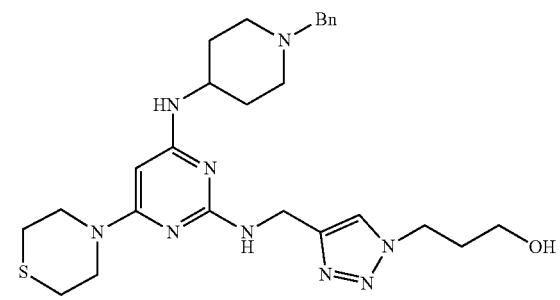
139
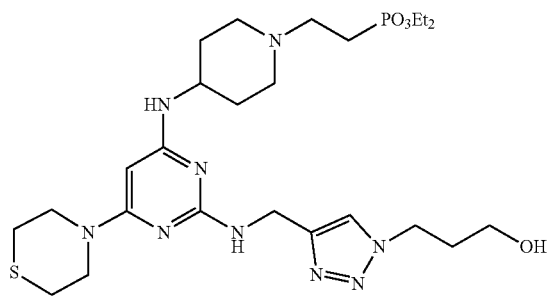
140
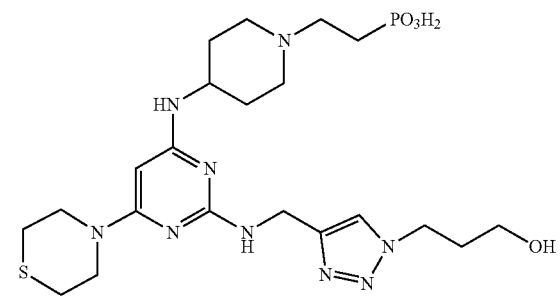
141
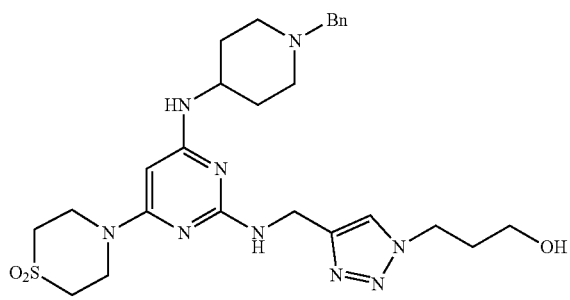
142
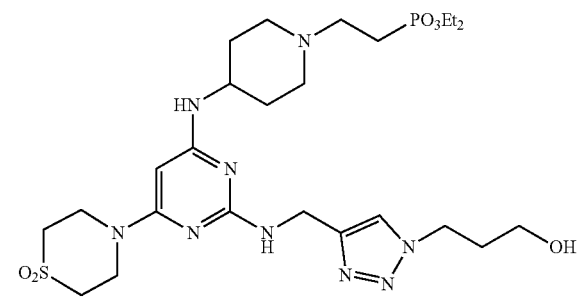
143
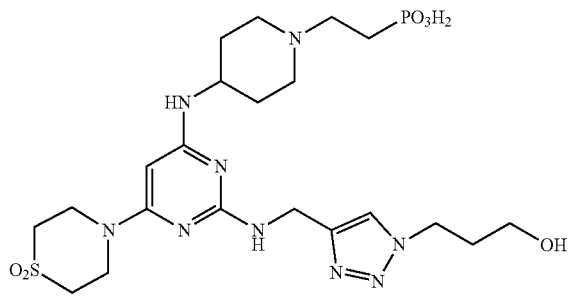
144
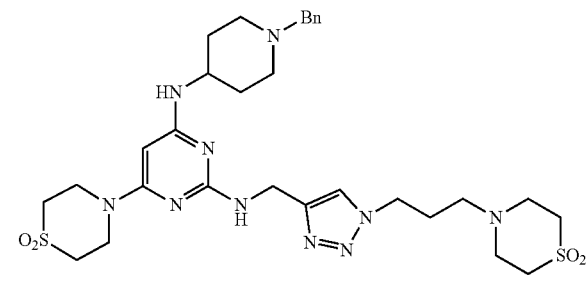
145
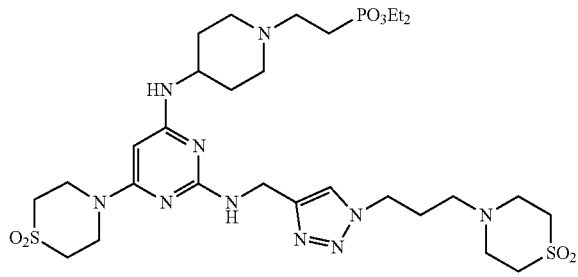
146
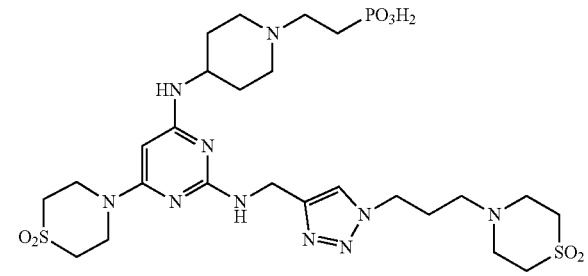

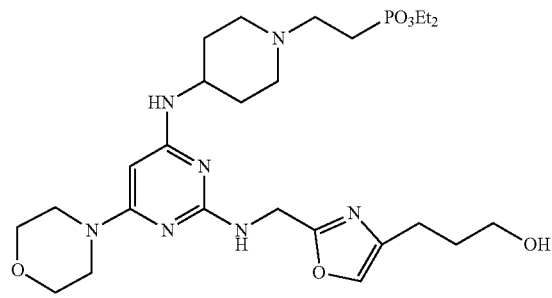

147

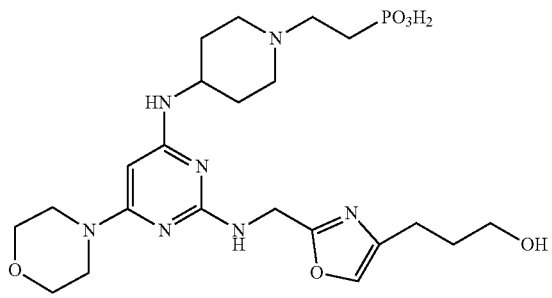

148

The compounds of formula (I) described above can be prepared according to established methods. Synthetic transformations and protecting group methodologies (protection and de-protection) used for preparing these compounds are well known in the art. See, for example, R. Larock, Comprehensive Organic Transformations (3rd Ed., Wiley 2018); P. G. M. Wuts and T. W. Greene, Greene's Protective Groups in Organic Synthesis (4th Ed., John Wiley and Sons 2007); L. Fieser and M. Fieser, Fieser and Fieser's Reagents for Organic Synthesis (John Wiley and Sons 1994); L. Paquette, ed., Encyclopedia of Reagents for Organic Synthesis (2nd ed., John Wiley and Sons 2009); and G. J. Yu et al., J. Med. Chem. 2008, 51, 6044-6054.

Depicted in Scheme I below is a synthetic route for preparing Compounds 1-148 starting from 2,4,6-trichloropyrimidine

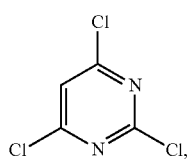

which is optionally substituted with a $R_1$ group. Each of $W_1H$, $W_2H$, and $W_3H$ in Scheme I is an amino compound, which is subjected to a substitution reaction, in a step-by-step manner.

Scheme I

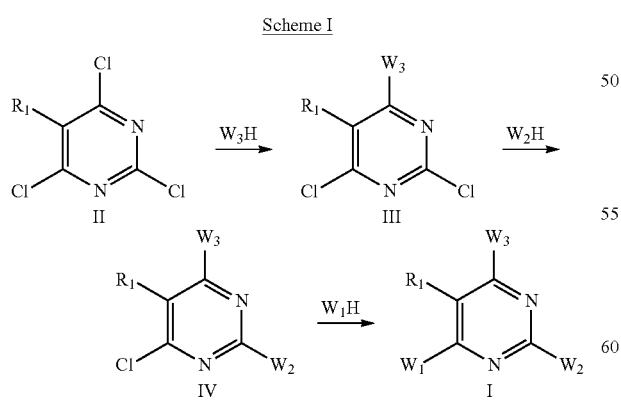

In addition to 2,4,6-trichloropyrimidine, its methanesulfonyl derivatives are also useful as a starting material in the preparation of Compounds 1-148. One example is 4,6-dichloro-2-(methanesulfonyl)pyrimidine, i.e.,

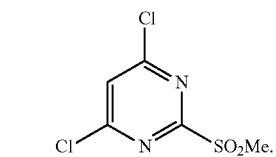 [SMILES: CS(=O)(=O)c1nc(Cl)cc(Cl)n1]

Some of Compounds 1-148 can be prepared using the following moiety (i.e., side chain) compounds, which become moieties corresponding to $W_2$ or $W_3$ in formula (I).

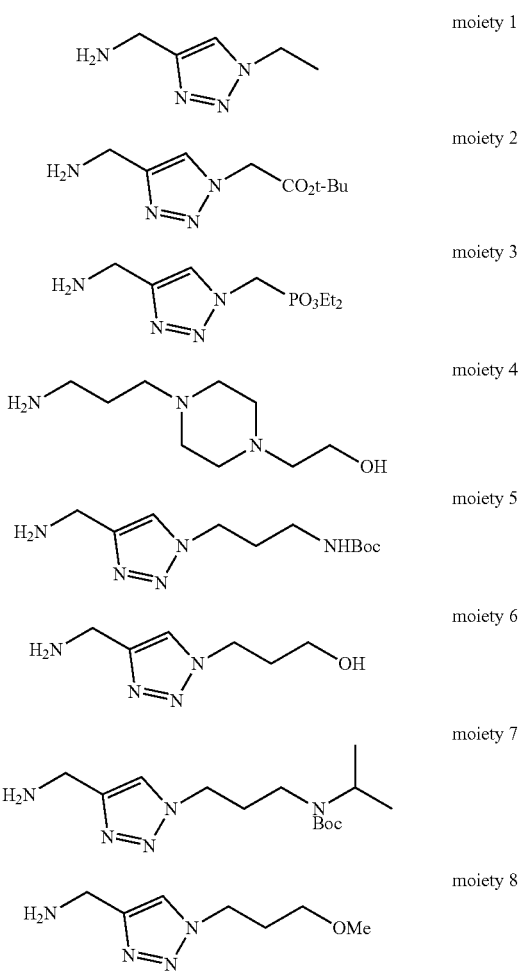

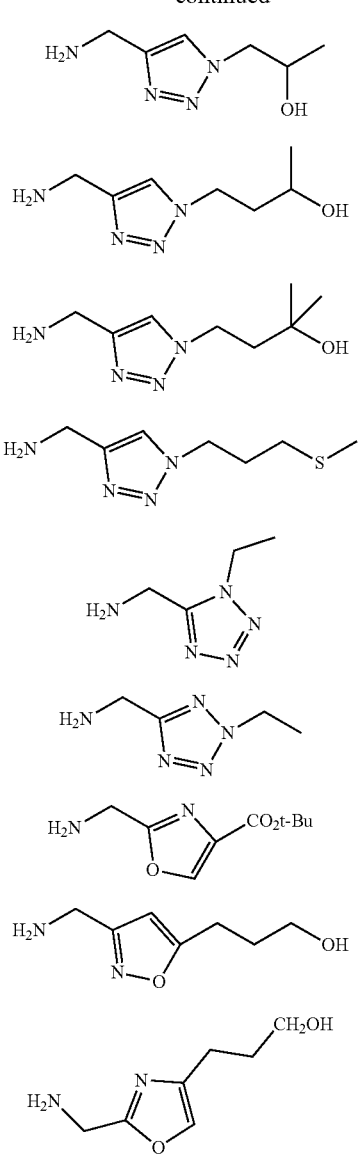

moiety 9
moiety 10
moiety 11
moiety 12
moiety 13
moiety 14
moiety 15
moiety 16
moiety 17

Other side chain compounds are either commercially available or prepared by methods known in the art. The methods could also include additional steps, either before or after the steps described specifically herein, to add or remove suitable protecting groups if necessary to facilitate synthesis of the compounds. In addition, various synthetic steps could be performed in an alternate order to give the desired compounds.

The compounds of formula (I) thus prepared can be initially screened using in vitro assays, e.g., the neurite outgrowth assay described in Example 3 below, for their neuroprotective potency. They can be subsequently evaluated using in vivo animal behavior models (see, e.g., Example 4) for their efficacy in treating or preventing CIPN symptoms. The selected compounds can be further tested to verify their efficacy, e.g., by administering it to an animal. Based on the results, an appropriate dosage range and administration route can be determined.

Without further elaboration, it is believed that one skilled in the art can, based on the above description, utilize the present invention to its fullest extent. The following specific examples are, therefore, to be construed as merely illustrative, and not limitative of the remainder of the disclosure in any way whatsoever.

All publications, including patent documents, cited herein are incorporated by reference in their entirety.

Preparation of moiety compounds 1-17 and pyrimidine compounds 1-148 of this invention are provided in Examples 1 and 2 below.

Example 1: Preparation of Moiety Compounds

All chemicals and reagents were purchased from commercial suppliers, unless otherwise provided. Reactions were carried out under an atmosphere of dry nitrogen and monitored by thin-layer chromatography. Purification was performed using column chromatography. Proton ($^1$H) nuclear magnetic resonance spectra were measured on a Varian Mercury-300 or Varian Mercury-400 spectrometer. Chemical shifts were recorded in parts per million (ppm) on the delta (δ) scale relative to the resonance of the solvent peak. The following abbreviations were used to describe coupling: s=singlet; d=doublet; t=triplet; q=quartet; quin=quintet; br=broad; and m=multiplet. LCMS data were measured on an Agilent 6125B Single Quadrupole LC/MS system.

Preparation of Moiety 1

Moiety 1 was prepared according to the scheme below:

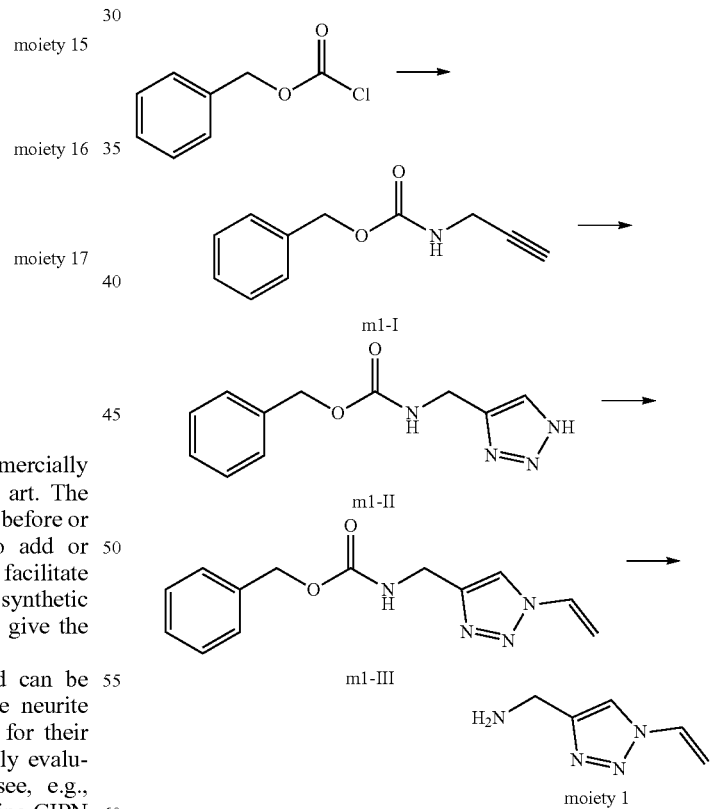

In the first step, benzyl chloroformate (6.07 g, 35.6 mmol) was added at 5-10° C. to a solution of prop-2-ynylamine (1.97 g, 35.8 mmol) and potassium carbonate (10.11 g, 73.3 mmol) in a mixture of tetrahydrofuran ("THF") and water (20 mL/40 mL). The resulting mixture was warmed to room temperature for 15 h and then quenched with NH$_4$Cl(aq.)

(100 mL, 2 M), followed by extraction with ethyl acetate (3×100 mL). The combined organic phases were washed with water and brine, dried over anhydrous sodium sulfate, filtered, and concentrated under reduced pressure to afford a residue. Crystallization of the residue using a solvent mixture of n-hexane/dichloromethane ("DCM") at −20° C. gave m1-I (6.42 g, y: 95%).

$^1$H NMR (CDCl$_3$, 400 MHz) δ 7.38-7.32 (m, 5H), 5.13 (s, 2H), 3.99 (m, 2H), 2.24 (dd, 1H).

In the second step, to a solution of m1-I (6.42 g, 33.9 mmol) and sodium azide (6.42 g, 98.8 mmol) in isopropyl alcohol ("IPA", 150 mL) was added a solution of ZnBr$_2$ (2.5 g, 11.1 mmol) in H$_2$O (36 mL). The mixture was stirred at 75° C. for 15 h and then concentrated to obtain a residue, which was extracted with DCM (3×100 mL). The combined extracts were washed with brine, dried over anhydrous sodium sulfate, filtered, and concentrated to afford m1-II (4.81 g, y: 61%).

In the third step, to a solution of m1-II (4.81 g, 20.7 mmol) in acetonitrile ("ACN", 300 mL) was added 1,2-dibromoethane (4.81 g, 25.6 mmol) and triethylamine ("TEA", 4.81 g, 47.6 mmol). The mixture was refluxed for 15 h and concentrated. The residue thus obtained was then extracted with DCM (2×150 mL). The combined extracts were washed with water and brine, dried over anhydrous sodium sulfate, filtered, and concentrated to obtain a crude residue, which was purified by column chromatography on silica gel (n-hexane:ethyl acetate=1:1) to afford m1-III (3.63 g, y: 68%).

In the last step, a solution of m1-III (3.63 g, 14.1 mmol) and 10% Pd/C (0.36 g) in methanol (72 mL) was stirred under H$_2$(g) at 25° C. for 6 h. The reaction mixture was filtered and concentrated to afford moiety 1 (1.52 g, y: 86%).

Preparation of Moiety 2

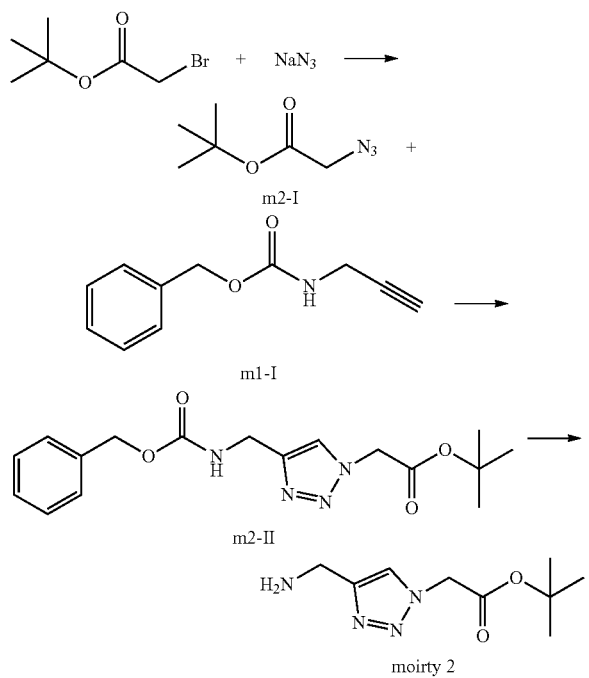

A solution of bromo-acetic acid tert-butyl ester (5.85 g, 30 mmol) and sodium azide (6.56 g, 101 mmol) in acetone/H$_2$O (585 mL/140 mL) was stirred at 25° C. for 15 h and then concentrated to give a residue, which was extracted with DCM (3×100 mL). The combined extracts were washed with brine, dried over anhydrous sodium sulfate, filtered, and concentrated to afford m2-I (3.84 g, y: 81%).

To a solution of m2-I (3.84 g, 24.4 mmol) and m1-I (4.56 g, 24.1 mmol) in ethanol ("EtOH", 150 mL) was added a solution of CuSO$_4$ (0.41 g, 2.6 mmol), (+)-sodium L-ascorbate (0.56 g, 2.8 mmol), K$_2$CO$_3$ (6.71 g, 48.5 mmol) in H$_2$O (36 mL). The mixture was stirred at 25° C. for 15 h and then concentrated to give a residue, which was extracted with DCM (3×100 mL). The combined extracts were washed with brine, dried over anhydrous sodium sulfate, filtered, and concentrated to afford m2-II (6.02 g, y: 71%).

A solution of m2-II (3.01 g, 8.7 mmol) and 10% Pd/C (0.3 g) in methanol (60 mL) was stirred under H$_2$(g) (1 atm) at 25° C. for 6 h. The resulting mixture was then filtered. The filtrate was concentrated to afford moiety 2 (1.64 g, y: 89%).

Preparation of Moiety 3

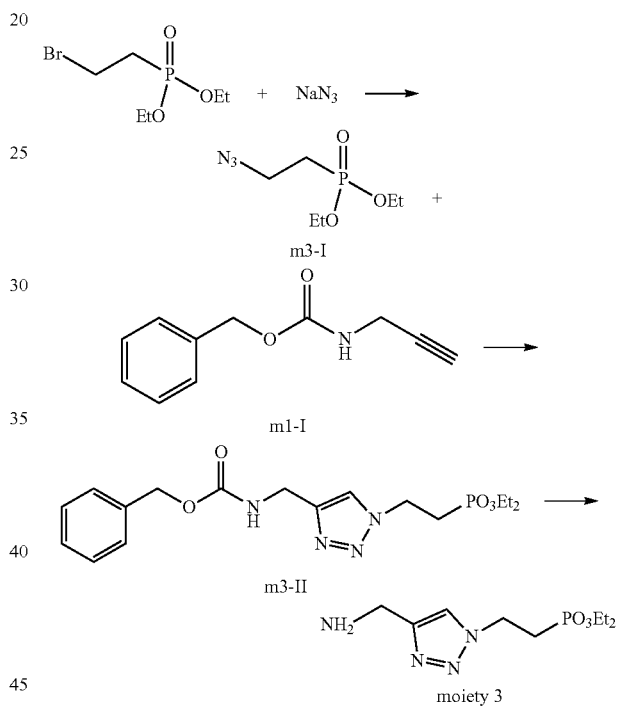

To a solution of (2-bromo-ethyl)-phosphonic acid diethyl ester (2.45 g, 10 mmol) and sodium azide (1.87 g, 28.8 mmol) in acetone/H$_2$O (70 mL/140 mL) was added tetrabutylammonium bromide (1.61 g, 5 mmol). The resulting mixture was stirred at 25° C. for 15 h and then concentrated to give a residue, which was extracted with DCM (3×100 mL). The combined extracts were washed with brine, dried over anhydrous sodium sulfate, filtered, and concentrated to afford m3-I (1.36 g, y: 66%).

To a solution of m3-I (1.36 g, 6.6 mmol) and m1-I (1.25 g, 6.6 mmol) in EtOH (50 mL) was added a solution of CuSO$_4$ (0.13 g, 0.8 mmol), (+) sodium L-ascorbate (0.14 g, 0.7 mmol), K$_2$CO$_3$ (1.84 g, 13.3 mmol) in H$_2$O (36 mL). The mixture was stirred at 25° C. for 15 h and then concentrated to give a residue, which was extracted with DCM (3×50 mL). The combined extracts were washed with brine, dried over anhydrous sodium sulfate, filtered, and concentrated to give the residue, which was purified by column chromatography on silica gel (MeOH:ethyl acetate=1:19) to afford m3-II (2.04 g, y: 77%).

A solution of m3-II (2.04 g, 5.1 mmol) and 10% Pd/C (0.2 g) in methanol (40 mL) was stirred under H₂(g) (1 atm) at 25° C. for 6 h. The reaction mixture was then filtered. The filtrate was concentrated to afford moiety 3 (1.18 g, y: 87%).

Preparation of Moiety 4

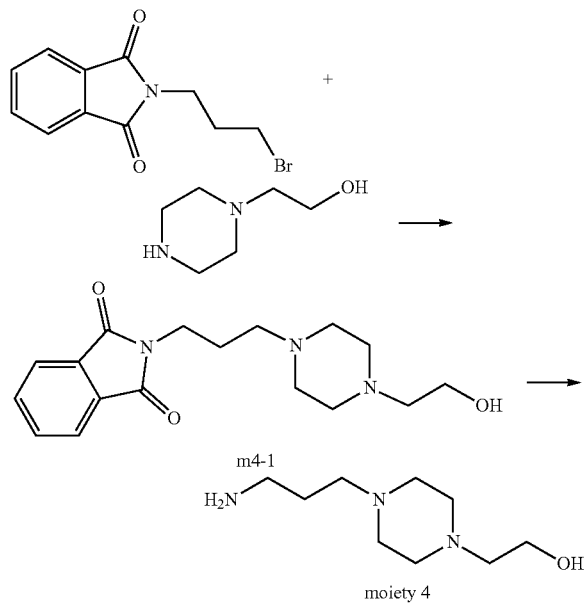

A solution of 2-(3-bromo-propyl)-isoindole-1,3-dione (1.5 g, 5.6 mmol), K₂CO₃ (2 g, 14.5 mmol) and 2-piperazin-1-yl-ethanol (2.5 g, 19.2 mmol) in ACN (120 mL) was stirred at 65° C. for 15 h and then concentrated to give a residue, which was extracted with DCM (3×100 mL). The combined extracts were washed with brine, dried over anhydrous sodium sulfate, filtered, and concentrated to afford m4-I (0.98 g, y: 55%).

A solution of m4-I (0.98 g, 3.1 mmol) and hydrazine monohydrate (0.4 g, 8 mmol) in DCM (20 mL) was stirred at 25° C. for 15 h and then filtrated. The filtrate was concentrated to afford moiety 4 (0.52 g, y: 90%).

Preparation of Moiety 5

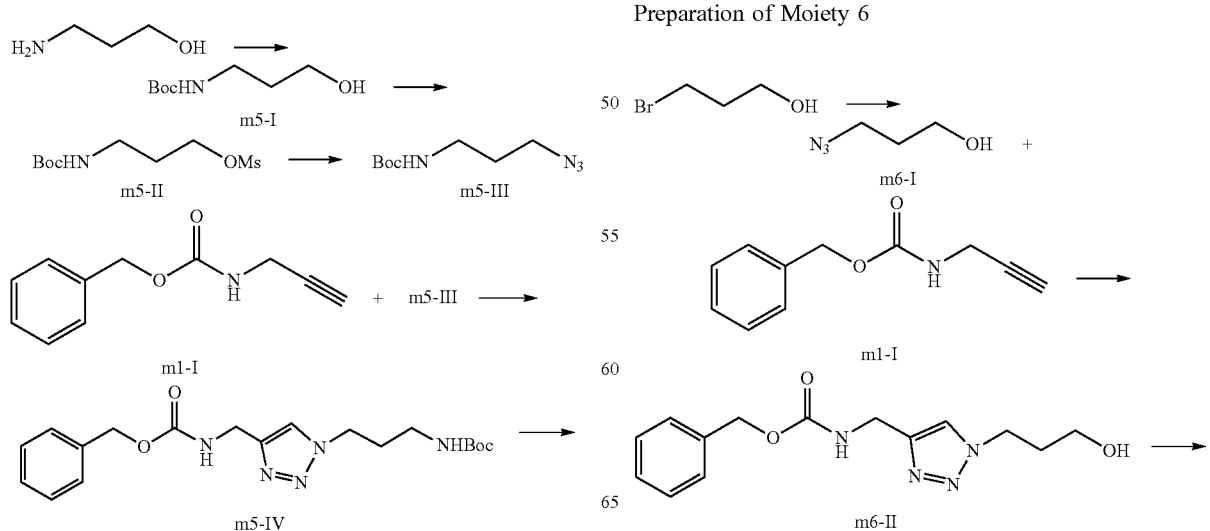

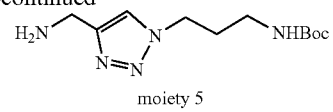
moiety 5

To a solution of 1-aminopropanol (2.25 g, 30 mmol) in DCM was added tert-butoxycarbonyl ("Boc") anhydride ("Boc₂O", 7.81 g, 35.7 mmol) and TEA (3.6 g, 35.6 mmol). The mixture was stirred at room temperature for 15 h and then concentrated to give a crude residue, which was purified by column chromatography on silica gel (n-hexane: ethyl acetate=1:3) to afford m5-I (4.11 g, y: 78%).

To a solution of m5-I (4.11 g, 23.4 mmol) and TEA (3.22 g, 31.7 mmol) in DCM (180 mL) was added methanesulfonyl chloride ("MsCl", 5.41 g, 47.2 mmol) dropwise at 5-10° C. The resulting mixture was warmed to room temperature for 15 h and then quenched with NH₄Cl(aq.) (50 mL, 2 M), followed by extraction with DCM. The combined organic phases were washed with NaHCO₃(aq.) and brine, dried over anhydrous sodium sulfate, filtered, and concentrated to afford m5-II (4.12 g, y: 70%).

To a solution of m5-II (4.12 g, 16.3 mmol) and sodium azide (5.41 g, 83.2 mmol) in MeOH (300 mL) was added tetrabutylammonium bromide (1.61 g, 5 mmol). The resulting mixture was stirred at 65° C. for 15 h and then concentrated to give a residue, which was extracted with DCM (3×100 mL). The combined extracts were washed with brine, dried over anhydrous sodium sulfate, filtered, and concentrated to afford m5-III (2.41 g, y: 74%).

To a solution of m5-III (2.41 g, 12 mmol) and m1-I (2.41 g, 12.7 mmol) in EtOH (160 mL) was added a solution of CuSO₄ (0.2 g, 1.3 mmol), (+)-sodium L-ascorbate (0.24 g, 1.2 mmol), K₂CO₃ (2.24 g, 16.2 mmol) in H₂O (40 mL). The mixture was stirred at 25° C. for 15 h and then concentrated to give a residue, which was extracted with DCM (3×100 mL). The combined extracts were washed with brine, dried over anhydrous sodium sulfate, filtered, and concentrated to afford m5-IV (3.12 g, y: 67%).

A solution of m5-IV (3.12 g, 8 mmol) and 10% Pd/C (0.6 g) in methanol (40 mL) was stirred under H₂(g) (1 atm) at 25° C. for 6 h and then filtered. The filtrate was concentrated to afford moiety 5 (1.82 g, y: 89%).

Preparation of Moiety 6

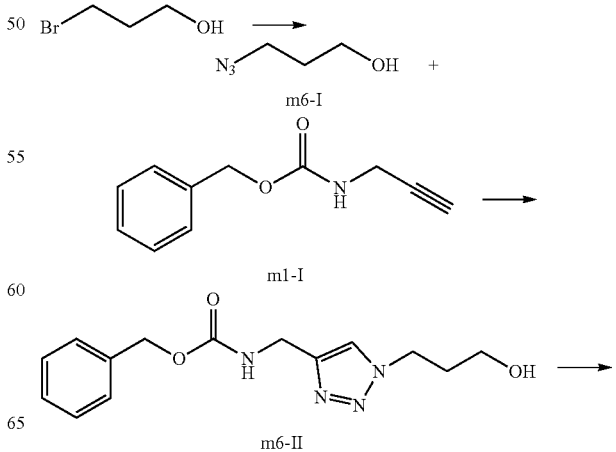

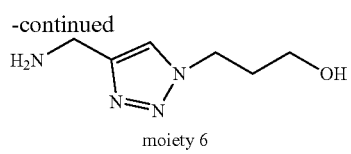

moiety 6

To a solution of 3-bromo-1-propanol (20 g, 144 mmol) in water/acetone (100 mL/35 mL) was added NaN₃ (11.3 g, 174 mmol) and KI (2.02 g, 12.2 mmol) at room temperature. The reaction mixture was stirred at 25° C. for 15 h and then concentrated. The resulting residue was extracted with ethyl acetate. The combined extracts were washed with water and brine, dried over anhydrous sodium sulfate, and filtered. The filtrate was concentrated to afford m6-I (14.12 g, y: 97%).

To a solution of m1-I (15.4 g, 81.4 mmol) and m6-I (8.23 g, 81.4 mmol) in EtOH (690 mL) was added a solution of CuSO₄ (2.01 g, 12.6 mmol), (+)-sodium L-ascorbate (4 g, 20.2 mmol), and K₂CO₃ (11.31 g, 81.8 mmol) in H₂O (69 mL). The reaction mixture was stirred at 25° C. for 15 h and then concentrated. The resulting residue was extracted with DCM. The combined extracts were washed with water and brine, dried over anhydrous sodium sulfate, filtered, and concentrated. The residue thus obtained was purified by column chromatography on silica gel (n-hexane:ethyl acetate=1:3) to afford m6-II (19.74 g, y: 84%).

A solution of m6-II (2 g, 6.9 mmol) and 10% Pd/C (0.6 g) in IPA (40 mL) was stirred under H₂(g) (1 atm) at 60° C. for 15 h and filtered. The filtrate was concentrated to afford moiety 6 (1 g, y: 93%).

Preparation of Moiety 7

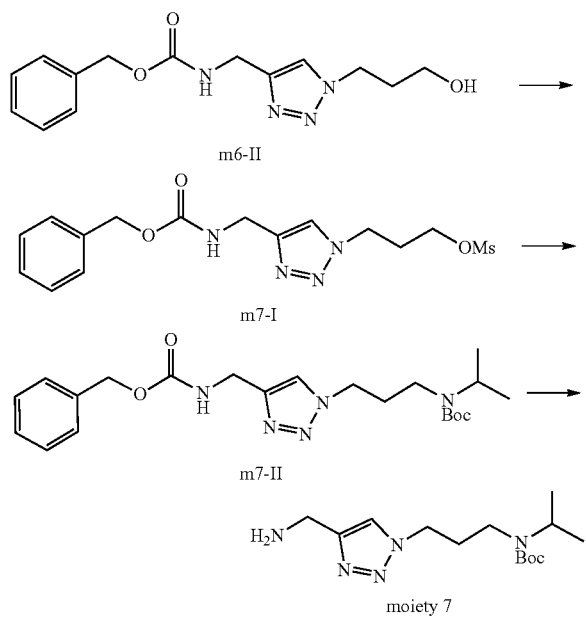

To a solution of m6-II (5 g, 17.2 mmol) in dry DCM (100 mL) was added TEA (2.6 g, 25.7 mmol) and MsCl (2.37 g, 20.7 mmol) at 5° C. The reaction mixture was stirred at 60° C. for 15 h and then quenched with NH₄Cl(aq.) (50 mL, 2M). The resulting residue was extracted with DCM. The combined extracts were washed with water and brine, dried over anhydrous sodium sulfate, and filtered. The filtrate was concentrated to afford m7-I (4.56 g, y: 72%).

To a solution of m7-I (4.56 g, 12.4 mmol) in dry THF (50 mL) was added isopropylamine (5.6 g, 94.7 mmol) at 5° C. The reaction mixture was stirred at room temperature for 15 h and then quenched with NH₄Cl(aq.) (50 mL, 2 M). The resulting mixture was extracted with ethyl acetate. The combined extracts were washed with water and brine, dried over anhydrous sodium sulfate, filtered, and concentrated. The residue thus obtained was dissolved in DCM (50 mL) and mixed with Boc₂O (3.4 g, 15.6 mmol) and TEA (1.6 g, 15.8 mmol). The mixture was stirred at room temperature for 15 h and then concentrated to give a crude residue, which was purified by column chromatography on silica gel (n-hexane:ethyl acetate=1:3) to afford m7-II (3.51 g, y: 66%).

A solution of m7-II (3.51 g, 8.1 mmol) and 10% Pd/C (1.05 g) in IPA (100 mL) was stirred under H₂(g) (1 atm) at 60° C. for 15 h and filtered. The filtrate was concentrated to afford moiety 7 (2.2 g, y: 91%).

Preparation of Moiety 8

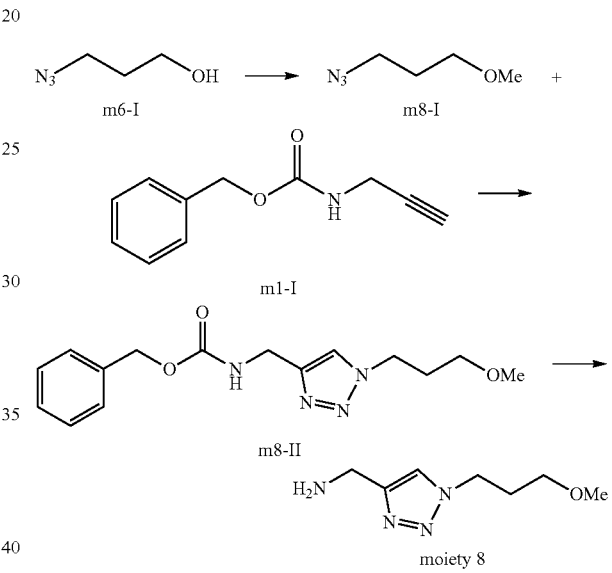

To a solution of m6-I (5 g, 49.5 mmol) in solution of dry dimethylformamide ("DMF", 40 mL) was added KOH (11 g, 196.4 mmol) at 5° C. The reaction mixture was stirred at 5° C. for 0.5 h. Iodomethane (14 g, 98.6 mmol) was then added to the solution. The mixture was stirred at room temperature for 15 h and concentrated. The resulting residue was extracted with ethyl acetate. The combined extracts were washed with water and brine, dried over anhydrous sodium sulfate, and filtered. The filtrate was concentrated to afford m8-I (1.62 g, y: 28%).

To a solution of m8-I (1.62 g, 14.1 mmol) and m1-I (2.67 g, 14.1 mmol) in EtOH (60 mL) was added a solution of CuSO₄ (0.34 g, 2.1 mmol), (+)-sodium L-ascorbate (0.84 g, 4.2 mmol), and K₂CO₃ (1.94 g, 14 mmol) in H₂O (15 mL). The reaction mixture was stirred at 25° C. for 15 h and then concentrated. The resulting residue was extracted with DCM. The combined extracts were washed with water and brine, dried over anhydrous sodium sulfate, filtered, and concentrated. The residue thus obtained was purified by column chromatography on silica gel (n-hexane:ethyl acetate=1:2) to afford m8-II (3.03 g, y: 71%).

A solution of m8-II (3.03 g, 10 mmol) and 10% Pd/C (0.9 g) in IPA (60 mL) was stirred under H₂(g) (1 atm) at 60° C. for 15 h and filtered. The filtrate was concentrated to afford moiety 8 (1.66 g, y: 98%).

Preparation of Moiety 9

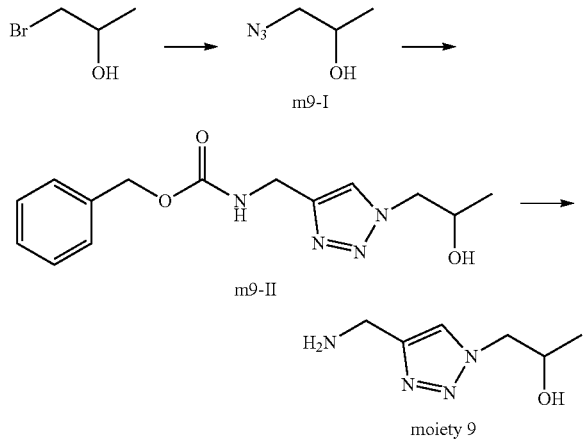

To a solution of 1-bromopropan-2-ol (1.51 g, 10.8 mmol) in DMF (16 mL) was added NaN$_3$ (3.01 g, 46.2 mmol) and Na$_2$CO$_3$ (2.32 g, 21.7 mmol) at room temperature. The reaction mixture was stirred at 25° C. for 15 h and then concentrated. The resulting residue was extracted with ethyl acetate. The combined extracts were washed with water and brine, dried over anhydrous sodium sulfate, and filtered. The filtrate was concentrated to afford m9-I (0.87 g, y: 80%).

To a solution of m9-I (0.75 g, 7.4 mmol) and m1-I (1.7 g, 9 mmol) in EtOH (38 mL) was added a solution of CuSO$_4$ (0.4 g, 2.5 mmol), (+)-sodium L-ascorbate (0.75 g, 3.8 mmol), and K$_2$CO$_3$ (1.2 g, 8.7 mmol) in H$_2$O (19 mL). The reaction mixture was stirred at 25° C. for 15 h and then concentrated. The resulting residue was extracted with DCM. The combined extracts were washed with water and brine, dried over anhydrous sodium sulfate, filtered, and concentrated. The residue thus obtained was purified by column chromatography on silica gel (n-hexane:ethyl acetate=1:3) to afford m9-II (1.61 g, y: 75%).

A solution of m9-II (1.61 g, 5.5 mmol) and 10% Pd/C (0.48 g) in IPA (32 mL) was stirred under H$_2$(g) (1 atm) at 60° C. for 15 h and filtered. The filtrate was concentrated to afford moiety 9 (0.79 g, y: 92%).

Preparation of Moiety 10

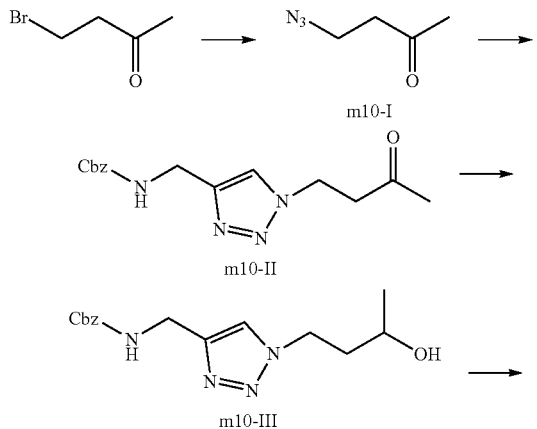

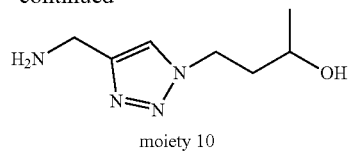

To a solution of 4-bromo-butan-2-one (1.51 g, 10 mmol) in dimethylformamide (16 mL) was added NaN$_3$ (3.01 g, 46.2 mmol) and KI (0.23 g, 1.4 mmol) at room temperature. The reaction mixture was stirred at 25° C. for 15 h and then concentrated. The resulting residue was extracted with ethyl acetate. The combined extracts were washed with water and brine, dried over anhydrous sodium sulfate, and filtered. The filtrate was concentrated to afford m10-I (0.87 g, y: 77%).

To a solution of m10-I (0.87 g, 7.7 mmol) and m1-I (1.7 g, 9 mmol) in EtOH (38 mL) was added a solution of CuSO$_4$ (0.4 g, 2.5 mmol), (+)-sodium L-ascorbate (0.75 g, 3.8 mmol), and K$_2$CO$_3$ (1.2 g, 8.7 mmol) in H$_2$O (19 mL). The reaction mixture was stirred at 25° C. for 15 h and then concentrated. The resulting residue was extracted with DCM. The combined extracts were washed with water and brine, dried over anhydrous sodium sulfate, filtered, and concentrated. The residue thus obtained in the previous step was purified by column chromatography on silica gel (n-hexane:ethyl acetate=1:3) to afford m10-II (1.98 g, y: 85%).

To a solution of m10-II (1.98 g, 6.5 mmol) in dry MeOH (30 mL) was added NaBH$_4$ (0.72 g, 19 mmol) at 5° C. The reaction mixture was stirred at 5° C. for 3 h and then quenched with aqueous NH$_4$Cl. The resulting mixture was extracted with ethyl acetate. The combined extracts were washed with water and brine, dried over anhydrous sodium sulfate, and filtered. The filtrate was concentrated to afford m10-III (1.61 g, y: 81%).

A solution of m10-III (1.61 g, 5.3 mmol) and 10% Pd/C (0.32 g) in 2-propanol (32 mL) was stirred under H$_2$ (1 atm) at 60° C. for 15 h and filtered. The filtrate was concentrated to afford moiety 10 (0.83 g, y: 93%).

Preparation of Moiety 11

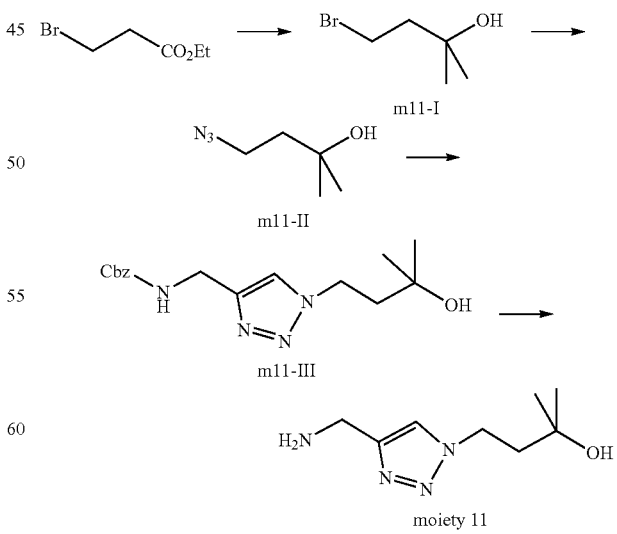

To a solution of ethyl 3-bromopropanoate (2 g, 11 mmol) in dry THF (45 mL) was added a solution of methylmagnesium bromide (8 mL, 3 M in THF). The mixture was stirred at 25° C. for 4 h and then quenched with NH₄Cl(aq.) (50 mL, 2 M). The resulting mixture was extracted with ethyl acetate. The combined organic phases were washed with brine, dried over anhydrous sodium sulfate, filtered, and concentrated to afford m11-I (1.21 g, y: 65%)

To a solution of m11-I (1.21 g, 7.2 mmol) in DMF (12 mL) was added NaN₃ (2.31 g, 35.4 mmol) and Na₂CO₃ (2.02 g, 19.1 mmol) at room temperature. The reaction mixture was stirred at 25° C. for 15 h and then concentrated. The resulting residue was extracted with ethyl acetate. The combined extracts were washed with water and brine, dried over anhydrous sodium sulfate, and filtered. The filtrate was concentrated to afford m11-II (0.72 g, y: 78%).

To a solution of m11-II (0.72 g, 5.6 mmol) and m1-I (1.56 g, 8.2 mmol) in EtOH (19 mL) was added a solution of CuSO₄ (0.24 g, 1.5 mmol), (+)-sodium L-ascorbate (0.48 g, 2.4 mmol), and K₂CO₃ (0.84 g, 6.1 mmol) in H₂O (8.4 mL). The reaction mixture was stirred at 25° C. for 15 h and then concentrated. The resulting residue was extracted with DCM. The combined extracts were washed with water and brine, dried over anhydrous sodium sulfate, filtered, and concentrated. The residue thus obtained was purified by column chromatography on silica gel (MeOH:ethyl acetate=1:19) to afford m11-III (1.2 g, y: 68%)

A solution of m11-III (1.2 g, 3.8 mmol) and 10% Pd/C (0.36 g) in IPA (24 mL) was stirred under H₂(g) (1 atm) at 60° C. for 15 h and then filtered. The filtrate was concentrated to afford moiety 11 (0.61 g, y: 88%).

Preparation of Moiety 12

Moiety 12 was prepared from 1-bromo-3-methylsulfanyl-propane following a procedure similar to that used to prepare moiety 6.

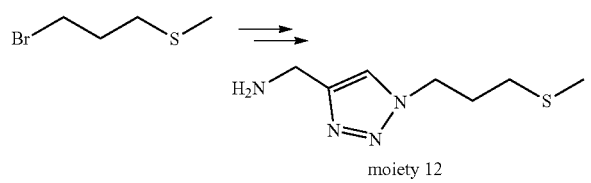

moiety 12

Preparation of Moiety 13 and 14

Moiety 13 and 14 were prepared from amino-acetonitrile following a procedure similar to that used to prepare moiety 1.

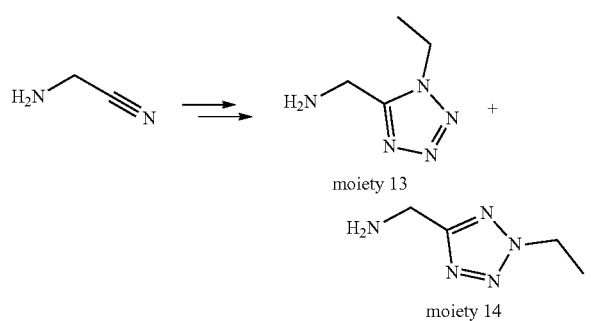

moiety 13 moiety 14

Preparation of Moiety 15

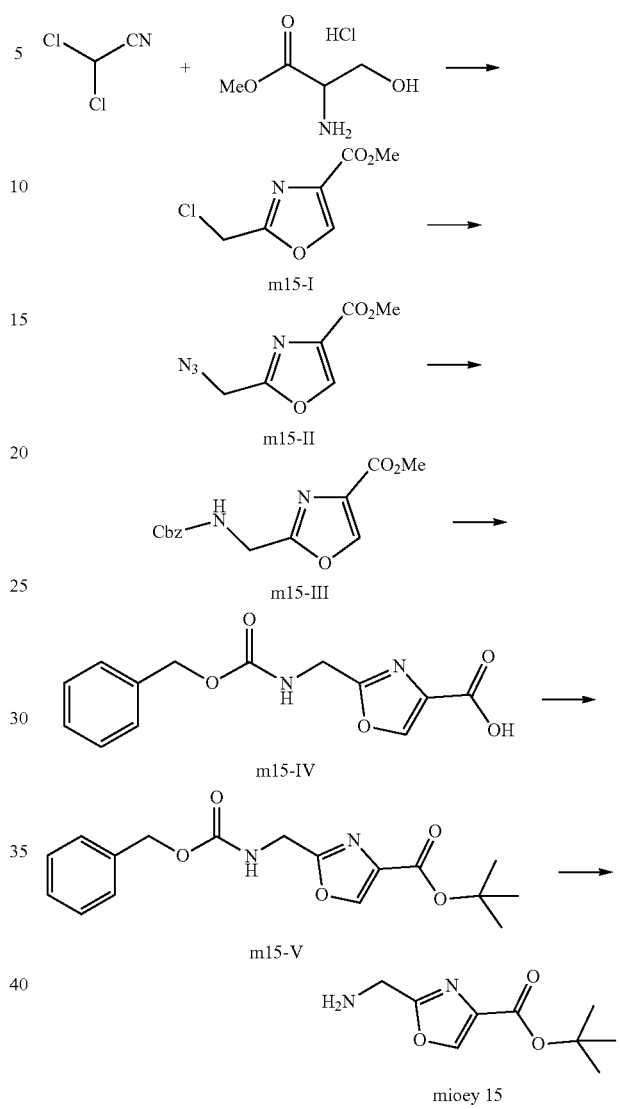

To a solution of sodium methoxide (0.1 mL, 5.4 M in MeOH) in DCM (100 mL) and MeOH (10 mL) at 0° C. was added dichloroacetonitrile (5.02 g, 45.7 mmol) over 45 min. After the mixture was stirred at 0° C. for 1 h, L-serine methyl ester hydrochloride (7.91 g, 50.8 mmol) was added. The reaction mixture was stirred at 25° C. for 15 h and then quenched with water. The resulting solution was concentrated and then extracted with DCM (3×150 mL). The combined extracts were washed with water and brine, dried over anhydrous sodium sulfate, filtered, and concentrated to give a crude residue. A mixture of the residue and N,N-diisopropylethylamine (8.91 g, 68.9 mmol) in DCM (150 mL) was stirred at 50° C. for 15 h and then quenched with NH₄Cl(aq.) (50 mL, 2 M). The aqueous phase was separated and extracted with DCM (2×50 mL). The combined organic phases were washed with water, brine, dried over anhydrous sodium sulfate, filtered, and concentrated. The residue thus obtained was purified by column chromatography (n-hexane:ethyl acetate=4:1) to afford m15-I (7.85 g, y: 98%).

¹H NMR (CDCl₃, 300 MHz) δ 8.25 (s, 1H), 4.64 (s, 2H), 3.93 (s, 3H).

A mixture of the m15-I (8.01 g, 45.6 mmol) and sodium azide (10 g, 153.8 mmol) in DMF (240 mL) was stirred at 25° C. for 15 h and then quenched with NH$_4$Cl(aq.) (50 mL, 2 M). The resulting solution was extracted with diethyl ether. The combined extracts were washed with water and brine, dried over anhydrous sodium sulfate, filtered, and concentrated. The residue thus obtained was purified by column chromatography on silica gel (n-hexane:ethyl acetate=4:1) to afford m15-II (6.91 g, y: 83%).

$^1$H NMR (CDCl$_3$, 400 MHz) δ 8.25 (s, 1H), 4.46 (s, 2H), 3.90 (s, 3H).

A mixture of m15-II (6.91 g, 37.9 mmol) and triphenylphosphine (10.42 g, 39.7 mmol) in water (105 mL)/THF (210 mL) was stirred at 25° C. for 15 h. The resulting mixture was concentrated to remove THF. The residue thus obtained was washed with ethyl acetate. An amino product was obtained and remained in the aqueous phase, to which was introduced at 5-10° C. NaHCO$_3$ (6.37 g, 75.8 mmol), THF (105 mL), and benzyl chloroformate (5.81 g, 34 mmol). The mixture was stirred at room temperature for 15 h and then quenched with NH$_4$Cl(aq.) (50 mL, 2 M). The resulting mixture was extracted with ethyl acetate. The combined extracts were washed with water and brine, dried over anhydrous sodium sulfate, filtered, and concentrated. The residue thus obtained was purified by column chromatography on silica gel (n-hexane:ethyl acetate=3:1) to afford m15-III (7.13 g, y: 65% over 2 steps).

$^1$H NMR (CDCl$_3$, 400 MHz) δ 8.17 (s, 1H), 7.35-7.28 (m, 5H), 5.69 (br s, NH), 5.11 (s, 2H), 4.53 (d, 2H), 3.88 (s, 3H).

To a solution of m15-III (3 g, 10.3 mmol) in THE (40 mL) was added LiOH(aq.) (20 mL, 1 N). The mixture was stirred at 25° C. for 16 h and then quenched with NH$_4$Cl(aq.) (50 mL, 2 M). The resulting mixture was extracted with ethyl acetate. The combined organic phases were washed with brine, dried over anhydrous sodium sulfate, filtered, and concentrated to afford m15-IV (2.25 g, y: 79%).

To m15-IV (2.25 g, 8.1 mmol) was added Boc$_2$O (2.61 g, 11.9 mmol) and 4-dimethylaminopyridine (1.4 g, 11.5 mmol). The resulting mixture was stirred at room temperature for 15 h and then concentrated to give a crude residue, which was purified by column chromatography on silica gel (n-hexane:ethyl acetate=1:1) to afford m15-V (2.06 g, y: 76%).

A solution of m15-V (2.06 g, 6.2 mmol) and 10% Pd/C (0.6 g) in IPA (40 mL) was stirred under H$_2$(g) (1 atm) at 60° C. for 15 h and filtered. The filtrate was concentrated to afford moiety 15 (1.11 g, y: 90%).

Preparation of Moiety 16

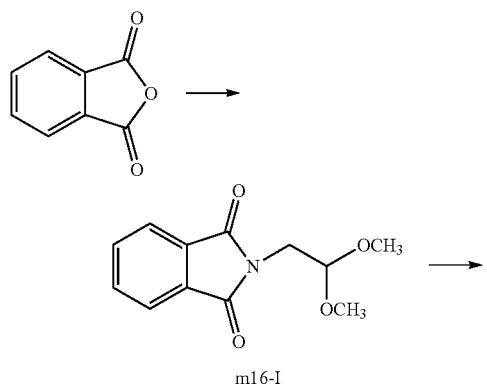

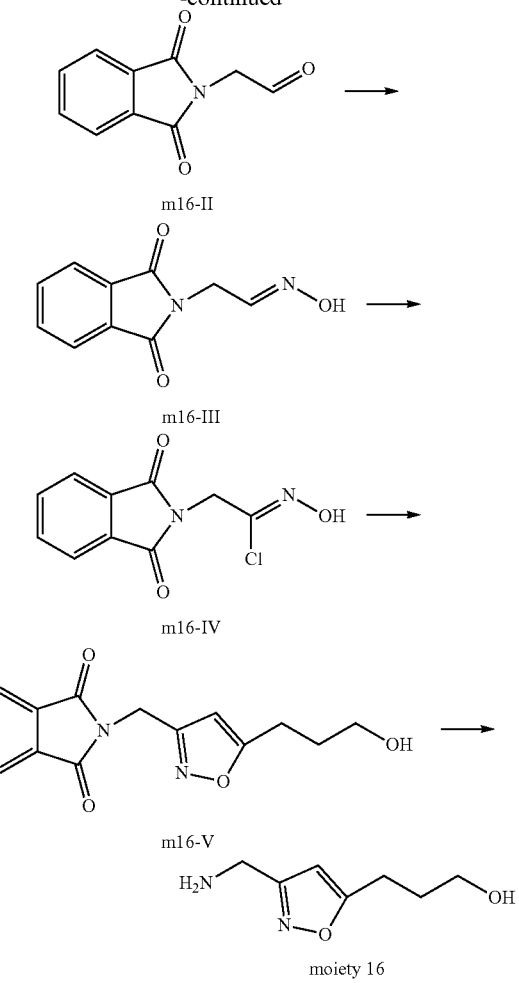

moiety 16

A solution of phthalic anhydride (10 g, 67.5 mmol), aminoacetaldehyde (7.81 g, 74.3 mmol) and N,N-diisopropylethylamine (13.09 g, 101.3 mmol) in toluene was heated at 120° C. for 16 h and then quenched with NH$_4$Cl(aq.) (100 mL, 2 M). The aqueous phase was extracted with ethyl acetate (3×50 mL). The combined organic phases were washed with water and brine, dried over anhydrous sodium sulfate, filtered. The filtrate was concentrated to afford m16-I (15.49 g, y: 98%).

To a solution of m16-I (15.49 g, 65.8 mmol) in EtOH/H$_2$O (20 mL/40 mL) was added HCl(aq.) (120 mL, 6 N). The mixture was heated at 80° C. for 16 h and then concentrated. The residue was extracted with ethyl acetate (3×50 mL). The combined organic phases were washed with NaHCO$_3$(aq.) and brine, dried over anhydrous sodium sulfate, and filtered. The filtrate was concentrated to afford m16-II (6.26 g, y: 50%).

To a solution of m16-II (6.26 g, 33.1 mmol) and TEA (10 g, 99.4 mmol) in DCM (100 mL) at 5-10° C. was added hydroxylamine hydrochloride (2.53 g, 36.4 mmol). The mixture was stirred at room temperature for 15 h and then quenched with NH$_4$Cl(aq.) (50 mL, 2M). The aqueous phase was extracted with DCM (2×50 mL). The combined organic phases were washed with NaHCO$_3$(aq.) and brine, dried over anhydrous sodium sulfate, and filtered. The filtrate was concentrated to afford m16-III (4.01 g, y: 59%).

A solution of m16-III (4 g, 19.6 mmol) and N-chlorosuccinimide (2.75 g, 20.6 mmol) in DMF (100 mL) was heated at 50° C. for 5 h and then poured into water. The resulting mixture was extracted with ethyl acetate (3×100 mL). The combined organic phases were washed with water and brine, dried over anhydrous sodium sulfate, and filtered. The filtrate was concentrated to afford m16-IV (3.64 g, y: 78%).

To a solution of m16-IV (2.38 g, 10 mmol) and pent-4-yn-1-ol (2.6 g, 30.9 mmol) in diethyl ether (66 mL) was added Na$_2$CO$_3$ (3.3 g, 31.1 mmol) in H$_2$O/chloroform (33 mL/30 mL) at 5° C. for 5 h. The aqueous phase was extracted with diethyl ether (3×50 mL). The combined organic phases were washed with brine, dried over anhydrous sodium sulfate, filtered, and concentrated. The residue thus obtained was purified by column chromatography on silica gel with (n-hexane:ethyl acetate=1:4) to afford m16-V (1.25 g, y: 44%).

A solution of m16-V (0.9 g, 3.1 mmol) and hydrazine monohydrate (0.2 g, 6 mmol) in MeOH/DCM (20 mL/20 mL) was stirred at 25° C. for 15 h and then filtrated. The filtrate was concentrated to afford moiety 16 (0.41 g, y: 84%).

Preparation of Moiety 17

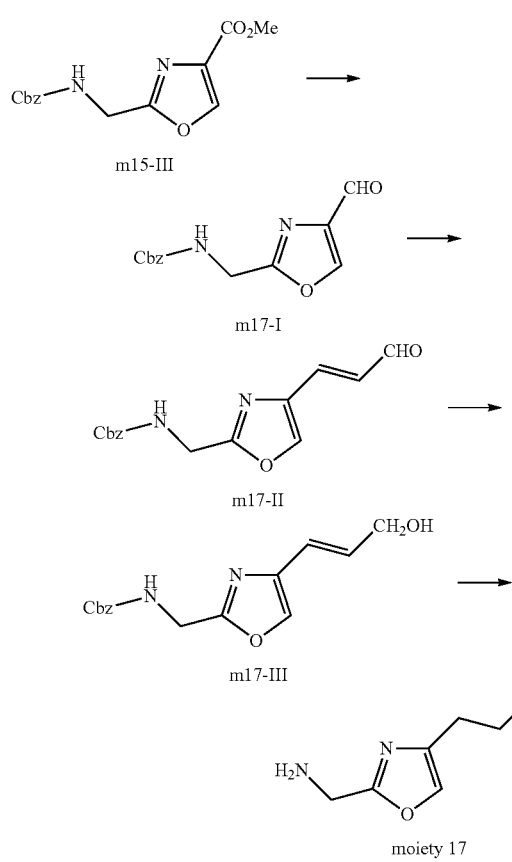

which was subjected to chromatography purification to give m17-I (5.31 g, y: 59% over two steps).

A solution of m17-I (3.63 g, 13.9 mmol), (1,3-Dioxolan-2-ylmethyl) triphenylphosphonium bromide (7.21 g, 16.8 mmol), and t-BuOK (1.92 g, 17.1 mmol) in THF (100 mL) was stirred at 5° C. for 2 h. To the resulting mixture was added HCl(aq) (50 mL, 2 N), stirred at 10-15° C. for 2 h, and then quenched with sat. NaHCO$_3$(aq). The mixture was extracted with ethyl acetate. The combined organic extracts were washed with brine, dried over anhydrous sodium sulfate, filtered, and concentrated. The residue was purified by flash column chromatography on silica gel with n-hexane/ethyl acetate (3:1) to afford product m17-II (3.54 g, y: 89%).

To a magnetically stirred solution of m17-II (3.54 g, 12.4 mmol) in dry MeOH (100 mL) were added a solution of NaBH$_4$ (0.69 g, 18.3 mmol) in MeOH (20 mL). The mixture was stirred at 10° C. for 1 h and then concentrated. The residue was dissolved in DCM (150 mL), washed with NH$_4$Cl, brine, dried over anhydrous sodium sulfate, filtered, and concentrated to afford m17-III (3.14 g, y: 88%).

A mixture of m17-III (3.14 g, 10.9 mmol) and 10% Pd/C (0.62 g) in iso-propanol (62 mL) was stirred under H$_2$(g) at 50° C. for 15 h. The resulting mixture was filtered, and the filtrate was concentrated to afford moiety 17 (1.53 g, y: 90%).

Example 2: Preparation of Compounds 1-148

Compounds 1-148 of this invention were prepared following the procedures provided below. Unless otherwise described above such as preparation of moiety compounds, all side chain compounds and other reagents are commercially available from various suppliers.

Preparation of Compound 1

The scheme below depicts synthesis of Compound 1.

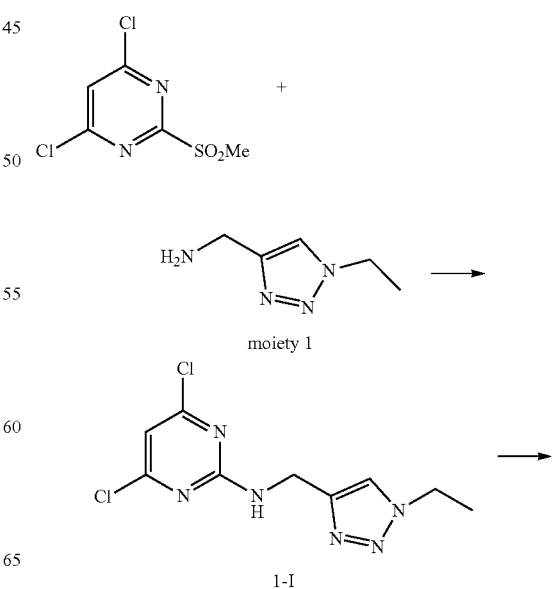

To a solution of m15-III (10.02 g, 34.5 mmol) in a mixture of EtOH (200 mL) and THF (100 mL) at 0-5° C. was added CaCl$_2$) (4.01 g, 36.1 mmol) and NaBH$_4$ (7.01 g, 185.3 mmol) in one portion. The resulting solution was then stirred at 30° C. for 2 h and quenched with sat. NH$_4$Cl(aq), followed by extraction with DCM (3×150 mL). The combined organic extracts were washed with brine, dried over anhydrous sodium sulfate and filtered. MnO$_2$ (36.31 g, 417.8 mmol) was added to the filtrate at 25° C. with agitation for 2 h. Filtration and concentration afforded crude product,

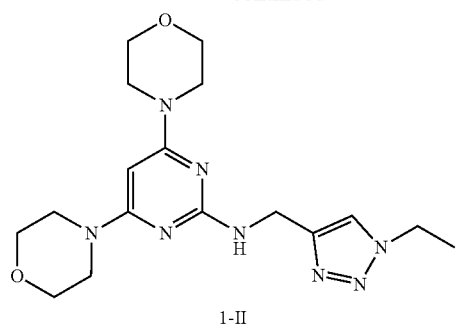

1-II

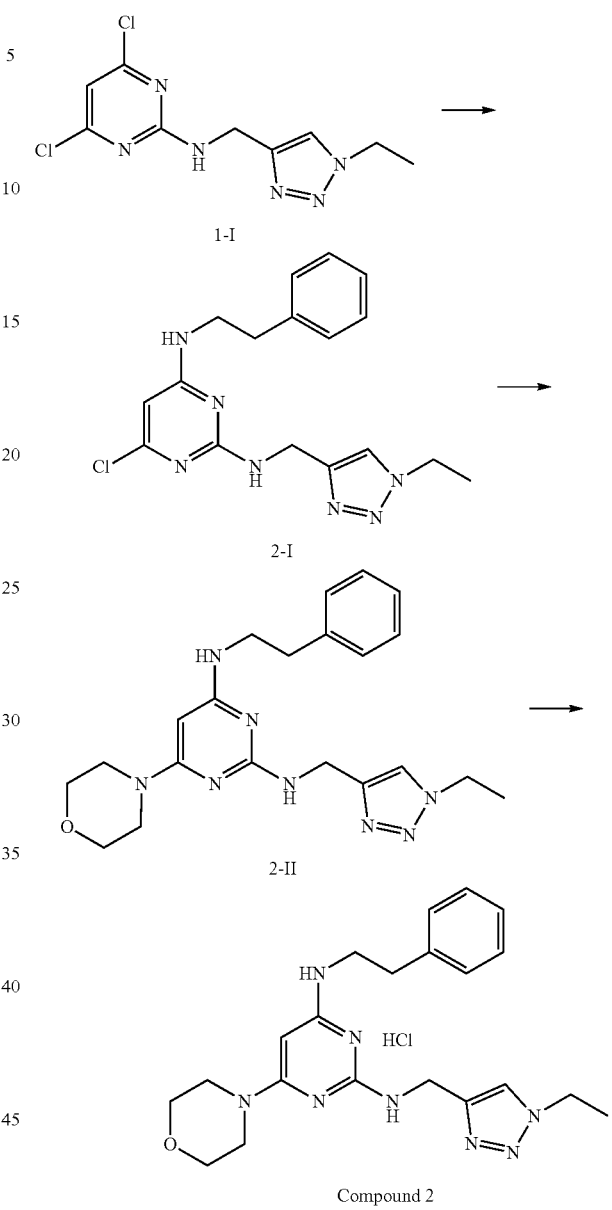

Preparation of Compound 2

To a solution of 4,6-dichloro-2-methanesulfonylpyrimidine (1.02 g, 4.5 mmol) in THF (50 mL) was added moiety 1 (0.85 g, 6.7 mmol) at −70° C. The mixture was stirred at 25° C. for 15 hours and then quenched with NH$_4$Cl(aq.) (50 mL, 2 M). The resulting solution was extracted with ethyl acetate (3×100 mL). The combined extracts were washed with brine, dried over anhydrous sodium sulfate, filtered, and concentrated. The residue thus obtained was purified by column chromatography on silica gel (n-hexane:ethyl acetate=2:1) to afford 1-I (0.81 g, y: 66%).

A solution of 1-I (0.81 g, 3 mmol) in isopropanol ("IPA", 4 mL) was mixed with morpholine (1.2 g, 13.8 mmol). The mixture was stirred at 140° C. for 4 h and then concentrated. The residue thus obtained was purified by column chromatography on silica gel (n-hexane:ethyl acetate=1:4) to afford 1-II (0.72 g, y: 65%).

A solution of 2N HCl/diethyl ether (2 mL, 4 mmol) was added to the solution of 1-II (360 mg, 1 mmol) in DCM (3.6 mL). The reaction mixture was stirred at 25° C. for 15 h and concentrated to afford a hydrochloride salt of Compound 1 (381 mg, y: 96%).

EI-MS: 375.2 (M+1).

Preparation of Compounds 97-98

Compounds 97-98 were prepared in a manner similar to that used to prepare Compound 1.

Compound 97 EI-MS: 376.2 (M+1). $^1$H-NMR (CDCl$_3$, 400 MHz, free form) δ 5.12 (s, 1H), 4.97 (d, 2H), 4.45 (q, 2H), 3.73 (m, 8H), 3.47 (m, 8H), 1.49 (t, 3H).

Compound 98 EI-MS: 376.2 (M+1). $^1$H-NMR (CDCl$_3$, 300 MHz, free form) δ 5.10 (s, 1H), 4.82 (d, 2H), 4.61 (q, 2H), 3.74 (m, 8H), 3.48 (m, 8H), 1.61 (t, 3H).

A solution of 1-I (1.27 g, 4.6 mmol) and phenethylamine (1.27 g, 10.5 mmol) in 1-pentanol (4 mL) was heated at 150° C. for 15 hours, after which the resulting mixture was concentrated. The residue thus obtained was purified by column chromatography with ethyl acetate to afford 2-I (1.1 g, y: 66%).

To a solution of 2-I (1.1 g, 3.1 mmol) in IPA (4 mL) was added morpholine (1.2 g, 13.8 mmol). The mixture was stirred at 140° C. for 15 h and then concentrated. The residue thus obtained was purified by column chromatography on silica gel (MeOH:ethyl acetate=1:9) to afford 2-II (0.98 g, y: 78%).

A solution of 2N HCl in diethyl ether (2 mL, 4 mmol) was added to a solution of 2-II (360 mg, 0.9 mmol) in DCM (3.6 mL). The reaction mixture was stirred at 25° C. for 15 h and concentrated to afford a hydrochloride salt of Compound 2 (341 mg, y: 87%).

EI-MS: 409.2 (M+1).

Preparation of Compound 3

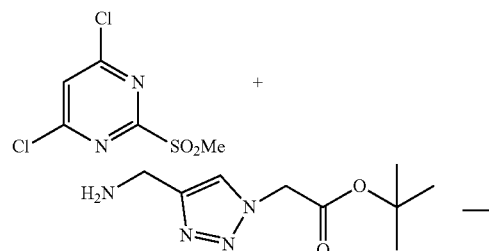

moiety 2

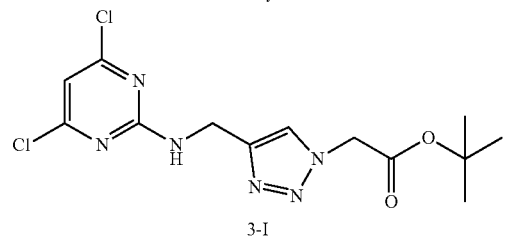

3-I

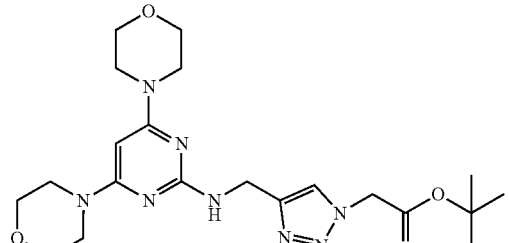

3-II

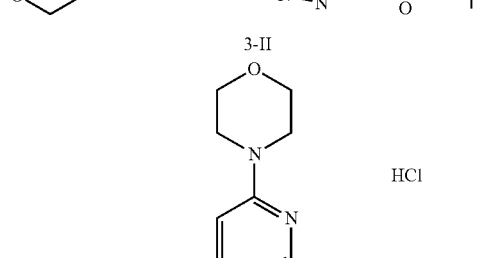

Compound 3

To a solution of 4,6-dichloro-2-methanesulfonylpyrimidine (1.02 g, 4.5 mmol) in THF (50 mL) was added moiety 2 (1.43 g, 6.7 mmol) at −70° C. The mixture was stirred at 25° C. for 15 h and then quenched with NH$_4$Cl(aq.) (50 mL, 2 M). The resulting solution was extracted with ethyl acetate (3×100 mL). The combined extracts were washed with brine, dried over anhydrous sodium sulfate, filtered, and concentrated. The residue thus obtained was purified by column chromatography on silica gel (n-hexane:ethyl acetate=2:1) to afford 3-I (0.91 g, y: 56%) as a solid.

To a solution of 3-I (0.91 g, 2.5 mmol) in IPA (4 mL) was added morpholine (1.1 g, 12.6 mmol). The mixture was stirred at 140° C. for 4 h and then concentrated. The residue thus obtained was purified by column chromatography on silica gel with ethyl acetate to afford 3-II (0.84 g, y: 72%).

A solution of 2N HCl in diethyl ether (2 mL, 4 mmol) was added to a DCM solution of 3-II (360 mg, 0.8 mmol). The reaction mixture was stirred at 25° C. for 15 h and then concentrated to afford a hydrochloride salt of Compound 3 (282 mg, y: 82%).

EI-MS: 405.2 (M+1).

Preparation of Compound 4

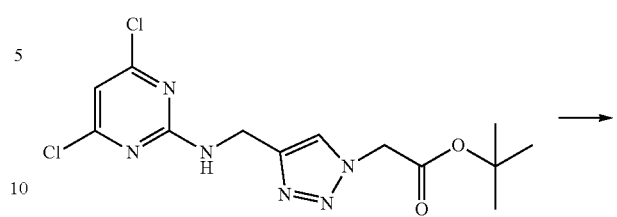

3-I

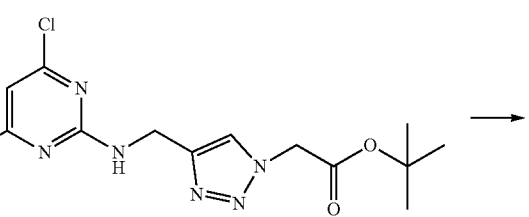

4-I

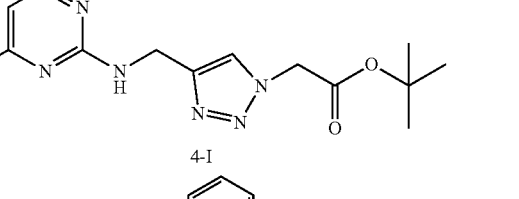

4-II

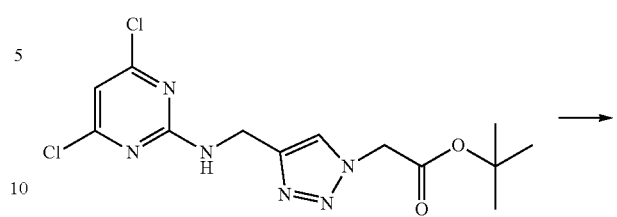

Compound 4

A solution of 3-I (1.02 g, 2.8 mmol) and phenethylamine (0.81 g, 6.6 mmol) in 1-pentanol (4 mL) was heated at 120° C. for 15 h. The resulting mixture was then concentrated. The residue thus obtained was purified by column chromatography with ethyl acetate to afford 4-I (0.85 g, y: 67%).

To a solution of 4-I (0.85 g, 1.9 mmol) in IPA (4 mL) was added morpholine (0.85 g, 9.8 mmol). The mixture was stirred at 140° C. for 15 h and then concentrated. The residue thus obtained was purified by column chromatography on silica gel (MeOH ethyl acetate=1:9) to afford 4-II (0.76 g, y: 80%).

A solution of 2N HCl in diethyl ether (1.5 mL, 3 mmol) was added to a DCM solution of 4-II (300 mg, 0.6 mmol). The reaction mixture was stirred at 25° C. for 15 h and then concentrated to afford a hydrochloride salt of Compound 4 (254 mg, y: 88%).

EI-MS: 439.2 (M+1).

Preparation of Compound 5

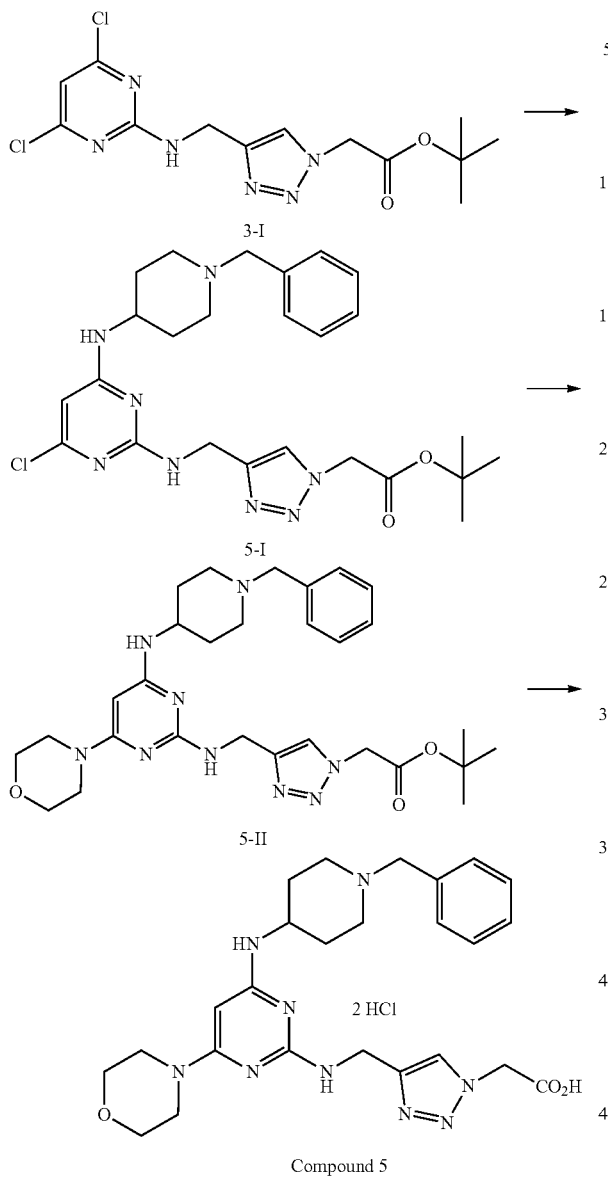

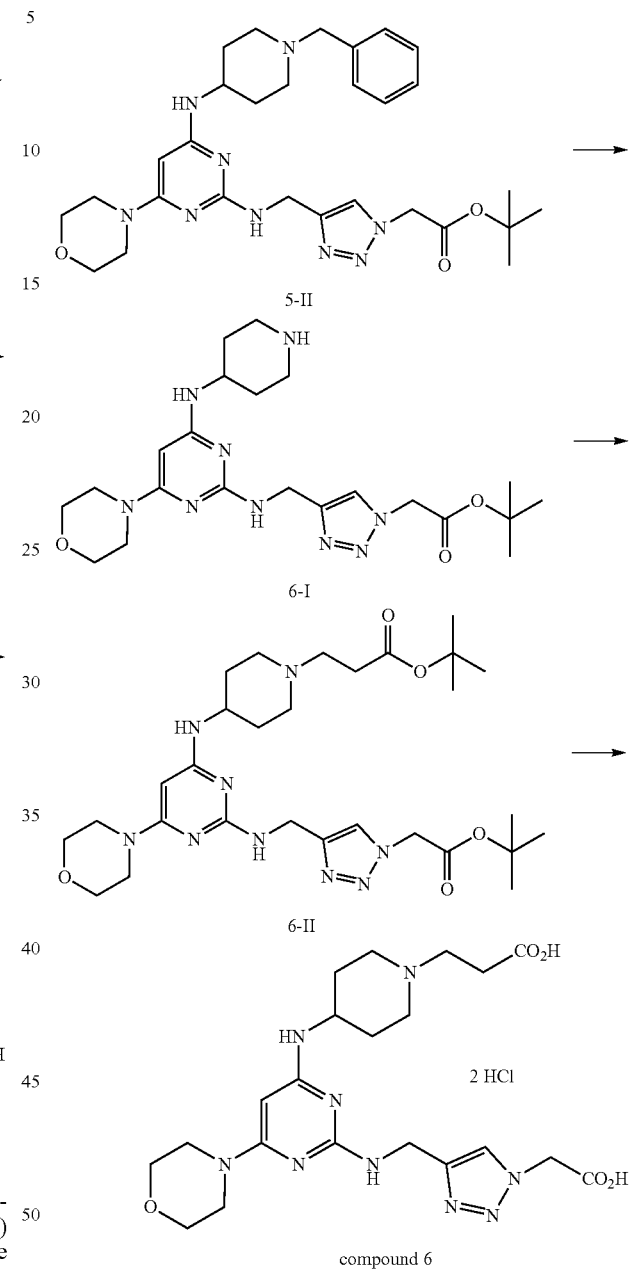

A solution of 3-I (1.02 g, 2.8 mmol) and 1-benzyl-piperidin-4-ylamine (1.06 g, 5.6 mmol) in 1-pentanol (4 mL) was heated at 120° C. for 15 hours. The resulting mixture was then concentrated. The residue thus obtained was purified by column chromatography with ethyl acetate to afford 5-I (0.96 g, y: 66%).

To a solution of 5-I (0.96 g, 1.9 mmol) in IPA (4 mL) was added morpholine (0.82 g, 9.4 mmol). The mixture was stirred at 140° C. for 15 h and then concentrated. The residue thus obtained was purified by column chromatography on silica gel (MeOH:ethyl acetate=1:9) to afford 5-II (0.81 g, y: 77%).

A solution of 2N HCl/diethyl ether (1 mL, 2 mmol) was added to a DCM solution of 5-II (304 mg, 0.5 mmol). The reaction mixture was stirred at 25° C. for 15 h and then concentrated to afford a hydrochloride salt of Compound 5 (268 mg, y: 86%).

EI-MS: 508.2 (M+1). $^1$H NMR (CD$_3$OD, 400 MHz) δ 8.17 (s, 1H), 7.62-7.58 (m, 2H), 7.53-7.50 (m, 3H), 5.36 (s, 2H), 4.75 (s, 2H), 4.38 (s, 2H), 4.01 (m, 1H), 3.78-3.70 (m, 8H), 3.64 (m, 2H), 3.26 (m, 2H), 2.24 (m, 2H), 1.88 (m, 2H).

Preparation of Compound 6

A solution of 5-II (1 g, 1.8 mmol) and 10% Pd/C (0.2 g) in 2-propanol (20 mL) was stirred under H$_2$(g) (1 atm) at 60° C. for 15 h. The resulting mixture was filtered.

The filtrate was concentrated to afford 6-I (0.75 g, y: 890%). $^1$H-NM/R (CDCl$_3$, 400 MHz) δ 7.58 (s, 1H), 5.00 (s, 2H), 4.94 (s, 1H), 4.69 (d, 2H), 3.74 (m, 4H), 3.62 (m, 1H), 3.47 (m, 4H), 3.07 (m, 2H), 2.70 (m, 2H), 1.96 (m, 2H), 1.47 (s, 9H), 1.34 (n, 2H).

A solution of 6-I (0.75 g, 1.6 mmol), acrylic acid tert-butyl ester (0.41 g, 3.2 mmol) and TEA (0.65 g, 6.4 mmol) in MeOH (18 mL) was stirred at 60° C. for 16 h and then concentrated. The residue thus obtained was purified on silica gel (MeOH:ethyl acetate=1:4) to afford 6-II (0.67 g, y: 70%).

A solution of 2N HCl in diethyl ether (1.5 mL, 3 mmol) was added to a DCM solution of 6-II (412 mg, 0.7 mmol). The reaction mixture was stirred at 25° C. for 15 h and then concentrated to afford a hydrochloride salt of Compound 6 (306 mg, y: 790).

EI-MS:490.2 (M+1).

Preparation of Compounds 99-104

Compounds 99-104 were prepared similarly as Compound 6.

Compound 99 EI-MS: 389.2 (M+1).

Compound 100 EI-MS: 475.3 (M+1). $^1$H-NMR (CDCl$_3$, 400 MHz, free form) δ 4.93 (s, 1H), 4.81 (d, 2H), 4.61 (q, 2H), 3.71 (m, 4H), 3.67 (s, 3H), 3.56 (m, 1H), 3.46 (m, 4H), 2.82 (m, 2H), 2.70 (t, 2H), 2.52 (t, 2H), 2.18 (m, 2H), 1.99 (m, 2H), 1.60 (t, 3H), 1.48 (in, 2H).

Compound 101 EI-MS: 461.2 (M+1).
Compound 102 EI-MS: 497.2 (M+1).
Compound 103 EI-MS: 568.2 (M+1).
Compound 104 EI-MS: 418.2 (M+1).

Preparation of Compound 7

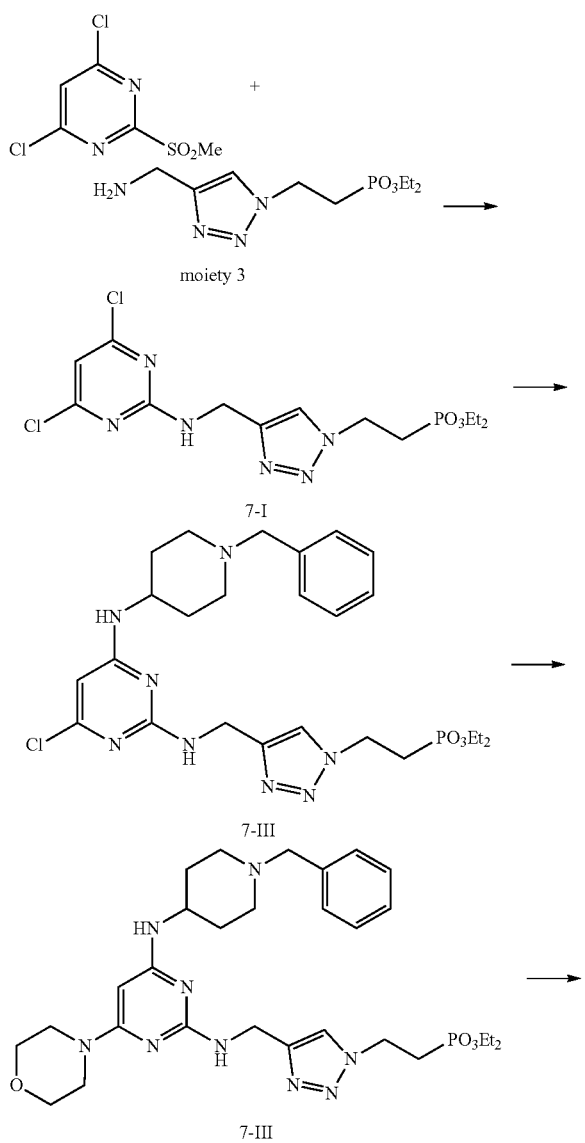

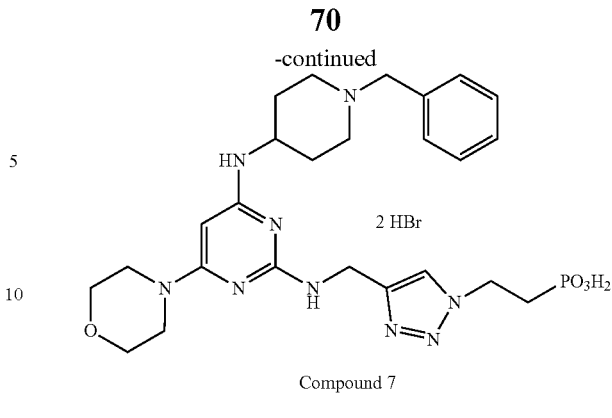

Compound 7

To a solution of 4,6-dichloro-2-methanesulfonylpyrimidine (2.04 g, 9 mmol) in THE (100 mL) was added moiety 3 (2.51 g, 9.6 mmol) at −70° C. The mixture was stirred at 25° C. for 15 hours and then quenched with NH$_4$Cl(aq.) (50 mL, 2 M). The resulting solution was extracted with ethyl acetate (3×100 mL). The combined extracts were washed with brine, dried over anhydrous sodium sulfate, filtered, and concentrated.

The residue thus obtained was purified by column chromatography on silica gel (MeOH:ethyl acetate=1:19) to afford 7-I (2.35 g, y: 64%).

A solution of 7-I (1.2 g, 2.9 mmol) and 1-benzyl-piperidin-4-ylamine (1.06 g, 5.6 mmol) in 1-pentanol (4 mL) was heated at 150° C. for 15 hours. The resulting mixture was concentrated. The residue thus obtained was purified by column chromatography on silica gel (MeOH:ethyl acetate=1:4) to afford 7-II (0.77 g, y: 47%).

To a solution of 7-II (0.77 g, 1.4 mmol) in IPA (4 mL) was added morpholine (0.7 g, 8 mmol). The mixture was stirred at 120° C. for 15 h and then concentrated. The residue thus obtained was purified by column chromatography on silica gel with ethyl acetate to afford 7-III (0.34 g, y: 41%).

To the solution of 7-III (340 mg, 0.6 mmol) in DCM (1.5 mL) was added bromotrimethylsilane ("TMSBr", 510 mg, 3.3 mmol). The reaction mixture was stirred at 25° C. for 4 h and then concentrated to afford a hydrobromide salt of Compound 7 (310 mg, y: 78%).

EI-MS: 558.2 (M+1).

Preparation of Compound 8

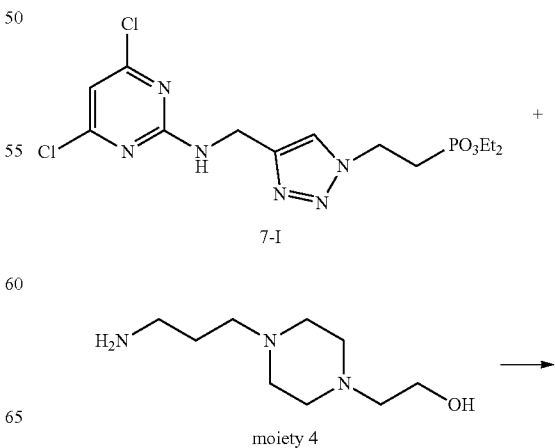

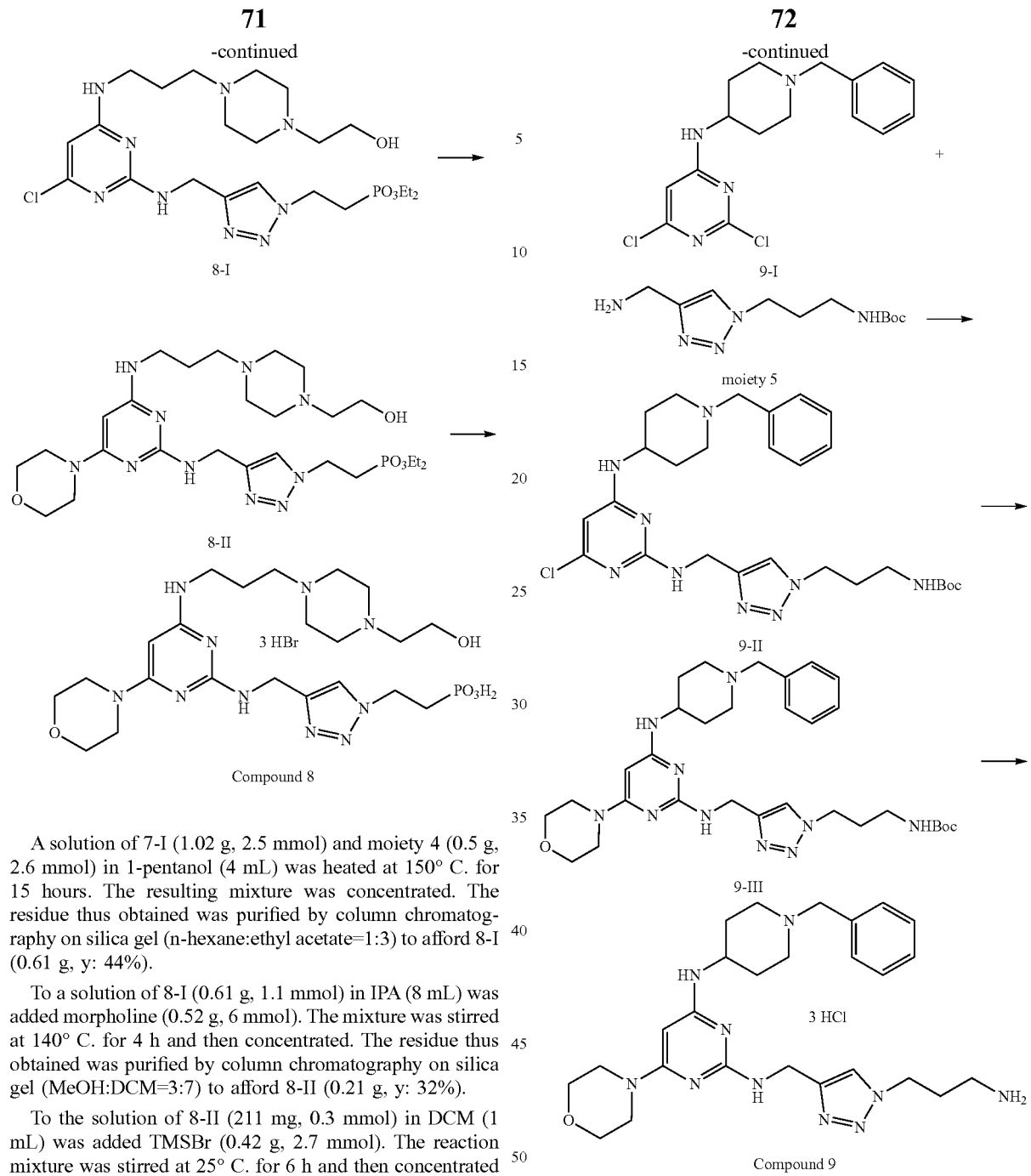

A solution of 7-I (1.02 g, 2.5 mmol) and moiety 4 (0.5 g, 2.6 mmol) in 1-pentanol (4 mL) was heated at 150° C. for 15 hours. The resulting mixture was concentrated. The residue thus obtained was purified by column chromatography on silica gel (n-hexane:ethyl acetate=1:3) to afford 8-I (0.61 g, y: 44%).

To a solution of 8-I (0.61 g, 1.1 mmol) in IPA (8 mL) was added morpholine (0.52 g, 6 mmol). The mixture was stirred at 140° C. for 4 h and then concentrated. The residue thus obtained was purified by column chromatography on silica gel (MeOH:DCM=3:7) to afford 8-II (0.21 g, y: 32%).

To the solution of 8-II (211 mg, 0.3 mmol) in DCM (1 mL) was added TMSBr (0.42 g, 2.7 mmol). The reaction mixture was stirred at 25° C. for 6 h and then concentrated to afford a hydrobromide salt of Compound 8 (242 mg, y: 80%).

EI-MS: 555.3 (M+1). $^1$H-NMR (CD$_3$OD, 400 MHz) δ 8.24 (s, 1H), 4.76-4.67 (m, 4H), 3.94 (m, 2H), 3.90 (m, 2H), 3.78-3.62 (m, 9H), 3.60-3.43 (m, 9H), 3.23 (m, 2H), 2.42 (m, 2H), 2.20 (m, 2H).

Preparation of Compound 9

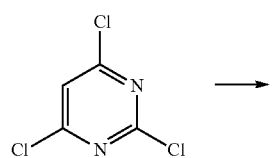

A solution of 2,4,6-trichloropyrimidine (1.83 g, 10 mmol) and 1-benzyl-piperidin-4-ylamine (2.71 g, 14.2 mmol) in THF (100 mL) was heated at 60° C. for 15 hours. The resulting mixture was concentrated. The residue thus obtained was purified by column chromatography (n-hexane:ethyl acetate=1:1) to afford 9-I (1.83 g, y: 54%).

To a solution of 9-I (1.83 g, 5.4 mmol) in 1-pentanol (4 mL) was added moiety 5 (1.41 g, 5.5 mmol). The mixture was stirred at 150° C. for 15 hours and then concentrated. The residue thus obtained was purified by column chromatography on silica gel with ethyl acetate to afford 9-II (2.01 g, y: 67%) as a solid.

To a solution of 9-II (2.01 g, 3.6 mmol) in IPA (4 mL) was added morpholine (1.42 g, 16.1 mmol). The mixture was stirred at 120° C. for 15 h and then concentrated.

The residue thus obtained was purified by column chromatography on silica gel (MeOH:ethyl acetate=1:19) to afford 9-III (1.58 g, y: 72%).

A solution of 2N HCl in diethyl ether (1.2 mL, 2.4 mmol) was added to a DCM solution of 9-III (350 mg, 0.6 mmol). The reaction mixture was stirred at 25° C. for 15 h and then concentrated to afford a hydrochloride salt of Compound 9 (325 mg, y: 91%).

EI-MS: 507.3 (M+1). $^1$H-NMR (D$_2$O, 300 MHz) δ 7.87 (s, 1H), 7.42-7.30 (m, 5H), 4.53 (s, 2H), 4.39 (t, 2H), 4.20 (s, 2H), 3.70 (m, 1H), 3.62 (m, 4H), 3.48-3.44 (m, 6H), 3.02 (m, 2H), 2.87 (m, 2H), 2.20-2.04 (m, 4H), 1.60 (m, 2H).

Preparation of Compound 17

Compound 17 was prepared in a manner similar to that used to prepare Compound 9.

EI-MS: 549.3 (M+1).

Preparation of Compound 10

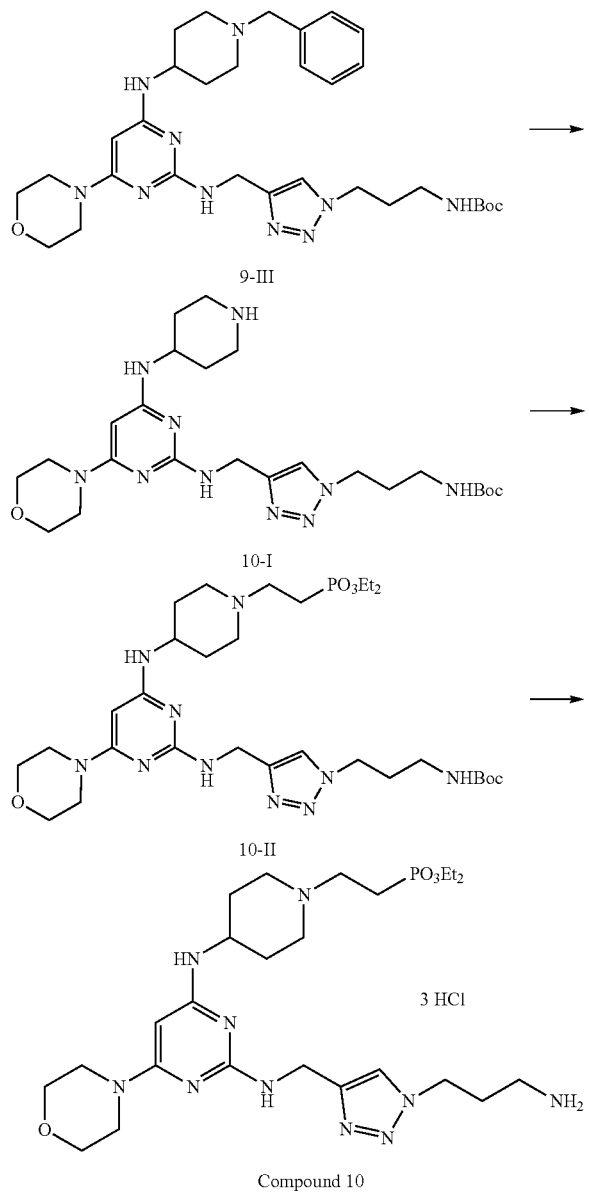

A solution of 9-III (1 g, 1.6 mmol) and 10% Pd/C (0.3 g) in 2-propanol (20 mL) was stirred under H$_2$(g) (1 atm) at 60° C. for 15 h. The resulting mixture was filtered and concentrated to afford 10-I (0.74 g, y: 87%).

A solution of 10-I (0.74 g, 1.4 mmol), diethyl vinylphosphonate (0.41 g, 2.5 mmol) and TEA (3 drops) in MeOH (18 mL) was stirred at 60° C. for 16 h and then concentrated. The residue thus obtained was purified by column chromatography on silica gel (MeOH:ethyl acetate=1:9) to afford 10-II (0.63 g, y: 65%).

A solution of 2N HCl in diethyl ether (1 mL, 2 mmol) was added to a DCM solution of 10-II (330 mg, 0.5 mmol). The reaction mixture was stirred at 25° C. for 15 h and then concentrated to afford a hydrochloride salt of Compound 10 (305 mg, y: 91%).

EI-MS: 581.3 (M+1).

Preparation of Compounds 18-19, 36, 109, 122, 125, 131, 132, and 145

Compounds 18-19, 36, 109, 122, 125, 131, 132, and 145 were prepared in a manner similar to that used to prepare Compound 10.

Compound 18 EI-MS: 459.3 (M+1).

Compound 19 EI-MS: 531.3 (M+1).

Compound 36 EI-MS: 567.3 (M+1). $^1$H-NMR (D$_2$O, 400 MHz) δ 7.88 (s, 1H), 4.53 (d, 2H), 4.37 (t, 2H), 3.75 (m, 1H), 3.61-3.40 (m, 10H), 3.28 (m, 2H), 3.05-3.00 (m, 4H), 2.20-1.90 (m, 6H), 1.62 (m, 2H).

Compound 109 EI-MS: 651.3 (M+1).

Compound 122 EI-MS: 651.4 (M+1). $^1$H-NMR (CD$_3$OD, 400 MHz, free form) δ 7.75 (s, 1H), 4.55 (s, 2H), 4.42 (t, 2H), 4.13 (q, 4H), 3.68-3.62 (m, 9H), 3.40 (m, 4H), 2.88 (m, 2H), 2.64 (m, 2H), 2.34 (m, 4H), 2.28-2.15 (m, 4H), 2.10-2.02 (m, 4H), 1.93 (m, 2H), 1.51 (m, 2H), 1.35 (t, 6H).

Compound 125 EI-MS: 699.3 (M+1). $^1$H-NMR (CD$_3$OD, 400 MHz, free form) δ 7.77 (s, 1H), 4.58 (s, 2H), 4.46 (t, 2H), 4.15 (q, 4H), 3.73-3.70 (m, 5H), 3.42 (m, 4H), 3.02 (m, 4H), 2.88 (m, 2H), 2.82 (m, 4H), 2.66 (m, 2H), 2.33 (t, 2H), 2.24 (m, 2H), 2.16-2.04 (m, 4H), 1.91 (m, 2H), 1.51 (m, 2H), 1.35 (t, 6H).

Compound 131 EI-MS: 595.3 (M+1). $^1$H-NMR (CD$_3$OD, 400 MHz, free form) δ 7.80 (s, 1H), 4.58 (s, 2H), 4.49 (t, 2H), 4.13 (q, 4H), 3.71 (m, 1H), 3.57-3.53 (m, 6H), 2.92 (m, 2H), 2.70 (m, 2H), 2.53 (m, 4H), 2.37 (s, 3H), 2.26 (m, 2H), 2.14-2.08 (m, 4H), 1.95 (m, 2H), 1.52 (m, 2H), 1.37 (t, 6H).

Compound 132 EI-MS: 639.4 (M+1). $^1$H-NMR (CD$_3$OD, 400 MHz, free form) δ 7.81 (s, 1H), 4.57 (s, 2H), 4.46 (t, 2H), 4.16 (q, 4H), 3.70 (m, 1H), 3.60 (t, 2H), 3.53 (m, 4H), 3.36 (s, 3H), 3.30 (t, 2H), 3.21 (m, 4H), 3.00 (m, 2H), 2.75 (m, 2H), 2.64 (m, 2H), 2.33 (m, 2H), 2.10-2.02 (m, 6H), 1.53 (m, 2H), 1.31 (t, 6H).

Compound 145 EI-MS: 747.3 (M+1).

Preparation of Compound 11

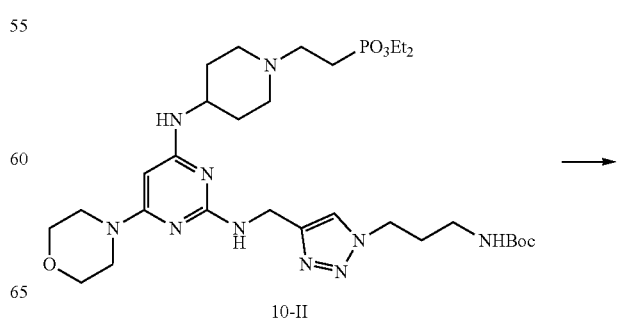

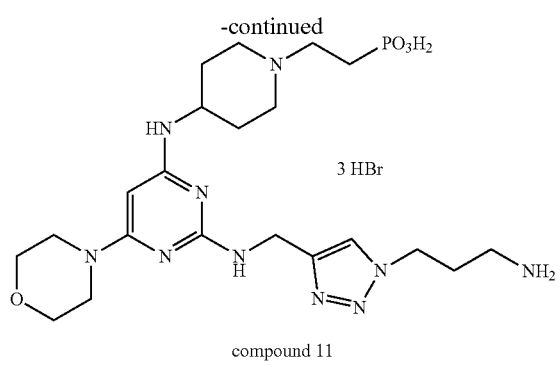

compound 11

To a solution of 10-II (302 mg, 0.4 mmol) in DCM (1 mL) was added TMSBr (0.40 g, 2.6 mmol). The reaction mixture was stirred at 25° C. for 5 h and then concentrated to afford a hydrobromide salt of Compound 11 (263 mg, y: 77%).

EI-MS: 525.3 (M+1). $^1$H-NMR (D$_2$O, 400 MHz) δ 7.92 (s, 1H), 4.53 (s, 2H), 4.40 (t, 2H), 3.78 (m, 1H), 3.58 (m, 4H), 3.54 (m, 2H), 3.48 (m, 4H), 3.23 (m, 2H), 3.00 (m, 2H), 2.87 (t, 2H), 2.13 (m, 2H), 2.09-1.97 (m, 4H), 1.61 (m, 2H).

Preparation of Compound 12

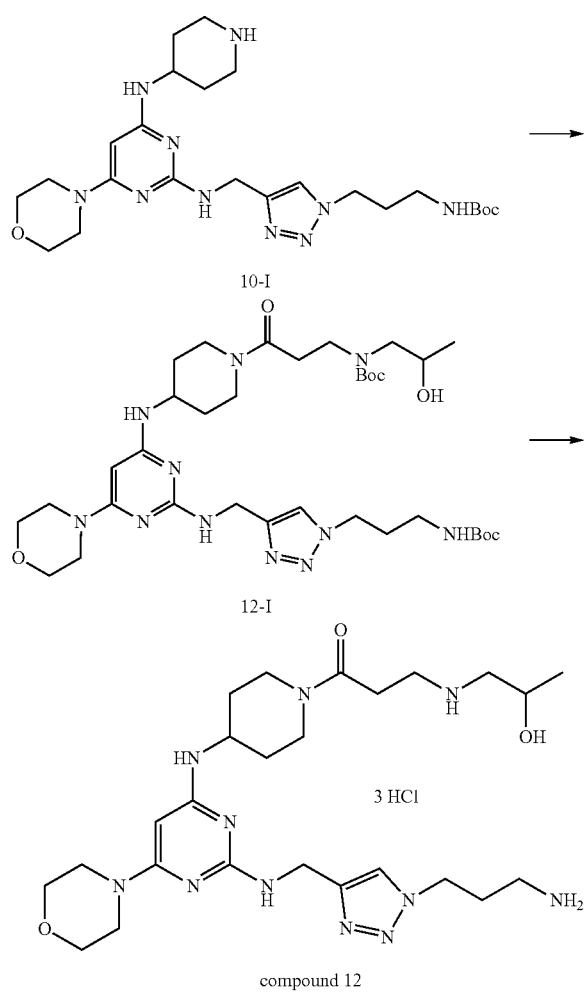

To a solution of 10-I (0.61 g, 1.2 mmol) in DCM (25 mL) was added 1-ethyl-3-(3-dimethylaminopropyl)-carbodiimide ("EDCI", 0.35 g, 1.8 mmol), hydroxybenzotriazole ("HOBt", 0.28 g, 1.8 mmol) and 3-[tert-butoxycarbonyl-(2-hydroxy-propyl)-amino]-propionic acid (0.42 g, 1.7 mmol) at 25° C. The reaction mixture was stirred for 15 h and then poured into water. The resulting mixture was extracted with DCM. The combined organic extracts were washed with brine, dried over anhydrous sodium sulfate, filtered, and concentrated. The residue thus obtained was purified by column chromatography on silica gel (MeOH:DCM=1:19) to afford 12-I (0.55 g, y: 62%).

A solution of 2N HCl/diethyl ether (0.75 mL, 1.5 mmol) was added to a DCM solution of 12-I (300 mg, 0.4 mmol). The reaction mixture was stirred at 25° C. for 15 h and then concentrated to afford a hydrochloride salt of Compound 12 (240 mg, y: 91%).

EI-MS: 546.3 (M+1). $^1$H-NMR (D$_2$O, 300 MHz) δ 7.83 (s, 1H), 4.51 (s, 2H), 4.37 (t, 2H), 4.13 (m, 1H), 3.97 (m, 1H), 3.78-3.57 (m, 6H), 3.43 (m, 4H), 3.30-3.02 (m, 4H), 2.90-2.67 (m, 6H), 2.16 (m, 2H), 1.93 (m, 2H), 1.38 (m, 2H), 1.06 (d, 3H).

Preparation of Compounds 13-15, 23-26, 33-34, 73-74, and 77-80

Compounds 13-15, 23-26, 33-34, 73-74, and 77-80 were prepared following a procedure similar to that used to prepare Compound 12.

Compounds 13 EI-MS: 567.3 (M+1). $^1$H-NMR (D$_2$O, 400 MHz) δ 7.85 (s, 1H), 6.78-6.70 (m, 3H), 4.47 (s, 2H), 4.36 (t, 2H), 4.15 (m, 1H), 3.66 (s, 3H), 3.65-3.36 (m, 10H), 3.06 (m, 1H), 2.87-2.83 (m, 3H), 2.14 (m, 2H), 1.89 (m, 1H), 1.70 (m, 1H), 1.37 (m, 2H).

Compound 14 EI-MS: 577.3 (M+1).

Compound 15 EI-MS: 662.3 (M+1). $^1$H-NMR (D$_2$O, 300 MHz) δ 7.90 (s, 1H), 4.52 (s, 2H), 4.40 (t, 2H), 4.16-4.04 (m, 2H), 3.95 (m, 1H), 3.77 (m, 1H), 3.65-3.55 (m, 5H), 3.47-3.30 (m, 7H), 3.16 (m, 1H), 2.86 (m, 2H), 2.78 (m, 1H), 2.60 (m, 2H), 2.14 (m, 2H), 1.93-1.70 (m, 6H), 1.40 (m, 1H), 1.26 (m, 1H).

Compound 23 EI-MS: 806.4 (M+1). $^1$H-NMR (CD$_3$OD, 400 MHz, free form) δ 7.80 (s, 1H), 4.57 (s, 2H), 4.43-4.39 (m, 4H), 4.16-4.13 (m, 2H), 4.00 (m, 1H), 3.85 (m, 1H), 3.73-3.64 (m, 5H), 3.61 (m, 2H), 3.50-3.30 (m, 9H), 3.16 (m, 1H), 2.84 (m, 1H), 2.62 (m, 2H), 2.14 (m, 2H), 1.99-1.86 (m, 6H), 1.43-1.40 (m, 11H).

Compound 24 EI-MS: 706.3 (M+1). $^1$H-NMR (D$_2$O, 400 MHz) δ 7.86 (s, 1H), 4.52 (s, 2H), 4.41-4.38 (m, 4H), 4.06-4.04 (m, 2H), 3.88 (m, 1H), 3.81-3.78 (m, 2H), 3.62-3.60 (m, 4H), 3.60 (m, 2H), 3.50-3.30 (m, 6H), 3.10-2.96 (m, 4H), 2.78 (m, 1H), 2.58 (m, 2H), 2.20 (m, 2H), 1.90-1.64 (m, 6H), 1.41 (m, 2H).

Compound 25 EI-MS: 762.4 (M+1). $^1$H-NMR (CD$_3$OD, 300 MHz, free form) δ 7.84 (s, 1H), 4.59 (s, 2H), 4.39 (t, 2H), 4.16 (m, 1H), 3.98 (m, 1H), 3.84 (m, 1H), 3.71-3.68 (m, 5H), 3.50-3.40 (m, 6H), 3.22 (m, 1H), 3.03 (t, 2H), 2.82 (m, 1H), 2.62 (t, 2H), 2.04-1.86 (m, 10H), 1.42 (s, 9H), 1.38 (m, 2H).

Compound 26 EI-MS: 691.4 (M+1).

Compound 33 EI-MS: 675.4 (M+1). $^1$H-NMR (D$_2$O, 400 MHz, free form) δ 7.84 (s, 1H), 4.50 (s, 2H), 4.29 (t, 2H), 4.10 (m, 1H), 3.98-3.95 (m, 2H), 3.78-3.65 (m, 2H), 3.57 (m, 4H), 3.42 (m, 4H), 3.23-3.10 (m, 5H), 3.06-2.96 (m, 4H), 2.86-2.77 (m, 5H), 2.55 (t, 2H), 2.00-1.73 (m, 4H), 1.41 (m, 1H), 1.34 (m, 1H), 1.08-1.06 (m, 6H).

Compound 34 EI-MS: 791.4 (M+1).

Compound 73 EI-MS: 646.3 (M+1).

Compound 74 EI-MS: 661.3 (M+1). $^1$H-NMR (CD$_3$OD, 400 MHz, free form) δ 7.79 (s, 1H), 4.60 (s, 2H), 4.45-4.40 (m, 3H), 4.18 (q, 2H), 4.00 (s, 2H), 3.98 (m, 1H), 3.81-3.75

(m, 5H), 3.68 (s, 3H), 3.57-3.52 (m, 4H), 3.20 (m, 1H), 3.06 (m, 4H), 2.79-2.61 (m, 5H), 2.48 (t, 2H), 2.10-1.83 (m, 6H), 1.21 (t, 3H).

Compound 77 EI-MS: 792.4 (M+1). $^1$H-NMR (CD$_3$OD, 400 MHz, free form) δ 7.86 (s, 1H), 4.60 (s, 2H), 4.54 (t, 2H), 4.39 (m, 1H), 4.10 (m, 1H), 3.95 (m, 1H), 3.86 (m, 1H), 3.81 (t, 2H), 3.68-3.62 (m, 5H), 3.56-3.40 (m, 7H), 3.22 (m, 1H), 3.13 (t, 2H), 2.84 (m, 1H), 2.62 (t, 2H), 1.98-1.83 (m, 8H), 1.42 (s, 9H), 1.38 (m, 2H).

Compound 78 EI-MS: 692.3 (M+1). $^1$H-NMR (D$_2$O, 400 MHz) δ 7.86 (s, 1H), 4.53-4.46 (m, 4H), 4.16-4.05 (m, 2H), 3.95 (m, 1H), 3.81-3.77 (m, 3H), 3.65-3.54 (m, 5H), 3.48-3.30 (m, 7H), 3.15 (m, 1H), 3.01 (m, 2H), 2.80 (m, 1H), 2.56 (m, 2H), 1.93-1.70 (m, 8H), 1.40 (m, 1H), 1.26 (m, 1H).

Compound 79 EI-MS: 584.3 (M+1). $^1$H-NMR (CDCl$_3$, 300 MHz, free form) δ 7.46 (s, 1H), 7.32-7.22 (m, 7H), 6.97 (t, 1H), 6.86 (t, 2H), 4.92 (s, 1H), 4.65 (d, 2H), 4.52 (t, 2H), 3.97-3.92 (m, 3H), 3.72 (m, 4H), 3.51 (s, 2H), 3.44 (m, 4H), 2.82 (m, 2H), 2.36 (m, 2H), 2.15 (m, 2H), 1.96 (m, 2H), 1.48 (m, 2H).

Compound 80 EI-MS: 566.3 (M+1).

Preparation of Compound 16

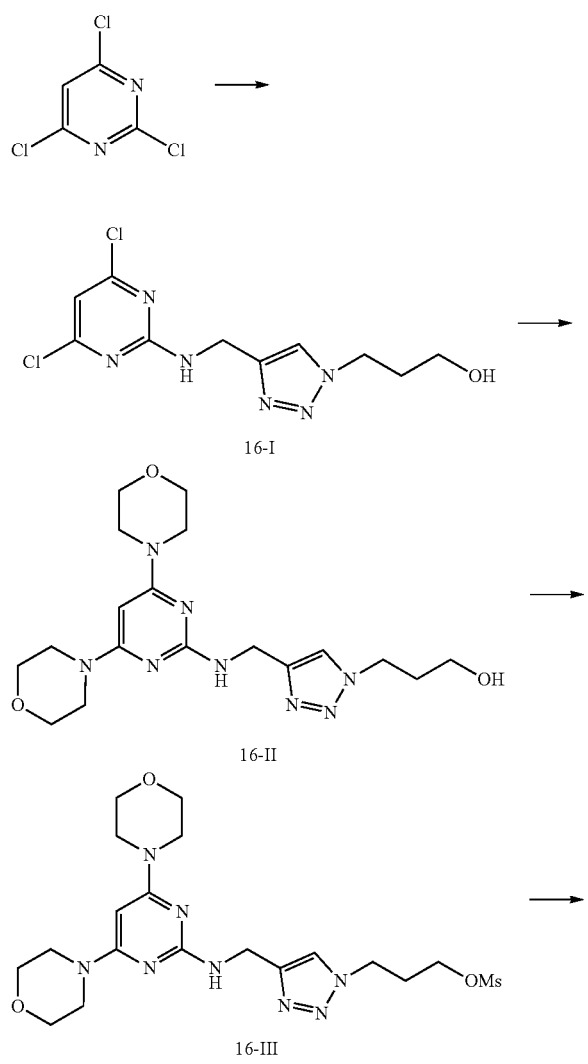

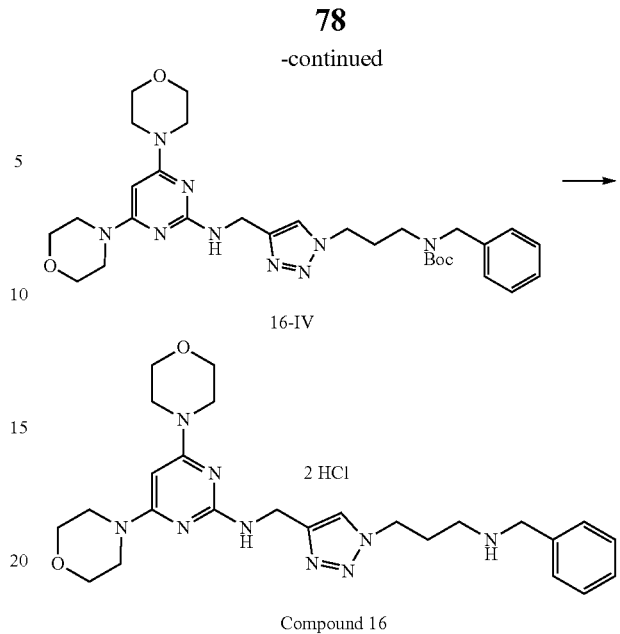

Compound 16

To a solution of 2,4,6-trichloropyrimidine (1.83 g, 10 mmol) in THF (54 mL) was added moiety 6 (2.41 g, 15.4 mmol) and TEA (2 g, 19.8 mmol). The mixture was stirred at 25° C. for 15 h and then quenched with NH$_4$Cl(aq.) (50 mL, 2 M). The resulting solution was extracted with ethyl acetate (3×100 mL). The combined extracts were washed with brine, dried over anhydrous sodium sulfate, filtered, and then concentrated. The residue thus obtained was purified by column chromatography on silica gel (n-hexane:ethyl acetate=1:3) to afford 16-I (1.03 g, y: 34%).

To a solution of 16-I (1.03 g, 3.4 mmol) in IPA (10 mL) was added morpholine (1.4 g, 16.1 mmol). The mixture was stirred at 120° C. for 15 h and then concentrated. The residue thus obtained was purified by column chromatography on silica gel (n-hexane:ethyl acetate=1:9) to afford 16-II (1.2 g, y: 87%).

To a solution of 16-II (1.2 g, 3 mmol) in dry DCM (40 mL) were added TEA (0.45 g, 4.5 mmol) and MsCl (0.45 g, 3.9 mmol) at 5° C. The reaction mixture was stirred at room temperature for 15 h and then quenched with NH$_4$Cl(aq.) (50 mL, 2M). The resulting residue was extracted with DCM. The combined extracts were washed with water and brine, dried over anhydrous sodium sulfate, and filtered. The filtrate was concentrated to afford 16-III (1.04 g, y: 73%).

To a solution of 16-III (1.04 g, 2.2 mmol) in dry THF (30 mL) was added benzylamine (0.28 g, 2.6 mmol) at 5° C. The reaction mixture was stirred at room temperature for 15 h and then quenched with NH$_4$Cl(aq.) (50 mL, 2 M). The resulting residue was extracted with ethyl acetate. The combined extracts were washed with water and brine, dried over anhydrous sodium sulfate, filtered, and concentrated. To the residue thus obtained were added DCM (50 mL), Boc$_2$O (0.65 g, 3 mmol), and TEA (0.41 g, 4.1 mmol). The mixture was stirred at room temperature for 15 h and then concentrated to obtain a crude residue, which was purified by column chromatography on silica gel (n-hexane:ethyl acetate=1:3) to afford 16-IV (0.56 g, y: 44%).

A solution of 2N HCl/diethyl ether (2 mL, 4 mmol) was added to a DCM solution of 16-IV (562 mg, 0.9 mmol). The reaction mixture was stirred at 25° C. for 15 h and then concentrated to afford a hydrochloride salt of Compound 16 (451 mg, y: 84%).

EI-MS: 494.3 (M+1). ¹H-NMR (D₂O, 400 MHz) δ 7.83 (s, 1H), 7.30-7.15 (m, 5H), 4.50 (s, 2H), 4.37 (t, 2H), 3.97 (s, 2H), 3.70-3.57 (m, 8H), 3.40 (m, 8H), 2.84 (m, 2H), 2.15 (m, 2H).

Preparation of Compounds 21-22 and 50-52

Compounds 21-22 and 50-52 were prepared in a manner similar to that used to prepare Compound 16.

Compound 21 EI-MS: 655.4 (M+1). ¹H-NMR (D₂O, 400 MHz) δ 7.87 (s, 1H), 7.83 (s, 1H), 7.49 (m, 1H), 7.40-7.35 (m, 6H), 4.49 (s, 2H), 4.38 (t, 2H), 4.21 (s, 2H), 4.08 (s, 2H), 3.80 (s, 3H), 3.68 (m, 1H), 3.60 (m, 4H), 3.53-3.40 (m, 6H), 3.02 (m, 2H), 2.88 (m, 2H), 2.22-2.06 (m, 4H), 1.58 (m, 2H).

Compound 22 EI-MS: 565.3 (M+1).

Compound 50 EI-MS: 405.2 (M+1). ¹H-NMR (CDCl₃, 400 MHz, free form) δ 7.45 (s, 1H), 5.07 (s, 1H), 4.62 (d, 2H), 4.41 (t, 2H), 3.69 (m, 8H), 3.54 (t, 2H), 3.44 (m, 8H), 2.03 (m, 2H).

Compound 51 EI-MS: 693.3 (M+1).

Compound 52 EI-MS: 433.2 (M+1). ¹H-NMR (CDCl₃, 400 MHz, free form) δ 7.41 (s, 1H), 5.08 (s, 1H), 4.63 (d, 2H), 4.27 (t, 2H), 3.70 (m, 8H), 3.58 (t, 2H), 3.45 (m, 8H), 1.87 (m, 2H), 1.54 (m, 2H), 1.35 (m, 2H).

Preparation of Compound 20

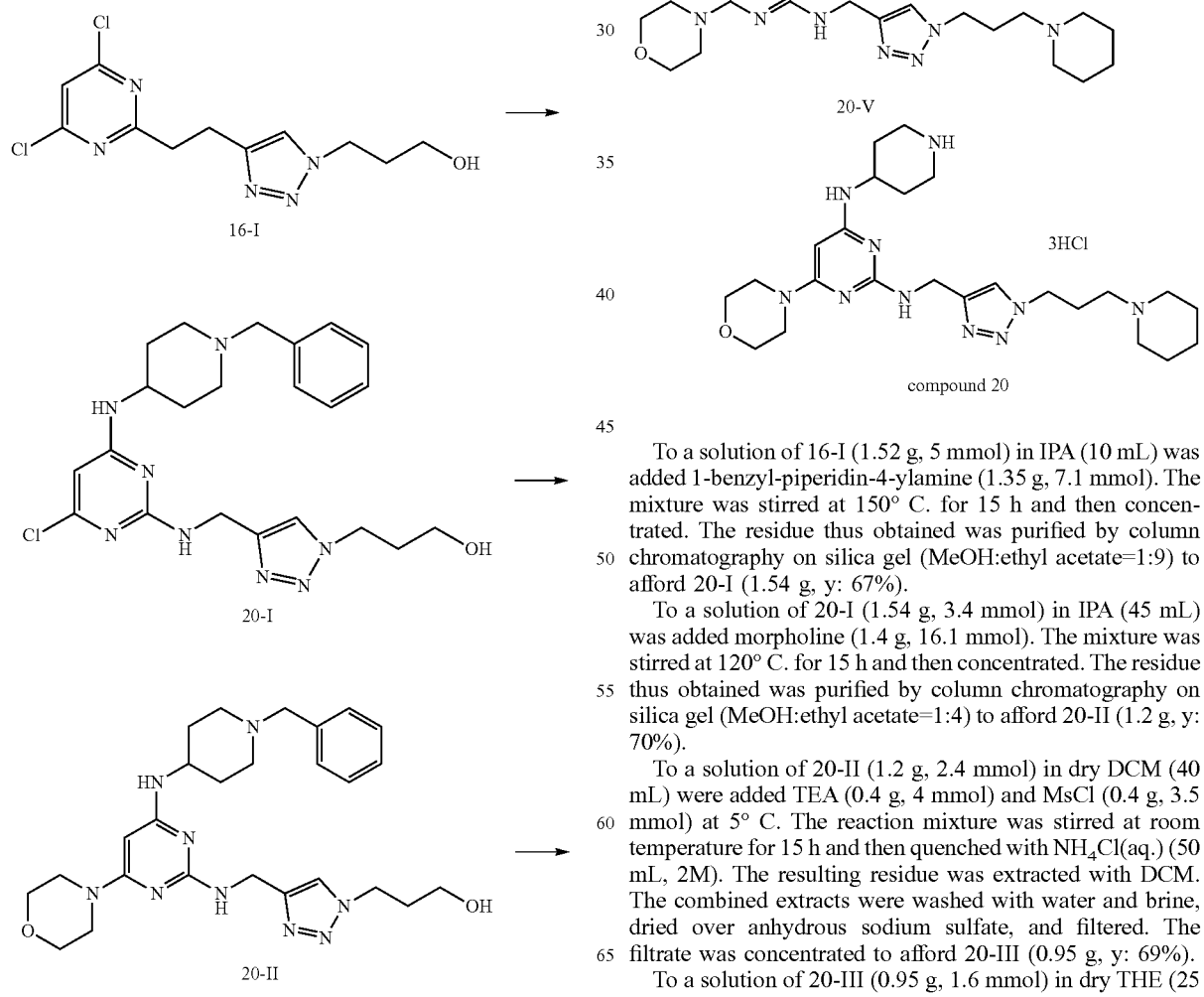

To a solution of 16-I (1.52 g, 5 mmol) in IPA (10 mL) was added 1-benzyl-piperidin-4-ylamine (1.35 g, 7.1 mmol). The mixture was stirred at 150° C. for 15 h and then concentrated. The residue thus obtained was purified by column chromatography on silica gel (MeOH:ethyl acetate=1:9) to afford 20-I (1.54 g, y: 67%).

To a solution of 20-I (1.54 g, 3.4 mmol) in IPA (45 mL) was added morpholine (1.4 g, 16.1 mmol). The mixture was stirred at 120° C. for 15 h and then concentrated. The residue thus obtained was purified by column chromatography on silica gel (MeOH:ethyl acetate=1:4) to afford 20-II (1.2 g, y: 70%).

To a solution of 20-II (1.2 g, 2.4 mmol) in dry DCM (40 mL) were added TEA (0.4 g, 4 mmol) and MsCl (0.4 g, 3.5 mmol) at 5° C. The reaction mixture was stirred at room temperature for 15 h and then quenched with NH₄Cl(aq.) (50 mL, 2M). The resulting residue was extracted with DCM. The combined extracts were washed with water and brine, dried over anhydrous sodium sulfate, and filtered. The filtrate was concentrated to afford 20-III (0.95 g, y: 69%).

To a solution of 20-III (0.95 g, 1.6 mmol) in dry THF (25 mL) was added piperidine (0.28 g, 3.3 mmol) at 5° C. The reaction mixture was stirred at room temperature for 15 h and quenched with NH₄Cl(aq.) (50 mL, 2 M). The resulting residue was extracted with ethyl acetate. The combined extracts were washed with water and brine, dried over anhydrous sodium sulfate, filtered, and concentrated. The residue was purified by column chromatography on silica gel (MeOH:ethyl acetate=1:1) to afford 20-IV (0.56 g, y: 60%).

A solution of 20-IV (0.56 g, 1 mmol) and 10% Pd/C (0.17 g) in 2-propanol (2 mL) was stirred under H₂(g) (1 atm) at 60° C. for 15 h. The resulting mixture was filtered. The filtrate was concentrated to afford 20-V (0.42 g, y: 89%).

A solution of 2N HCl in diethyl ether (1.2 mL, 2.4 mmol) was added to a DCM solution of 20-V (310 mg, 0.6 mmol). The reaction mixture was stirred at 25° C. for 15 h and then concentrated to afford a hydrochloride salt of Compound 20 (359 mg, y: 95%).

EI-MS: 485.3 (M+1).

Preparation of Compounds 120, 121, 124, 127, and 144

Compounds 120, 121, 124, 127, and 144 were prepared in a manner similar to that used to prepare Compound 20.

Compound 120 EI-MS: 665.4 (M+1).

Compound 121 EI-MS: 577.3 (M+1). ¹H NMR (CD₃OD, 400 MHz, free form) δ 7.75 (s, 1H), 7.35-7.28 (m, 5H), 4.55 (s, 2H), 4.41 (t, 2H), 3.75-3.62 (m, 11H), 3.40 (m, 4H), 2.89 (m, 2H), 2.34 (m, 4H), 2.29 (m, 2H), 2.24 (m, 2H), 2.06 (m, 2H), 1.94 (m, 2H), 1.52 (m, 2H).

Compound 124 EI-MS: 625.3 (M+1).

Compound 127 EI-MS: 725.4 (M+1). ¹H NMR (CDCl₃, 400 MHz, free form) δ 7.55 (s, 1H), 4.96 (s, 1H), 4.71 (d, 2H), 4.32 (t, 2H), 4.11 (q, 4H), 3.75-3.70 (m, 6H), 3.56-3.50 (m, 5H), 3.31 (m, 4H), 2.82 (m, 2H), 2.65 (m, 2H), 2.16-2.12 (m, 4H), 2.05-1.96 (m, 4H), 1.50 (m, 2H), 1.46 (s, 9H), 1.31 (t, 6H).

Compound 144 EI-MS: 673.3 (M+1).

Preparation of Compound 27

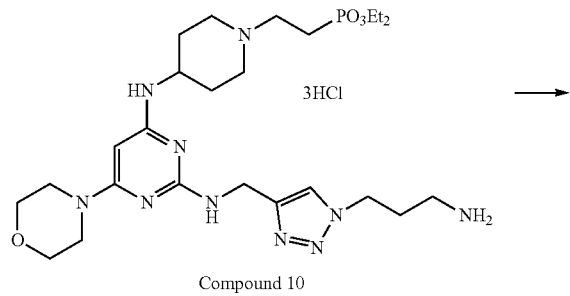

Compound 10

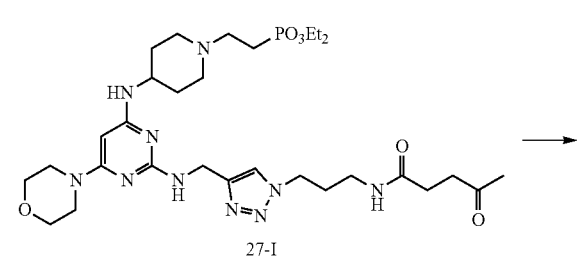

27-I

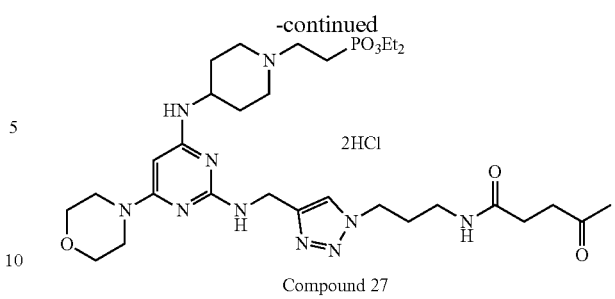

Compound 27

To a solution of Compound 10 (0.53 g, 0.8 mmol) in DCM (18 mL) were added EDCI (0.21 g, 1.1 mmol), HOBt (0.19 g, 1.2 mmol), TEA (0.3 g, 3.0 mmol), and Levulinic acid (0.14 g, 1.2 mmol) at 25° C. The reaction mixture was stirred for 15 h and then poured into water. The resulting mixture was extracted with DCM. The combined organic extracts were washed with brine, dried over anhydrous sodium sulfate, filtered, and concentrated. The residue thus obtained was purified by column chromatography on silica gel (MeOH:DCM=1:19) to afford 27-I (0.38 g, y: 73%).

A solution of 2N HCl/diethyl ether (1.2 mL, 2.4 mmol) was added to a DCM solution of 27-I (382 mg, 0.6 mmol). The reaction mixture was stirred at 25° C. for 15 h and then concentrated to afford a hydrochloride salt of Compound 27 (359 mg, y: 90%).

EI-MS: 679.3 (M+1).

Preparation of Compound 28-32

Compounds 28-32 were prepared in a manner similar to that used to prepare Compound 27.

Compound 28 EI-MS: 609.3 (M+1).

Compound 29 EI-MS: 738.4 (M+1). ¹H-NMR (D₂O, 400 MHz, free form) δ 7.79 (s, 1H), 4.46 (s, 2H), 4.28 (t, 2H), 4.05 (q, 4H), 3.61 (m, 1H), 3.57 (s, 3H), 3.55 (m, 4H), 3.42 (m, 4H), 3.23-3.18 (m, 6H), 3.02 (m, 2H), 2.76-2.68 (m, 4H), 2.53 (t, 2H), 2.28 (m, 2H), 2.16 (m, 2H), 1.96-1.86 (m, 4H), 1.61 (m, 2H), 1.17 (t, 6H).

Compound 30 EI-MS: 682.3 (M+1).

Compound 31 EI-MS: 710.4 (M+1). ¹H-NMR (CD₃OD, 300 MHz, free form) δ 7.81 (s, 1H), 4.47 (s, 2H), 4.32 (t, 2H), 4.02 (q, 4H), 3.97 (m, 1H), 3.64 (m, 1H), 3.57 (m, 4H), 3.42 (m, 4H), 3.33 (m, 2H), 3.20 (m, 2H), 3.02 (m, 4H), 2.83 (m, 2H), 2.58 (t, 2H), 2.36 (m, 2H), 2.17 (m, 2H), 2.00-1.92 (m, 4H), 1.62 (m, 2H), 1.20 (t, 6H), 1.09 (d, 3H).

Compound 32 EI-MS: 654.3 (M+1). ¹H-NMR (D₂O, 300 MHz) δ 7.98 (s, 1H), 4.46 (s, 2H), 4.34 (t, 2H), 3.96 (m, 1H), 3.64 (m, 1H), 3.57-3.50 (m, 6H), 3.36-3.31 (m, 6H), 3.08 (m, 4H), 2.83 (m, 2H), 2.58 (t, 2H), 2.00-1.92 (m, 8H), 1.62 (m, 2H), 1.09 (d, 3H).

Preparation of Compound 35

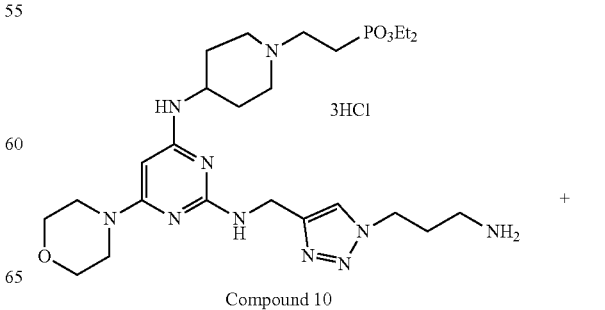

Compound 10

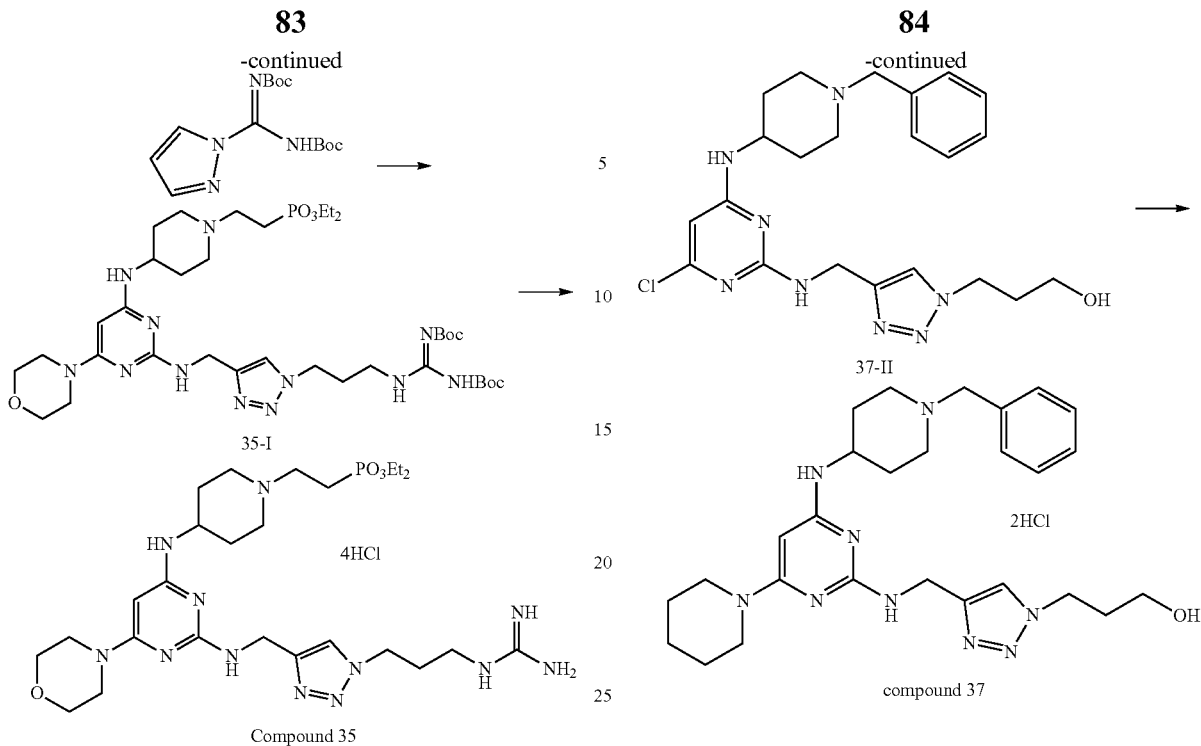

Compound 35

To a solution of Compound 10 (0.5 g, 0.7 mmol) in MeOH (5 mL) were added N,N'-di-Boc-1H-pyrazole-1-carboxamidine (0.28 g, 0.9 mmol) and TEA (0.37 g, 3.7 mmol). The mixture was stirred at room temperature for 15 h and then concentrated to give a crude residue, which was purified by column chromatography on silica gel (n-hexane:ethyl acetate=1:3) to afford 35-I (0.40 g, y: 67%).

To a solution of 2N HCl/diethyl ether (1 mL, 2 mmol) was added to a DCM solution of 35-I (310 mg, 0.4 mmol). The reaction mixture was stirred at 25° C. for 15 h and then concentrated to afford a hydrochloride salt of Compound 35 (261 mg, y: 90%).

EI-MS: 623.3 (M+1).

$^1$H-NMR (D$_2$O, 400 MHz) δ 7.84 (s, 1H), 4.52 (d, 2H), 4.36 (t, 2H), 4.03 (q, 4H), 3.72 (m, 1H), 3.61-3.40 (m, 10H), 3.28 (m, 2H), 3.05-3.00 (m, 4H), 2.30 (m, 2H), 2.20-1.98 (m, 4H), 1.64 (m, 2H), 1.32 (t, 6H).

Preparation of Compound 37

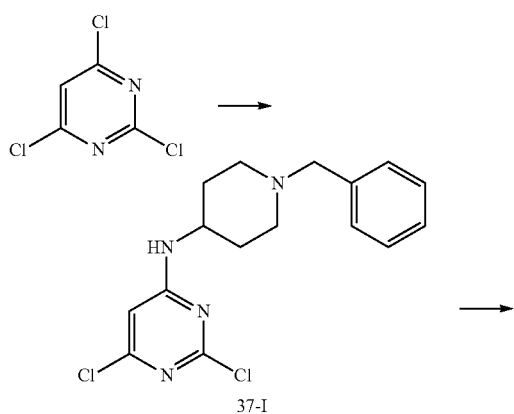

37-I compound 37

To the solution of 2,4,6-trichloropyrimidine (5.4 g, 29.4 mmol) in THF were added 1-benzyl-piperidin-4-ylamine (6.3 g, 33.1 mmol) and TEA (4.5 g, 44.6 mmol) under an atmosphere of nitrogen. The mixture was stirred at 60° C. for 15 h and then quenched with NH$_4$Cl(aq.) (50 mL, 2M). The resulting mixture was extracted with ethyl acetate. The combined organic extracts were washed with brine, dried over anhydrous sodium sulfate, filtered, and concentrated. The residue thus obtained was purified by column chromatography on silica gel (n-hexane:ethyl acetate=1:4) to afford 37-I (5.60 g, y: 56%).

A solution of 37-I (2 g, 5.9 mmol) and moiety 6 (1.08 g, 6.9 mmol) in IPA (40 mL) was heated at 145° C. for 15 h. The resulting mixture was concentrated. The residue thus obtained was purified by column chromatography on silica gel (MeOH:ethyl acetate=1:9) to afford 37-II (1.6 g, y: 59%).

A solution of 37-II (1.2 g, 2.6 mmol) and piperidine (1 g, 11.7 mmol) in IPA (40 mL) was sealed and heated at 120° C. for 15 h. The resulting mixture was concentrated. The residue thus obtained was purified by column chromatography on silica gel (MeOH:ethyl acetate=3:7) to afford 37-III (1.19 g, y: 89%).

$^1$H NMR (CD$_3$OD, 400 MHz, free form) δ 7.81 (s, 1H), 7.41-7.30 (m, 5H), 4.57 (s, 2H), 4.44 (t, 2H), 3.75 (s, 2H), 3.71 (m, 1H), 3.53 (t, 2H), 3.47 (m, 2H), 3.14 (m, 2H), 2.99 (m, 2H), 2.46 (m, 2H), 2.07 (m, 2H), 2.01 (m, 2H), 1.80 (m, 2H), 1.70-1.51 (m, 6H).

A solution of 2N HCl in diethyl ether (1.2 mL, 2.4 mmol) was added to a DCM solution of 37-III (305 mg, 0.6 mmol). The reaction mixture was stirred at 25° C. for 15 h and then concentrated to afford a hydrochloride salt of Compound 37 (320 mg, y: 92%).

EI-MS:506.3 (M+1).

Preparation of Compounds 38-44, 112, 115, 133, 136, 138, and 141

Compounds 38-44, 112, 115, 133, 136, 138, and 141 were prepared in a manner similar to that used to prepare Compound 37.

Compound 38 EI-MS: 416.3 (M+1).

Compound 39 EI-MS: 502.3 (M+1).

Compound 40 EI-MS: 493.3 (M+1).

Compound 41 EI-MS: 431.3 (M+1).

Compound 42 EI-MS: 439.2 (M+1).

Compound 43 EI-MS: 502.3 (M+1).

Compound 44 EI-MS: 430.3 (M+1).

Compound 112 EI-MS: 494.3 (M+1). $^1$H NMR (CDCl$_3$, 400 MHz, free form) δ 7.60 (s, 1H), 7.35-7.24 (m, 5H), 4.95 (s, 1H), 4.63 (d, 2H), 4.42 (t, 2H), 4.01 (t, 2H), 3.73 (m, 4H), 3.54 (s, 2H), 3.48-4.40 (m, 5H), 2.85 (m, 2H), 2.19 (m, 2H), 1.97 (m, 2H), 1.55 (m, 2H).

Compound 115 EI-MS: 522.3 (M+1). $^1$H NMR (CDCl$_3$, 400 MHz, free form) δ 7.49 (s, 1H), 7.30-7.23 (m, 5H), 4.95 (s, 1H), 4.70 (s, 2H), 4.31 (t, 2H), 3.73 (m, 4H), 3.54 (t, 2H), 3.48 (s, 2H), 3.47-4.40 (m, 5H), 2.77 (m, 2H), 2.11 (m, 2H), 2.01-1.93 (m, 4H), 1.56 (m, 2H).

Compound 133 EI-MS: 516.3 (M+1).

Compound 136 EI-MS: 542.3 (M+1).

Compound 138 EI-MS: 524.3 (M+1). $^1$H NMR (CDCl$_3$, 600 MHz, free form) δ 7.51 (s, 1H), 7.36-7.27 (m, 5H), 4.92 (s, 1H), 4.70 (s, 2H), 4.48 (t, 2H), 3.88 (m, 4H), 3.66 (t, 2H), 3.58 (s, 2H), 3.56 (m, 1H), 2.80 (m, 2H), 2.56 (m, 4H), 2.21 (m, 2H), 2.04 (m, 2H), 1.98 (m, 2H), 1.56 (m, 2H).

Compound 141 EI-MS: 556.2 (M+1).

Preparation of Compound 45

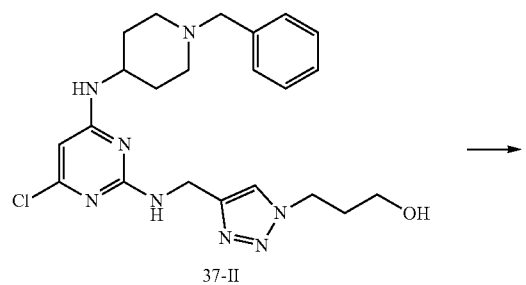

37-II

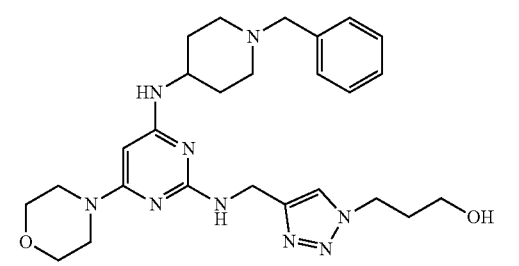

45-I

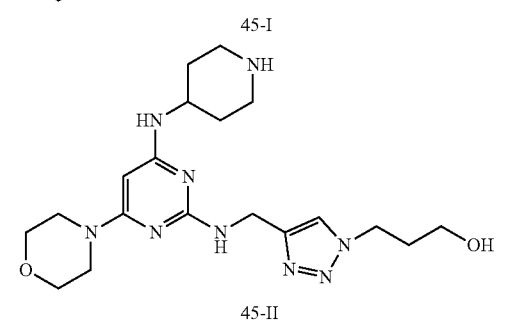

45-II

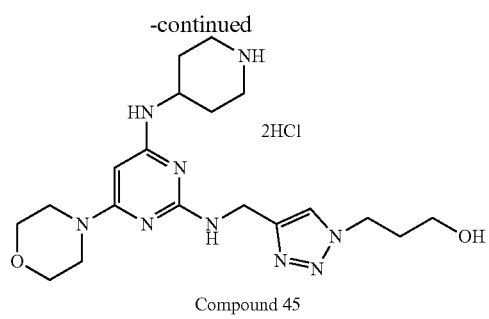

Compound 45

A solution of Compound 37-II (1.2 g, 2.6 mmol) and morpholine (1 g, 11.5 mmol) in IPA (40 mL) was sealed and heated at 120° C. for 15 h. The resulting mixture was concentrated. The residue thus obtained was purified by flash chromatography on silica gel (MeOH:ethyl acetate=1: 3) to afford 45-I (1.08 g, y: 81%).

A solution of 45-I (1.08 g, 2.1 mmol)) and 10% Pd/C (0.3 g) in 2-propanol (20 mL) was stirred under H$_2$(g) (1 atm) at 60° C. for 15 h. The resulting mixture was filtered. The filtrate was concentrated to afford 45-II (0.81 g, y: 91%).

$^1$H-NMR (CD$_3$OD, 400 MHz, free form) δ 7.76 (s, 1H), 4.81 (s, 1H), 4.55 (s, 2H), 4.45 (t, 2H), 3.89 (m, 1H), 3.68 (m, 4H), 3.53 (t, 2H), 3.40 (m, 4H), 3.10 (m, 2H), 2.76 (m, 2H), 2.05 (m, 2H), 1.95 (m, 2H), 1.40 (m, 2H).

A solution of 2N HCl/diethyl ether (1.5 mL, 3 mmol) was added to a DCM solution of 45-II (310 mg, 0.7 mmol). The reaction mixture was stirred at 25° C. for 15 h and then concentrated to afford a hydrochloride salt of Compound 45 (331 mg, y: 91%).

EI-MS: 418.2 (M+1).

Preparation of Compounds 49, 53, 54, 61, 81, 82, 85, 86, and 89-94

Compounds 49, 53, 54, 61, 81, 82, 85, 86, and 89-94 were prepared in a manner similar to that used to prepare Compound 45.

Compound 49 EI-MS: 508.3 (M+1). $^1$H-NMR (CDCl$_3$, 400 MHz, free form) δ 7.52 (s, 1H), 7.35-7.24 (m, 5H), 4.92 (d, 1H), 4.65 (d, 2H), 4.46 (t, 2H), 3.76-3.71 (m, 5H), 3.59 (t, 2H), 3.55 (s, 2H), 3.48 (m, 4H), 2.83 (m, 2H), 2.13 (m, 2H), 2.06 (m, 2H), 1.95 (m, 2H), 1.54 (m, 2H).

Compound 53 EI-MS: 418.2 (M+1).

Compound 54 EI-MS: 508.3 (M+1).

Compound 61 EI-MS: 432.2 (M+1).

Compound 81 EI-MS: 538.3 (M+1).

Compound 82 EI-MS: 548.3 (M+1).

Compound 85 EI-MS: 538.3 (M+1). $^1$H NMR (CDCl$_3$, 400 MHz, free form) δ 7.46 (s, 1H), 7.32-7.24 (m, 5H), 4.94 (s, 1H), 4.65 (d, 2H), 4.43 (t, 2H), 3.74 (m, 4H), 3.54 (m, 1H), 3.52 (s, 2H), 3.48 (m, 4H), 2.81 (m, 2H), 2.46 (t, 2H), 2.20-2.14 (m, 4H), 2.08 (s, 3H), 1.96 (m, 2H), 1.51 (m, 2H).

Compound 86 EI-MS: 448.2 (M+1).

Compound 89 EI-MS: 537.3 (M+1).

Compound 90 EI-MS: 447.2 (M+1).

Compound 91 EI-MS: 551.3 (M+1).

Compound 92 EI-MS: 461.3 (M+1).

Compound 93 EI-MS: 536.3 (M+1).

Compound 94 EI-MS: 446.3 (M+1).

Preparation of Compound 46

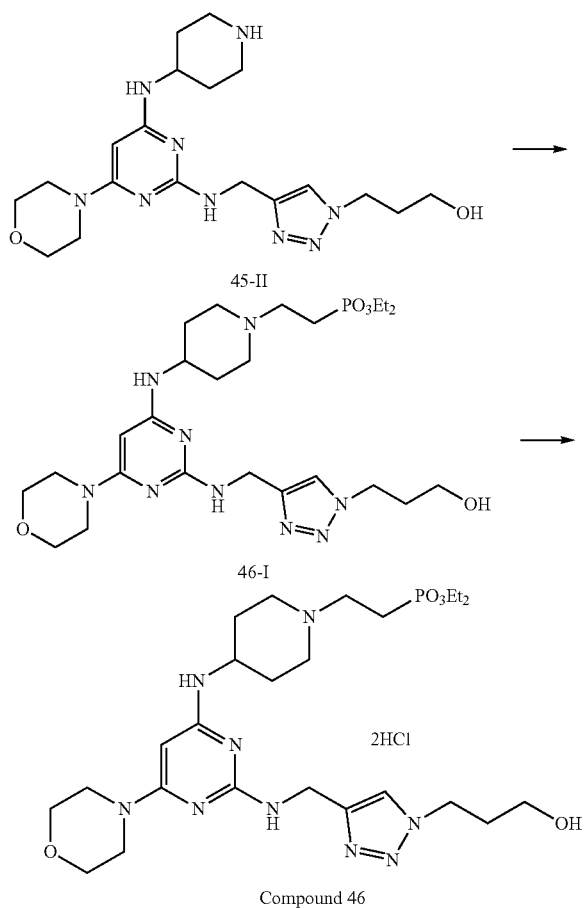

A solution of 45-II (0.51 g, 1.2 mmol), diethyl vinylphosphonate (0.4 g, 2.4 mmol), and TEA (3 drops) in MeOH (18 mL) was stirred at 60° C. for 16 h and then concentrated. The residue thus obtained was purified by flash chromatography on silica gel (MeOH:ethyl acetate=3:7) to afford 46-I (0.42 g, y: 59%). $^1$H-NMR (CDCl$_3$, 300 MHz, free form) δ 7.48 (s, 1H), 4.93 (s, 1H), 4.64 (d, 2H), 4.46 (t, 2H), 4.09 (q, 4H), 3.73 (m, 4H), 3.61 (t, 2H), 3.56 (m, 1H), 3.46 (m, 4H), 2.83 (m, 2H), 2.66 (m, 2H), 2.13 (t, 2H), 2.06 (m, 2H), 2.10-1.93 (m, 4H), 1.47 (m, 2H), 1.32 (t, 6H).

A solution of 2N HCl in diethyl ether (0.5 mL, 1 mmol) was added to a DCM solution of 46-I (150 mg, 0.3 mmol). The reaction mixture was stirred at 25° C. for 15 h and concentrated to afford a hydrochloride salt of Compound 46 (152 mg, y: 90%).

EI-MS: 582.3 (M+1).

Preparation of Compounds 48, 55, 57, 59, 62, 63, 83, 87, 95, 113, 116, 118, 134, 137, 139, 142, and 147

Compounds 48, 55, 57, 59, 62, 63, 83, 87, 95, 113, 116, 118, 134, 137, 139, 142, and 147 were prepared in a manner similar to that used to prepare Compound 46.

Compound 48 EI-MS: 504.3 (M+1). $^1$H NMR (CDCl$_3$, 400 MHz, free form) δ 7.53 (s, 1H), 4.93 (s, 1H), 4.66 (d, 2H), 4.48 (t, 2H), 3.75 (m, 4H), 3.70 (s, 3H), 3.60 (t, 2H), 3.52-3.46 (m, 5H), 2.84 (m, 2H), 2.71 (t, 2H), 2.52 (t, 2H), 2.16 (m, 2H), 2.09 (m, 2H), 1.98 (m, 2H), 1.50 (m, 2H).

Compound 55 EI-MS: 582.3 (M+1). $^1$H-NMR (CDCl$_3$, 400 MHz, free form) δ 7.63 (s, 1H), 4.92 (s, 1H), 4.65 (d, 2H), 4.39 (dd, 1H), 4.20 (dd, 1H), 4.08-4.03 (m, 5H), 3.73 (m, 4H), 3.58 (m, 1H), 3.48 (m, 4H), 2.85 (m, 2H), 2.68 (m, 2H), 2.21 (t, 2H), 2.02-1.96 (m, 4H), 1.53 (m, 2H), 1.32 (t, 6H), 1.24 (d, 3H).

Compound 57 EI-MS: 596.3 (M+1). $^1$H NMR (CD$_3$OD, 400 MHz, free form) δ 7.88 (s, 1H), 4.57 (s, 2H), 4.47 (t, 2H), 4.14 (q, 4H), 3.75-3.65 (m, 6H), 3.42 (m, 4H), 2.91 (m, 2H), 2.64 (m, 2H), 2.21 (m, 2H), 2.07-1.86 (m, 6H), 1.51 (m, 2H), 1.35 (t, 6H), 1.19 (d, 3H).

Compound 59 EI-MS: 610.3 (M+1). $^1$H-NMR (CD$_3$OD, 400 MHz, free form) δ 7.78 (s, 1H), 5.13 (s, 1H), 4.62 (d, 2H), 4.48 (t, 2H), 4.12 (q, 4H), 3.71 (m, 4H), 3.69 (m, 1H), 3.45 (m, 4H), 2.85 (m, 2H), 2.66 (m, 2H), 2.20 (t, 2H), 2.12-2.06 (m, 4H), 1.93 (m, 2H), 1.47 (m, 2H), 1.32 (t, 6H), 1.22 (s, 6H).

Compound 62 EI-MS: 518.3 (M+1). $^1$H NMR (CDCl$_3$, 400 MHz, free form) δ 7.55 (s, 1H), 4.93 (s, 1H), 4.68 (d, 2H), 4.42 (t, 2H), 3.74 (m, 4H), 3.60 (s, 3H), 3.56-3.52 (m, 5H), 3.35 (t, 2H), 3.32 (s, 3H), 2.93 (m, 2H), 2.80 (t, 2H), 2.57 (t, 2H), 2.33 (m, 2H), 2.13 (m, 2H), 2.00 (m, 2H), 1.63 (m, 2H).

Compound 63 EI-MS: 596.3 (M+1).
Compound 83 EI-MS: 610.3 (M+1).
Compound 87 EI-MS: 612.3 (M+1).
Compound 95 EI-MS: 610.3 (M+1).
Compound 113 EI-MS: 568.3 (M+1).
Compound 116 EI-MS: 596.3 (M+1).
Compound 118 EI-MS: 584.3 (M+1). $^1$H-NMR (CDCl$_3$, 400 MHz, free form) δ 7.44 (s, 1H), 4.90 (s, 1H), 4.59 (s, 2H), 4.38 (t, 2H), 3.32 (m, 2H), 4.06 (q, 4H), 3.69 (m, 4H), 3.45-3.41 (m, 5H), 2.79 (m, 2H), 2.62 (m, 2H), 2.25-1.84 (m, 8H), 1.45 (m, 2H), 1.28 (t, 6H).

Compound 134 EI-MS: 580.3 (M+1). $^1$H-NMR (CD$_3$OD, 400 MHz, free form) δ 7.80 (s, 1H), 4.57 (s, 2H), 4.46 (t, 2H), 4.17 (q, 4H), 3.65 (m, 1H), 3.55 (t, 2H), 3.49 (m, 4H), 2.91 (m, 2H), 2.70 (m, 2H), 2.26 (t, 2H), 2.10-2.07 (m, 4H), 1.97 (m, 2H), 1.65 (m, 2H), 1.57-1.55 (m, 6H), 1.31 (t, 6H).

Compound 137 EI-MS: 616.3 (M+1). $^1$H-NMR (CD$_3$OD, 400 MHz, free form) δ 7.79 (s, 1H), 4.58 (s, 2H), 4.47 (t, 2H), 4.14 (q, 4H), 3.64 (m, 1H), 3.62 (m, 4H), 3.55 (t, 2H), 2.93 (m, 2H), 2.68 (m, 2H), 2.23 (m, 2H), 2.09-2.06 (m, 4H), 1.97-1.82 (m, 6H), 1.51 (m, 2H), 1.35 (t, 6H).

Compound 139 EI-MS: 598.3 (M+1). $^1$H-NMR (CDCl$_3$, 400 MHz, free form) δ 7.50 (s, 1H), 4.88 (s, 1H), 4.61 (s, 2H), 4.44 (t, 1H), 4.11 (q, 4H), 3.86 (m, 4H), 3.57 (t, 2H), 3.52 (m, 1H), 2.80 (m, 2H), 2.64 (m, 2H), 2.56 (m, 4H), 2.15-1.95 (m, 8H), 1.53 (m, 2H), 1.48 (m, 2H), 1.32 (t, 6H).

Compound 142 EI-MS: 630.3 (M+1). $^1$H-NMR (CDCl$_3$, 400 MHz, free form) δ 7.50 (s, 1H), 5.06 (s, 1H), 4.63 (s, 2H), 4.50 (t, 1H), 4.17 (q, 4H), 4.06 (m, 4H), 3.70-3.61 (m, 3H), 2.98 (m, 4H), 2.83 (m, 2H), 2.71 (m, 2H), 2.20-1.96 (m, 8H), 1.51 (m, 2H), 1.31 (t, 6H).

Compound 147 EI-MS: 582.3 (M+1).

Preparation of Compound 47

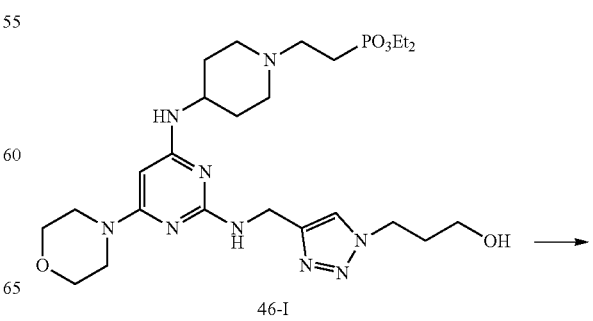

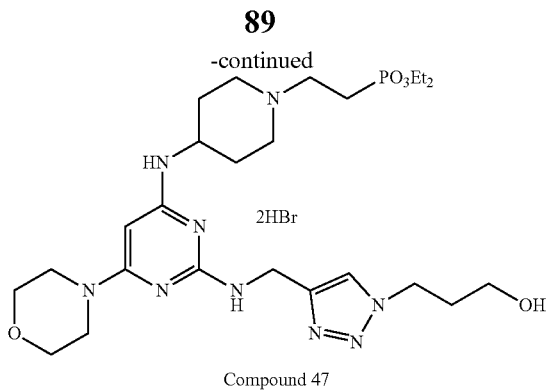

Compound 47

To a solution of 46-I (243 mg, 0.4 mmol) in DCM (0.5 mL) was added TMSBr (0.36 g, 2.4 mmol). The mixture was stirred at 25° C. for 4 h and then concentrated to afford a hydrobromide salt of Compound 47 (240 mg, y: 84%).

EI-MS: 526.2 (M+1). $^1$H-NMR (D$_2$O, 400 MHz) δ 7.88 (s, 1H), 5.33 (s, 1H), 4.56 (s, 2H), 4.40 (t, 2H), 3.76 (m, 1H), 3.63 (m, 4H), 3.57 (m, 2H), 3.48 (m, 4H), 3.42 (t, 2H), 3.24 (m, 2H), 3.02 (t, 2H), 2.17 (m, 2H), 2.07-1.95 (m, 4H), 1.65 (m, 2H).

Preparation of Compounds 56, 58, 60, 64, 84, 88, 96, 114, 117, 119, 123, 126, 128, 130, 135, 140, 143, 146, and 148

Compounds 56, 58, 60, 64, 84, 88, 96, 114, 117, 119, 123, 126, 128, 130, 135, 140, 143, 146, and 148 were prepared in a manner similar to that used to prepare Compound 47.

Compound 56 EI-MS: 526.2 (M+1). $^1$H-NMR (CD$_3$OD, 400 MHz) δ 8.29 (s, 1H), 4.79 (d, 2H), 4.54 (dd, 1H), 4.38 (dd, 1H), 4.17 (m, 1H), 3.79-3.57 (m, 11H), 3.42 (m, 2H), 3.32 (m, 2H), 2.36-2.20 (m, 4H), 1.84 (m, 2H), 1.21 (d, 3H).

Compound 58 EI-MS: 540.2 (M+1). $^1$H NMR (CD$_3$OD, 400 MHz) δ 8.17 (s, 1H), 4.75 (s, 2H), 4.58 (t, 2H), 4.10 (m, 1H), 3.80-3.70 (m, 10H), 3.47-3.43 (m, 3H), 3.31 (m, 2H), 2.36-2.25 (m, 4H), 2.08 (m, 2H), 1.96 (m, 2H), 1.22 (d, 3H).

Compound 60 EI-MS: 554.3 (M+1). $^1$H NMR (CD$_3$OD, 400 MHz) δ 8.12 (s, 1H), 4.73 (s, 2H), 4.57 (dd, 2H), 4.11 (m, 1H), 3.80-3.64 (m, 10H), 3.44 (m, 2H), 3.31 (m, 2H), 2.33-2.22 (m, 4H), 2.08 (m, 2H), 1.90 (m, 2H), 1.27 (s, 6H).

Compound 64 EI-MS: 540.2 (M+1). $^1$H NMR (D$_2$O, 600 MHz) δ 8.06 (s, 1H), 4.75 (s, 2H), 4.53 (t, 2H), 3.92 (m, 1H), 3.75-3.50 (m, 10H), 3.39 (m, 2H), 3.29 (t, 2H), 3.27 (s, 3H), 3.17 (m, 2H), 2.30 (m, 2H), 2.23-2.08 (m, 4H), 1.79 (m, 2H).

Compound 84 EI-MS: 554.2 (M+1).
Compound 88 EI-MS: 556.2 (M+1).
Compound 96 EI-MS: 554.3 (M+1).

Compound 114 EI-MS: 512.2 (M+1). $^1$H NMR ((D$_2$O, 600 MHz) δ 8.08 (s, 1H), 4.62 (s, 2H), 4.48 (t, 2H), 3.87 (t, 2H), 3.80 (m, 1H), 3.70-3.40 (m, 10H), 3.28 (m, 2H), 3.07 (m, 2H), 2.25-2.10 (m, 4H), 1.69 (m, 2H).

Compound 117 EI-MS: 540.2 (M+1). $^1$H NMR (D$_2$O, 400 MHz) δ 7.87 (s, 1H), 4.55 (s, 2H), 4.33 (t, 2H), 3.75 (m, 1H), 3.65-3.40 (m, 12H), 3.24 (m, 2H), 3.02 (m, 2H), 2.17 (m, 2H), 1.99 (m, 2H), 1.81 (m, 2H), 1.64 (m, 2H), 1.32 (m, 2H).

Compound 119 EI-MS: 528.2 (M+1).

Compound 123 EI-MS: 595.3 (M+1). $^1$H-NMR (CD$_3$OD, 400 MHz) δ 8.37 (s, 1H), 4.77 (s, 2H), 4.66 (t, 2H), 4.13 (m, 1H), 4.04 (m, 4H), 3.92-3.61 (m, 12H), 3.51-3.44 (m, 4H), 3.27-3.23 (m, 4H), 2.60 (m, 2H), 2.46-2.30 (m, 4H), 1.93 (m, 2H).

Compound 126 EI-MS: 643.3 (M+1). $^1$H-NMR (CD$_3$OD, 400 MHz) δ 8.30 (s, 1H), 4.76 (s, 2H), 4.62 (t, 2H), 4.10 (m, 1H), 3.98 (m, 4H), 3.86-3.60 (m, 12H), 3.50-3.31 (m, 6H), 3.25 (m, 2H), 2.61 (m, 2H), 2.46-2.31 (m, 4H), 1.89 (m, 2H).

Compound 128 EI-MS: 569.3 (M+1). $^1$H-NMR (CD$_3$OD, 400 MHz) δ 8.30 (s, 1H), 4.76 (s, 2H), 4.61 (t, 2H), 4.12 (m, 1H), 3.70-3.63 (m, 12H), 3.42 (m, 2H), 3.20-3.08 (m, 6H), 2.41-2.28 (m, 6H), 1.86 (m, 2H).

Compound 130 EI-MS: 752.3 (M+1).

Compound 135 EI-MS: 524.3 (M+1). $^1$H NMR (CD$_3$OD, 400 MHz) δ 8.14 (s, 1H), 4.73 (s, 2H), 4.57 (t, 2H), 4.11 (m, 1H), 3.75-3.59 (m, 6H), 3.58 (t, 2H), 3.43 (m, 2H), 3.28 (m, 2H), 2.36-2.12 (m, 6H), 1.91 (m, 2H), 1.75-1.60 (m, 6H).

Compound 140 EI-MS: 542.2 (M+1). $^1$H NMR (D$_2$O, 400 MHz) δ 7.91 (s, 1H), 4.54 (s, 2H), 4.39 (t, 2H), 3.80-3.70 (m, 5H), 3.58 (m, 2H), 3.42 (t, 2H), 3.27 (m, 2H), 3.04 (m, 2H), 2.50 (m, 4H), 2.17 (m, 2H), 2.06-1.98 (m, 4H), 1.68 (m, 2H).

Compound 143 EI-MS: 574.2 (M+1). $^1$H NMR (CD$_3$OD, 400 MHz) δ 8.00 (s, 1H), 4.71 (s, 2H), 4.52 (t, 2H), 4.24 (m, 4H), 4.11 (m, 1H), 3.74 (m, 2H), 3.57 (t, 2H), 3.43 (m, 2H), 3.33 (m, 2H), 3.18 (m, 4H), 2.34-2.24 (m, 4H), 2.12 (m, 2H), 1.91 (m, 2H).

Compound 146 EI-MS: 691.2 (M+1).
Compound 148 EI-MS: 526.2 (M+1).

Preparation of Compound 65

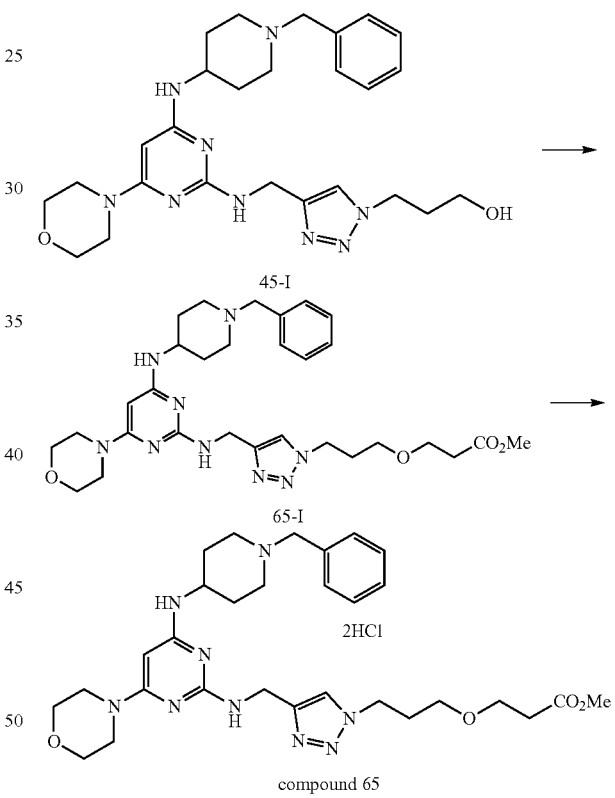

A solution of 45-I (2.38 g, 4.7 mmol), acrylic acid methyl ester (1.28 g, 15 mmol), and TEA (3.8 g, 37.6 mmol) in MeOH (50 mL) was stirred at 60° C. for 16 h and then concentrated. The residue thus obtained was purified by column chromatography on silica gel (MeOH:ethyl acetate=1:4) to afford 65-I (2.01 g, y: 72%).

$^1$H-NMR (CDCl$_3$, 300 MHz, free form) δ 7.50 (s, 1H), 7.38-7.20 (m, 5H), 4.88 (d, 1H), 4.63 (d, 2H), 4.45 (t, 2H), 3.92 (m, 1H), 3.75 (m, 4H), 3.70 (s, 3H), 3.67 (t, 2H), 3.51 (s, 2H), 3.03 (m, 4H), 2.83 (m, 2H), 2.66 (t, 2H), 2.45 (t, 2H), 2.13 (m, 2H), 2.06 (m, 2H), 1.95 (m, 2H), 1.54 (m, 2H).

A solution of 2N HCl in diethyl ether (0.75 mL, 1.5 mmol) was added to a DCM solution of 65-I (302 mg, 0.5 mmol).

The reaction mixture was stirred at 25° C. for 15 h and then concentrated to afford a hydrochloride salt of Compound 65 (312 mg, y: 92%).

EI-MS: 594.3 (M+1).

Preparation of Compound 66

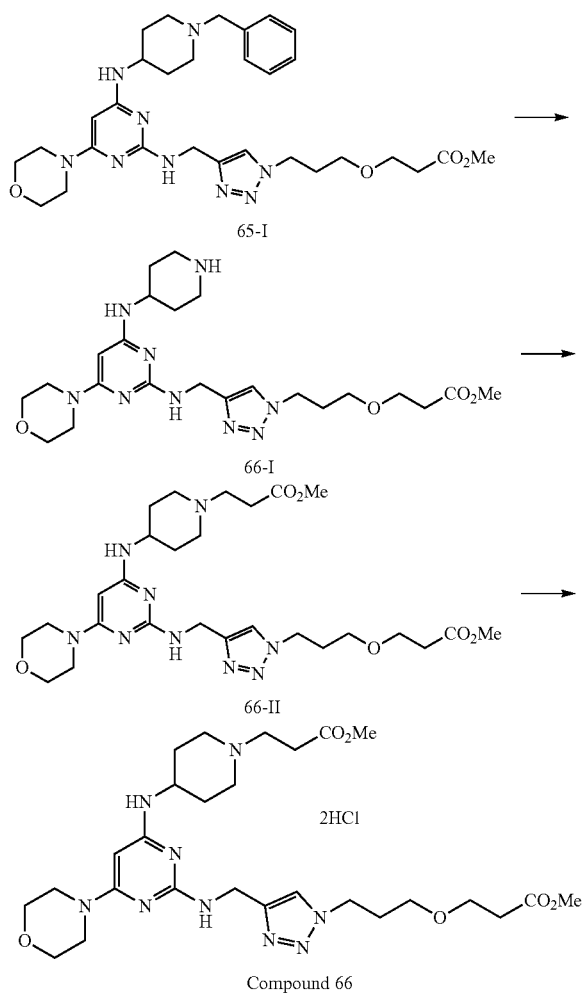

Compound 66

A solution of 65-I (1.7 g, 2.9 mmol) and 10% Pd/C (0.51 g) in 2-propanol (34 mL) was stirred under $H_2(g)$ (1 atm) at 60° C. for 15 h and then filtered. The filtrate was concentrated to afford 66-I (1.34 g, y: 93%).

A solution of 66-I (0.3 g, 0.6 mmol), acrylic acid methyl ester (0.15 g, 1.8 mmol) and TEA (0.38 g, 3.8 mmol) in MeOH (18 mL) was stirred at 60° C. for 16 h and then concentrated. The residue thus obtained was purified by column chromatography on silica gel (MeOH:ethyl acetate=1:4) to give 66-II (0.23 g, y: 65%).

$^1$H NMR (CDCl$_3$, 400 MHz, free form) 7.53 (s, 1H), 4.92 (d, 1H), 4.64 (d, 2H), 4.48 (t, 2H), 3.91 (m, 1H), 3.78 (m, 4H), 3.71 (s, 3H), 3.69 (s, 3H), 3.63 (t, 2H), 3.05 (m, 4H), 2.84 (m, 2H), 2.73-2.65 (m, 4H), 2.54-2.48 (m, 4H), 2.21-2.10 (m, 4H), 1.97 (m, 2H), 1.49 (m, 2H).

A solution of 2N HCl in diethyl ether (1 mL, 2 mmol) was added a DCM solution of 66-II (231 mg, 0.4 mmol). The reaction mixture was stirred at 25° C. for 2 h and then concentrated to afford a hydrochloride salt of Compound 66 (241 mg, y: 93%).

EI-MS: 590.3 (M+1).

Preparation of Compound 67

Compound 67 was prepared in a manner similar to that used to prepare Compound 66.

EI-MS: 668.3 (M+1). $^1$H-NMR (CDCl$_3$, 300 MHz, free form) δ 7.50 (s, 1H), 4.97 (d, 1H), 4.62 (d, 2H), 4.45 (t, 2H), 4.07 (q, 4H), 3.89 (m, 1H), 3.75 (m, 4H), 3.68 (s, 3H), 3.59 (t, 2H), 3.02 (m, 4H), 2.85 (m, 2H), 2.76-2.60 (m, 4H), 2.47 (t, 2H), 2.18 (m, 2H), 2.10-1.93 (m, 6H), 1.47 (m, 2H), 1.31 (t, 6H).

Preparation of Compound 68

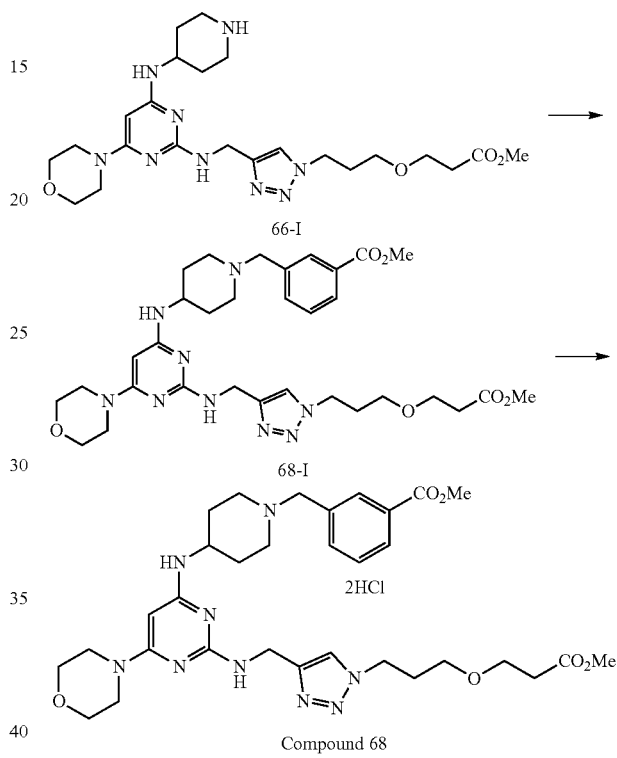

Compound 68

A solution of 66-I (0.4 g, 0.8 mmol), 3-bromomethyl-benzoic acid methyl ester (0.6 g, 2.6 mmol), and TEA (0.3 g, 3 mmol) in THF (12 mL) was stirred at 25° C. for 16 h and then quenched with NH$_4$Cl(aq.) (20 mL, 2M). The resulting mixture was extracted with ethyl acetate. The combined extracts were washed with water and brine, dried over anhydrous sodium sulfate, filtered, and concentrated. The residue was purified by column chromatography on silica gel (MeOH:ethyl acetate=1:4) to afford 68-I (0.34 g, y: 66%).

$^1$H-NMR (CDCl$_3$, 300 MHz, free form) δ 7.94 (s, 1H), 7.89 (d, 1H), 7.51 (d, 1H), 7.50 (s, 1H), 7.36 (t, 1H), 4.93 (d, 1H), 4.60 (d, 2H), 4.43 (t, 2H), 3.88 (m, 1H), 3.87 (s, 3H), 3.73 (m, 4H), 3.67 (s, 3H), 3.57 (t, 2H), 3.52 (s, 2H), 3.00 (m, 4H), 2.78 (m, 2H), 2.64 (t, 2H), 2.46 (t, 2H), 2.13 (m, 2H), 2.03 (m, 2H), 1.92 (m, 2H), 1.48 (m, 2H).

A solution of 2N HCl in diethyl ether (0.75 mL, 1.5 mmol) was added a DCM solution of 68-I (0.34 g, 0.5 mmol). The reaction mixture was stirred at 25° C. for 2 h and then concentrated to afford a hydrochloride salt of Compound 68 (0.35 g, y: 93%).

EI-MS: 652.3 (M+1).

Preparation of Compounds 70, 71, 72, 75, and 76

Compounds 70, 71, 72, 75, and 76 were prepared in a manner similar to that used to prepare Compound 68.

Compound 70 EI-MS: 662.3 (M+1). $^1$H-NMR (CDCl$_3$, 400 MHz, free form) δ 7.53 (d, 2H), 7.50 (s, 1H), 7.43 (d, 2H), 4.57 (s, 2H), 4.37 (t, 2H), 3.95 (m, 1H), 3.70 (m, 4H), 3.64 (s, 3H), 3.62 (s, 2H), 3.52 (t, 2H), 3.01 (m, 4H), 2.87 (m, 2H), 2.60 (t, 2H), 2.42 (t, 2H), 2.23 (m, 2H), 2.04 (m, 2H), 1.88 (m, 2H), 1.54 (m, 2H).
Compound 71 EI-MS: 652.3 (M+1). $^1$H-NMR (CDCl$_3$, 400 MHz, free form) δ 8.02 (d, 2H), 7.64 (s, 1H), 7.48 (d, 2H), 4.65 (s, 2H), 4.48 (t, 2H), 3.98 (m, 1H), 3.78 (s, 3H), 3.76 (s, 2H), 3.67 (m, 4H), 3.65 (s, 3H), 3.57 (t, 2H), 3.12 (m, 4H), 3.00 (m, 2H), 2.67 (t, 2H), 2.52 (t, 2H), 2.43 (m, 2H), 2.04 (m, 2H), 1.97 (m, 2H), 1.68 (m, 2H).
Compound 72 EI-MS: 619.3 (M+1).
Compound 75 EI-MS: 644.3 (M+1). $^1$H-NMR (CD$_3$OD, 400 MHz, free form) δ 8.04 (s, 1H), 7.99-7.90 (m, 3H), 7.78 (s, 1H), 7.64 (d, 1H), 7.56-7.53 (m, 2H), 4.56 (s, 2H), 4.42 (t, 2H), 4.36 (s, 2H), 3.92 (m, 1H), 3.75 (m, 4H), 3.63 (s, 3H), 3.48 (t, 2H), 3.37 (m, 2H), 3.03 (m, 2H), 3.01 (m, 4H), 2.70 (t, 2H), 2.46 (t, 2H), 2.08-2.01 (m, 4H), 1.78 (m, 2H).
Compound 76 EI-MS: 669.3 (M+1).
Preparation of Compound 69
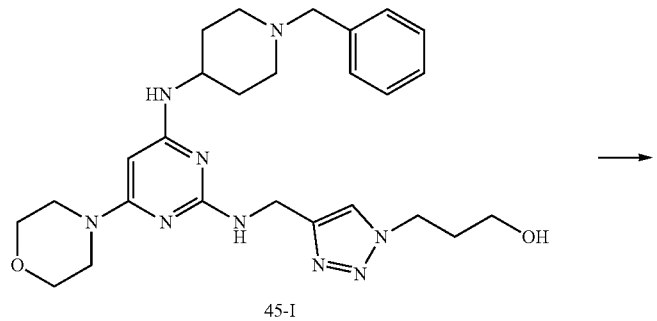
45-I
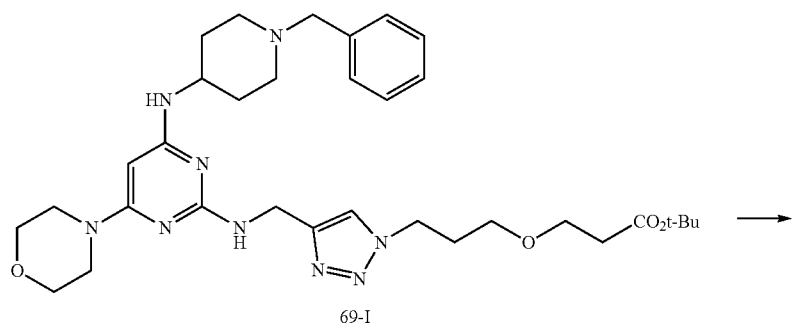
69-I
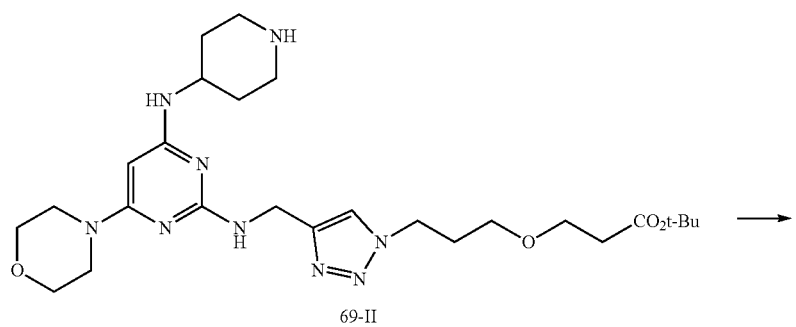
69-II
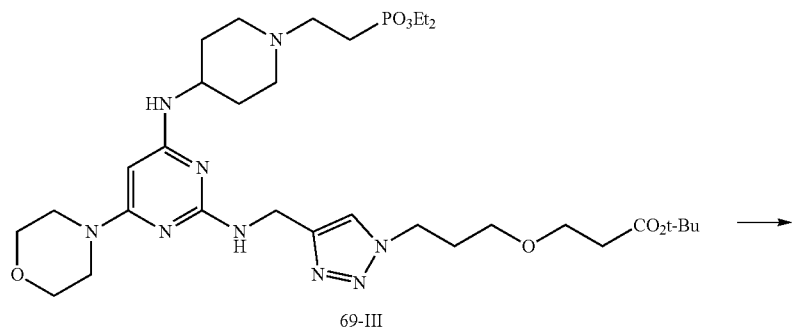
69-III

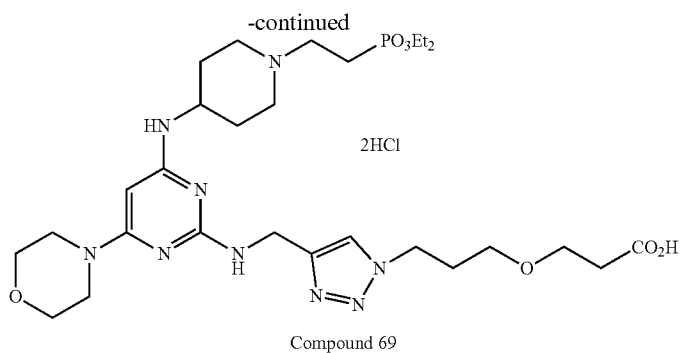

Compound 69

A solution of 45-I (0.53 g, 1 mmol), acrylic acid tert-butyl ester (0.45 g, 3.5 mmol), and TEA (0.35 g, 3.5 mmol) in MeOH (20 mL) was stirred at 60° C. for 16 h and then concentrated. The residue thus obtained was purified by column chromatography on silica gel (MeOH:ethyl acetate=1:4) to give 69-I (0.52 g, y: 78%).

A solution of 69-I (0.52 g, 0.8 mmol) and 10% Pd/C (0.15 g) in 2-propanol (10 mL) was stirred under $H_2(g)$ (1 atm) at 60° C. for 15 h. The resulting mixture was filtered. The filtrate was concentrated to give 69-II (0.41 g, y: 92%).

A solution of 69-II (0.41 g, 0.8 mmol), diethyl vinylphosphonate (0.26 g, 1.6 mmol), and TEA (1 drops) in MeOH (12 mL) was stirred at 60° C. for 16 h and then concentrated. The residue thus obtained was purified by column chromatography on silica gel (MeOH:ethyl acetate=3:7) to give 69-III (0.31 g, y: 58%).

A solution of 2N HCl in diethyl ether (0.75 mL, 1.5 mmol) was added to a DCM solution of 69-III (0.31 g, 0.4 mmol). The reaction mixture was stirred at 25° C. for 2 h and then concentrated to afford a hydrochloride salt of Compound 69 (0.28 g, y: 88%).

EI-MS: 654.3 (M+1).

Preparation of Compound 105

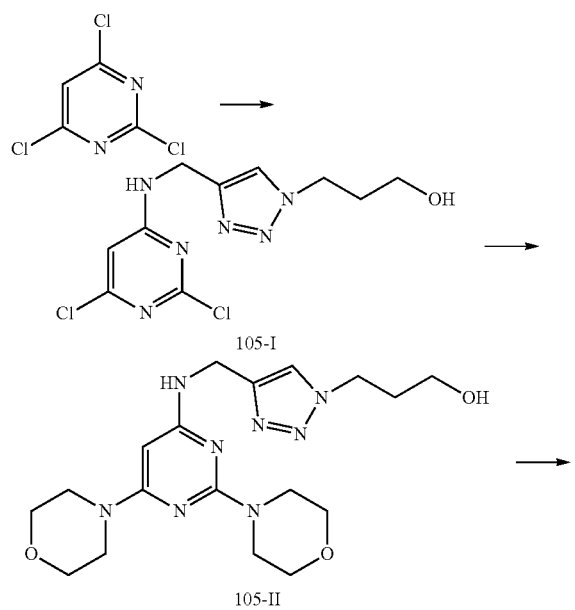

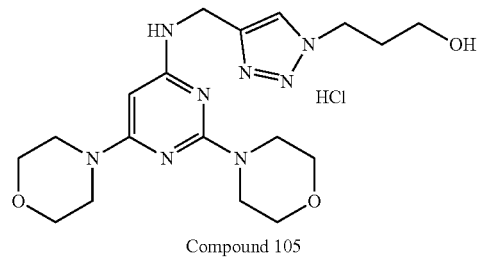

Compound 105

To a solution of 2,4,6-trichloropyrimidine (1.83 g, 10 mmol) in THF (54 mL) was added moiety 6 (2.41 g, 15.4 mmol) and TEA (2 g, 19.8 mmol). The mixture was stirred at 25° C. for 15 h and then quenched with $NH_4Cl(aq.)$ (50 mL, 2 M). The resulting solution was extracted with ethyl acetate (3×100 mL). The combined extracts were washed with brine, dried over anhydrous sodium sulfate, filtered, and concentrated. The residue thus obtained was purified by column chromatography on silica gel (n-hexane:ethyl acetate=1:1) to give 105-I (0.76 g, y: 25%).

To a solution of 105-I (0.76 g, 2.5 mmol) in IPA (25 mL) was added morpholine (1.4 g, 16.1 mmol). The mixture was stirred at 120° C. for 15 h and then concentrated. The residue thus obtained was purified by column chromatography on silica gel (n-hexane:ethyl acetate=1:3) to afford 105-II (0.67 g, y: 66%).

A solution of 2N HCl in diethyl ether (1.2 mL, 2.4 mmol) was added to a DCM solution of 105-II (0.31 g, 0.8 mmol). The reaction mixture was stirred at 25° C. for 15 h and then concentrated to afford hydrochloride salt of Compound 105 (0.32 g, y: 95%).

EI-MS: 405.2 (M+1).

Preparation of Compounds 106-107

Compounds 106-107 were prepared in a manner similar to that used to prepare Compound 105.

Compound 106 EI-MS: 433.2 (M+1).

Compound 107 EI-MS: 418.2 (M+1).

Preparation of Compound 108

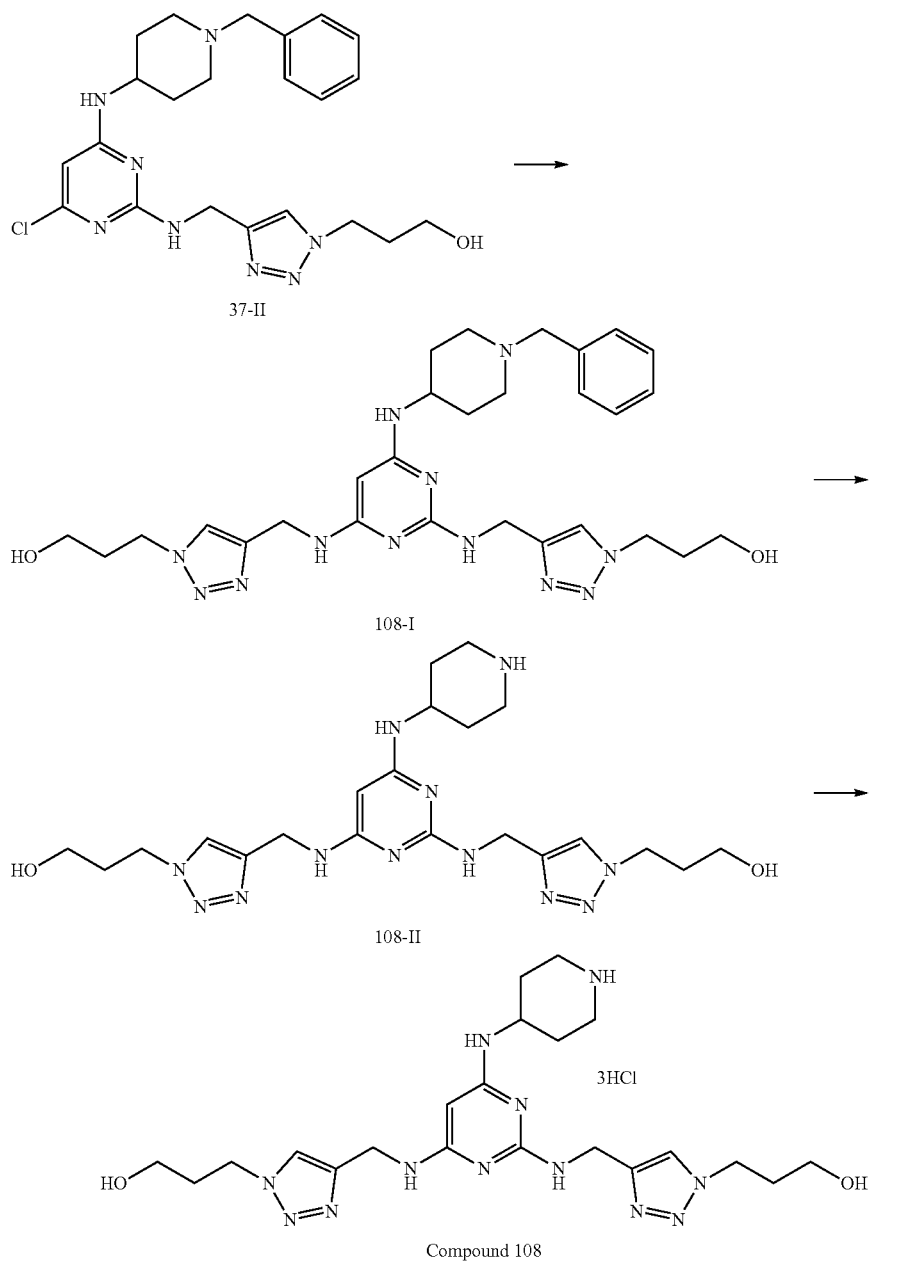

A solution of 37-II (1.4 g, 3.1 mmol), tetrabutylammonium bromide (1 g, 3.1 mmol), and moiety 6 (0.7 g, 4.5 mmol) in 2-pentanol (30 mL) was stirred at 140° C. for 15 h and then concentrated. The residue thus obtained was purified by column chromatography on silica gel (MeOH: ethyl acetate=1:3) to afford 108-I (0.48 g, y: 27%).

A solution of 108-I (0.48 g, 0.8 mmol) and 10% Pd/C (0.15 g) in 2-propanol (10 mL) was stirred under $H_2(g)$ (1 atm) at 60° C. for 15 h and then filtered. The filtrate was concentrated to give 108-II (0.36 g, y: 89%).

A solution of 2N HCl in diethyl ether (0.5 mL, 1 mmol) was added to a DCM solution of 108-II (0.15 g, 0.3 mmol). The reaction mixture was stirred at 25° C. for 15 h and then concentrated to afford a hydrochloride salt of Compound 108 (0.17 g, y: 93%).

EI-MS: 487.3 (M+1).

Preparation of Compound 110

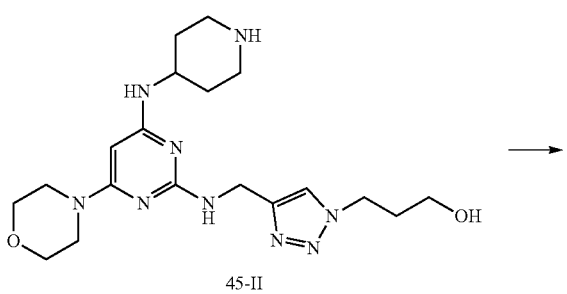

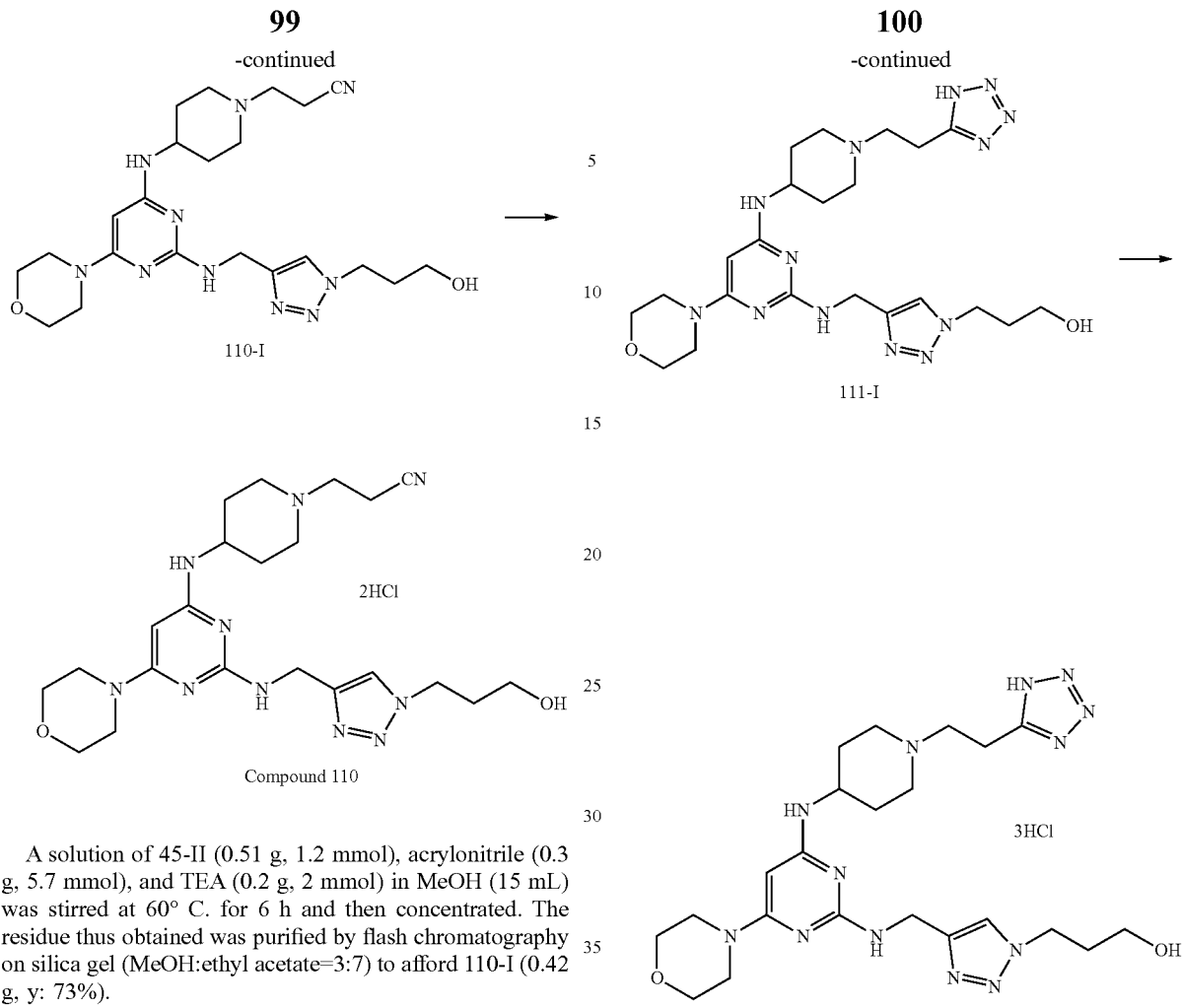

A solution of 45-II (0.51 g, 1.2 mmol), acrylonitrile (0.3 g, 5.7 mmol), and TEA (0.2 g, 2 mmol) in MeOH (15 mL) was stirred at 60° C. for 6 h and then concentrated. The residue thus obtained was purified by flash chromatography on silica gel (MeOH:ethyl acetate=3:7) to afford 110-I (0.42 g, y: 73%).

$^1$H-NMR (CD$_3$OD, 400 MHz, free form) δ 7.78 (s, 1H), 4.58 (s, 2H), 4.47 (t, 2H), 3.73-3.66 (m, 5H), 3.56 (t, 2H), 3.42 (m, 4H), 2.90 (m, 2H), 2.69 (m, 2H), 2.66 (m, 2H), 2.26 (m, 2H), 2.20 (m, 2H), 1.92 (m, 2H), 1.51 (m, 2H).

A solution of 2N HCl in diethyl ether (0.5 mL, 1 mmol) was added to a DCM solution of 110-I (200 mg, 0.3 mmol). The reaction mixture was stirred at 25° C. for 15 h and concentrated to afford a hydrochloride salt of Compound 110 (210 mg, y: 91%).

EI-MS: 471.3 (M+1).

Preparation of Compound 111

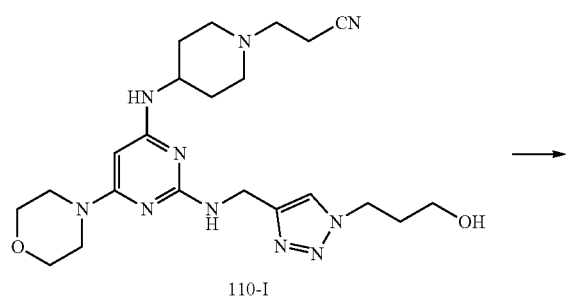

To a solution of 110-I (1.51 g, 3.2 mmol) and sodium azide (1.01 g, 15.4 mmol) in isopropyl alcohol (75 mL) was added a solution of ZnBr$_2$ (0.36 g, 1.6 mmol) in H$_2$O (15 mL). The mixture was stirred at 100° C. for 15 h and then concentrated to obtain a residue, which was extracted with DCM (3×100 mL). The combined extracts were washed with brine, dried over anhydrous sodium sulfate, filtered, and concentrated. The residue thus obtained was purified by flash chromatography on silica gel (MeOH:ethyl acetate=3:7) to afford 111-I (1.28 g, y: 78%).

$^1$H-NMR (CD$_3$OD, 400 MHz, free form) δ 7.80 (s, 1H), 4.58 (s, 2H), 4.47 (t, 2H), 3.74-3.68 (m, 5H), 3.55 (t, 2H), 3.43 (m, 4H), 3.10-3.08 (m, 4H), 2.94 (m, 2H), 2.43 (m, 2H), 2.09 (m, 2H), 1.92 (m, 2H), 1.57 (m, 2H).

A solution of 2N HCl in diethyl ether (1 mL, 2 mmol) was added to a DCM solution of 111-I (310 mg, 0.6 mmol). The reaction mixture was stirred at 25° C. for 15 h and concentrated to afford a hydrochloride salt of Compound 111 (315 mg, y: 84%).

EI-MS: 514.3 (M+1).

Preparation of Compound 129

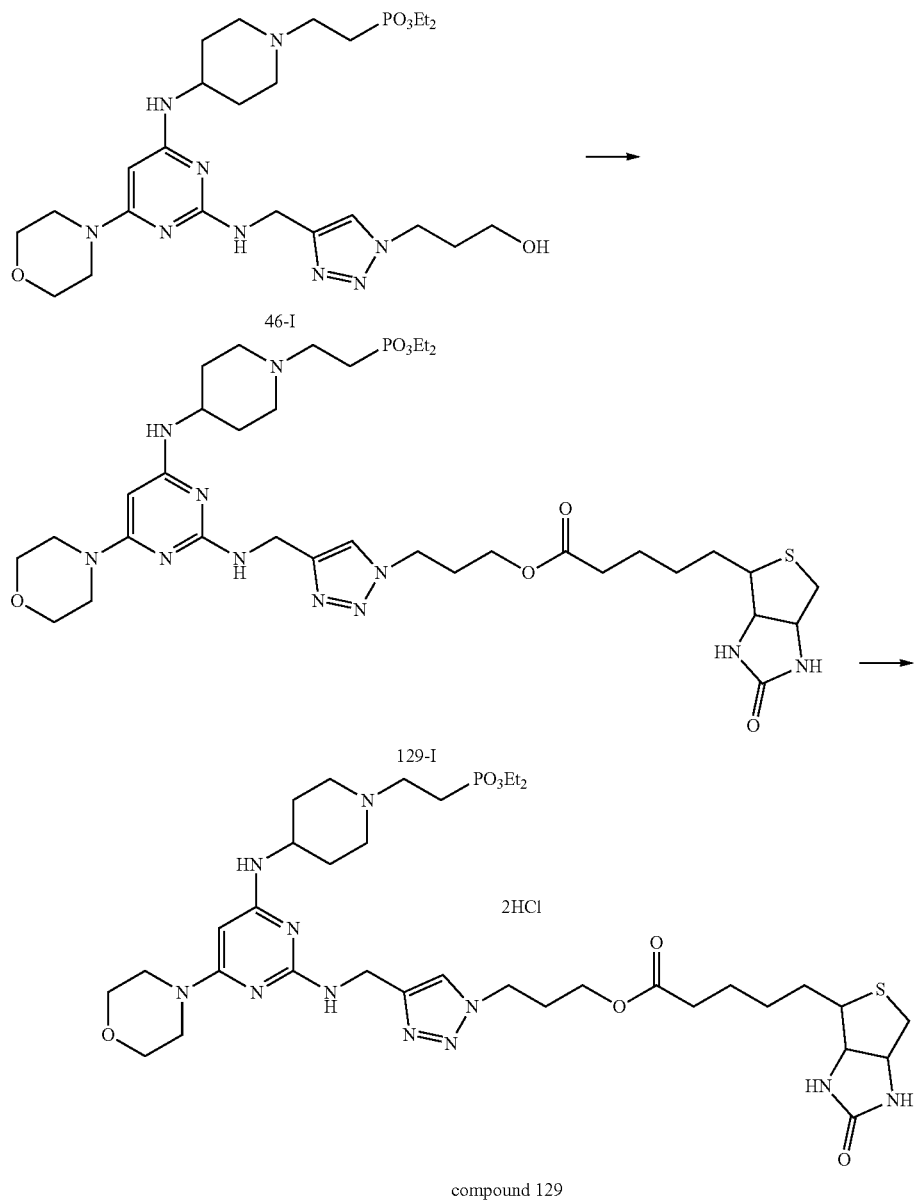

To a solution of Compound 46-I (301 mg, 0.5 mmol) in DMF (11 mL) were added EDCI (265 mg, 1.4 mmol), DMAP (28 mg, 0.2 mmol), and biotin (337 mg, 1.4 mmol). The reaction mixture was stirred at 25° C. for 72 h and then poured into water. The resulting mixture was extracted with DCM. The combined organic extracts were washed with brine, dried over anhydrous sodium sulfate, filtered, and concentrated. The residue thus obtained was purified by column chromatography on silica gel (MeOH:DCM=1:19) to afford 129-I (242 mg, y: 57%). $^1$H-NMR (CD$_3$OD, 400 MHz, free form) δ 7.76 (s, 1H), 4.56 (s, 2H), 4.46 (t, 2H), 4.30 (m, 1H), 4.13 (q, 4H), 4.06 (t, 2H), 3.77-3.66 (m, 6H), 3.42 (m, 4H), 3.25 (m, 1H), 2.90-2.80 (m, 3H), 2.70-2.63 (m, 3H), 2.28 (t, 2H), 2.23-2.20 (m, 4H), 2.06 (m, 2H), 1.96 (m, 2H), 1.75-1.46 (m, 8H), 1.32 (t, 6H).

A solution of 2N HCl/diethyl ether (0.5 mL, 1 mmol) was added to a DCM solution of 129-I (242 mg, 0.3 mmol). The reaction mixture was stirred at 25° C. for 15 h and then concentrated to afford a hydrochloride salt of Compound 129 (237 mg, y: 90%).

EI-MS: 808.4 (M+1).

Example 3: Neurite Outgrowth Assay

Compounds of this invention were evaluated using the neurite outgrowth assay as described in Chen et al., Scientific Reports, 7, 45366, DOI: 10.1038/srep45366 (2017).

Cell culture. For primary culture, dorsal root ganglia ("DRG") were removed from 7-weeks-old C57BL/6 J mice and digested with 0.1% collagenase (Sigma-Aldrich, St. Louis, MO) for 1 hour, followed by 0.25% trypsin treatment for 25 minutes. The dissociated neuron cultures were plated at a density of 2.5×10$^4$ cells per well in a 96 well optics plates (CLS3614; Sigma-Aldrich) precoated with 1 mg/mL poly-D-lysine (A-003-M; Sigma-Aldrich) for 3 hours. Primary DRG cells were grown in DMEM-F12 (11320033; Gibco®, ThermoFisher Scientific, Waltham, MA) supplemented with 10% fetal bovine serum (FBS, 26140079; Gibco®, ThermoFisher). These cells were maintained at 37° C. in an environment containing 5% $CO_2$.

Neurite outgrowth assay (group A). Primary DRG cells were incubated with one of the Example 2 compounds at 1 µM for 24 hours, and then treated with 0.05 µM paclitaxel for another 24 hours. After the paclitaxel treatment, the primary DRG cells were washed by PBS and then fixed with 4% paraformaldehyde (PFA, P6148; Sigma-Aldrich) for 15 minutes. The DRG cells thus fixed were permeabilized by 0.05% Triton X-100 in PBS for 20 minutes and blocked with 3% bovine serum albumin (BSA; Sigma-Aldrich, USA) at room temperature for 1 hour. Subsequently, DRG cells were stained with rabbit anti-β III tubulin (1:600; Cell Signaling, USA) and mouse anti-NeuN monoclonal antibody (1:400; Millipore, USA) overnight at 4° C. The samples were then washed by PBS and reacted with secondary antibodies (Alexa-488 and Alexa-594 1:600; Invitrogen, CA) at room temperature for 1 hour. For image acquisition and analysis of DRG neurite outgrowth, images of stained cells were automatically acquired using 10× objective by Image Xpress Micro wide field fluorescent microscope (Molecular Devices, USA). A control was obtained following the same procedure except that the DRG cells were not treated with a compound or paclitaxel. Neurite outgrowth was measured as a percentage of outgrowth as compared to the control.

Paclitaxel was found inhibiting neurite outgrowth due to its neurotoxicity. Compounds of this invention effectively protected DRG cells from paclitaxel-induced neurotoxicity. The results are provided in Table 1 below. In Table 1, column A shows neurite outgrowth of DRG cells that were treated with 1 µM of a compound of this invention and 0.05 µM of paclitaxel and column B shows neurite outgrowth of DRG cells that were treated with 0.05 µM of paclitaxel. The difference between A and B indicates an extent of protection provided by the compound.

TABLE 1

| Compound | A | B | A-B | p value | potential of neuroprotective effect |
|---|---|---|---|---|---|
| 6 | 46 | 43 | 3 | * | ++ |
| 15 | 35 | 32 | 3 | * | ++ |
| 17 | 50 | 47 | 3 |  | + |
| 18 | 50 | 47 | 3 |  | + |
| 21 | 45 | 42 | 3 |  | + |
| 28 | 53 | 50 | 3 | * | ++ |
| 38 | 37 | 32 | 5 |  | + |
| 41 | 34 | 31 | 3 |  | + |
| 42 | 34 | 31 | 3 |  | + |
| 46 | 55 | 47 | 8 | ** | +++ |
| 47 | 65 | 47 | 18 | * | +++ |
| 48 | 58 | 47 | 11 |  | + |
| 53 | 47 | 45 | 2 | ** | ++ |
| 59 | 47 | 42 | 5 | * | ++ |
| 60 | 40 | 44 | 4 | ** | +++ |
| 61 | 52 | 49 | 3 |  | + |
| 62 | 50 | 47 | 3 |  | + |
| 63 | 42 | 40 | 2 | *** | ++ |
| 66 | 52 | 47 | 5 |  | + |
| 67 | 43 | 40 | 3 | ** | +++ |
| 68 | 41 | 40 | 1 | * | ++ |
| 69 | 41 | 40 | 1 | * | ++ |
| 72 | 45 | 42 | 3 |  | + |
| 73 | 45 | 42 | 3 |  | + |
| 74 | 45 | 42 | 3 | * | ++ |
| 77 | 48 | 42 | 6 |  | + |
| 78 | 35 | 32 | 3 | * | ++ |
| 81 | 52 | 50 | 2 | * | ++ |
| 97 | 45 | 40 | 5 | * | ++ |
| 98 | 45 | 40 | 5 |  | + |
| 100 | 52 | 49 | 3 |  | + |
| 101 | 53 | 47 | 6 |  | + |
| 104 | 45 | 40 | 5 | * | ++ |
| 108 | 41 | 50 | 9 | ** | +++ |
| 109 | 41 | 51 | 10 | * | +++ |
| 114 | 55 | 47 | 8 | ** | ++ |
| 117 | 58 | 47 | 11 | ** | +++ |
| 135 | 56 | 50 | 6 | * | + |
| 140 | 54 | 50 | 4 |  | + |
| 143 | 57 | 50 | 7 |  | + |

*p < 0.05, p < 0.01, and *p < 0.001.

As shown in Table 1, 0.05 µM paclitaxel inhibited a 50%-69% of DRG neurite outgrowth. Unexpectedly, it is found that neuroprotection was provided by Compounds 6, 15, 17, 18, 21, 28, 38, 41, 42, 46, 47, 48, 53, 59, 60, 61, 62, 65, 66, 67, 68, 69, 72, 73, 74, 75, 78, 81, 97, 98, 100, 101, 104, 108, 109, 114, 117, 135, 140, and 143. Notably, Compound 47 showed more than 18% of improvement (i.e., 65% outgrowth as compared to 47% in paclitaxel treated cells).

Neurite outgrowth assay (group B). Primary DRG cells were incubated with compounds 17, 47, 97, 98, 101, 104 at 1 µM for 24 hours, and then treated with 100 µM oxaliplatin for another 48 hours. The treatment was obtained following the same procedure as group A except that the DRG cells were treated with a oxaliplatin. Neurite outgrowth was measured as a percentage of outgrowth as compared to the control.

Oxaliplatin was found inhibiting neurite outgrowth due to its neurotoxicity. Compounds of this invention effectively protected DRG cells from oxaliplatin-induced neurotoxicity. The results are provided in Table 2 below.

TABLE 2

| Compound | A | B | A-B | p value | potential of neuroprotective effect |
|---|---|---|---|---|---|
| 17 | 26 | 29 | −3 |  |  |
| 47 | 47 | 40 | 7 | ** | ++ |
| 97 | 31 | 29 | 2 |  | + |
| 98 | 26 | 29 | −3 |  |  |
| 101 | 31 | 29 | 2 |  | + |
| 104 | 34 | 29 | 5 | * | ++ |

*p < 0.05 and **p < 0.01

As shown in Table 2, 100 µM oxaliplatin inhibited a 60%-71% of DRG neurite outgrowth. Unexpectedly, it is found that neuroprotection was provided by Compounds 47, 97, 101, and 104. Notably, Compound 47 showed more than 7% of improvement (i.e., 47% outgrowth as compared to 40% in oxaliplatin treated cells).

Example 4: In Vivo Mouse Behavioral Models

Compound 47 was used in an in vivo mouse behavioral study for treating paclitaxel-induced neuropathy following a procedure described in Chen et al., Scientific Reports, 7, 45366, DOI: 10.1038/srep45366 (2017).

After housing adaptions, 7-weeks-old C57BL/6J female mice (weight range: 18-20 g) were treated as follows. Paclitaxel (4.5 mg/kg, Bristol-Myers Squibb, New York, New York), vehicle (saline), or Compound 47 (5, 10 or 20 mg/kg) was injected intraperitoneally on four alternative days (days 0, 2, 4, and 6). Two behavior tests were performed: (1) mechanical hyperalgesia was evaluated using a von Frey filament (Part #2390, IITC Inc., CA) and (2) thermal sensitivity was studied using a tail immersion assay (water temperature: 48-49° C.). See Chen et al., *Mol. Cancer. Ther.* 14, 2206-14 (2015). The baseline measurement of each behavior test was established prior to treatments. Five sessions were measured weekly.

The neuroprotective effects of Compound 47 in a mouse model was measured following a protocol with predetermined drug administration and behavioral tests. The basal levels of each behavioral assay were obtained prior to the treatment. In the first week, 4.5 mg/kg paclitaxel was injected intraperitoneally every other day and a vehicle or Compound 47 (5, 10 and 20 mg/kg) was administered by intraperitoneal injection one hour prior to paclitaxel treatment. After four courses of treatment, behavioral tests were done weekly.

A von Frey filament test was performed to detect allodynia. Pressure from touch was exerted until paw withdrawal. Thermal sensation was assessed using a tail immersion test by checking tail withdrawal latency.

Eight groups of mice were treated separately.

Mice in Groups 1, 2, and 3 were injected with Compound 47 in saline at doses of 5 mg/kg, 10 mg/kg, and 20 mg/kg, respectively. After an hour, the mice were injected with 4.5 mg/kg of paclitaxel.

As a comparative group, Group 4 mice were injected with saline and, after an hour, with 4.5 mg/kg of paclitaxel.

Mice in Control Group 5 were injected with saline twice instead of Compound 47 and paclitaxel.

In Control Groups 6, 7, and 8, mice were injected with Compound 47 at 5 mg/kg, 10 mg/kg, and 20 mg/kg, respectively, followed by injection of saline.

The results showed that Group 4 mice had a very low pain threshold due to paclitaxel toxicity. In Groups 1-3, Compound 47 provided protection even at the low dosage of 5 mg/kg. After administered Compound 47 at 10 mg/kg and 20 mg/kg, mice in both groups had a similar pain threshold as the control groups, demonstrating high efficacy of Compound 47 in protecting paclitaxel-induced neuropathy.

In the tail immersion assay, similar results were observed, indicating again the neuroprotective efficacy of Compound 47.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A compound of formula (I):

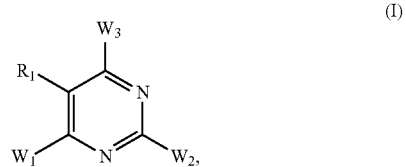

in which
R$_1$ is H, halo, nitro, cyano, amino, C$_{1-6}$ alkyl, C$_{1-6}$ alkoxy, C$_{3-10}$ cycloalkyl, C$_{1-10}$ heterocycloalkyl, aryl, or heteroaryl;
W$_1$ is C$_{1-10}$ heterocycloalkyl or NH—CH$_2$—Ar1-(CH$_2$)$_m$-A1;
one of W$_2$ and W$_3$ is NR$_a$R$_b$; and
the other of W$_2$ and W$_3$ is NH—CH$_2$—Ar2-(CH$_2$)$_n$-A2, wherein
each of Ar1 and Ar2, independently, is five-membered heteroaryl;
each of A1 and A2, independently, is H, OH, SH, CO$_2$R$_c$, PO$_3$R$_c$R$_d$, NH$_2$, benzylamino, isopropylamino, ethanolamino, carbamido, guanidinyl, C$_{1-6}$ alkoxy, C$_{3-10}$ cycloalkyl, C$_{3-10}$ cycloalkyloxy, C$_{1-10}$ heterocycloalkyl, C$_{1-10}$ heterocycloalkyloxy, aryl, aryloxy, heteroaryl, heteroaryloxy, or NCOR$_c$;
each of R$_a$ and R$_b$, independently, is H, C$_{1-6}$ alkyl, C$_{3-10}$ cycloalkyl, C$_{1-10}$ hetero-cycloalkyl, or R$_a$ and R$_b$, together with the nitrogen atom to which they are bonded, are C$_{1-10}$ heterocycloalkyl;
each of R$_c$ and R$_d$, independently, is H, C$_{1-6}$ alkyl, C$_{3-10}$ cycloalkyl, C$_{1-10}$ hetero-cycloalkyl, aryl, or heteroaryl;
each of C$_{1-6}$ alkyl, C$_{1-6}$ alkoxy, C$_{3-10}$ cycloalkyl, C$_{3-10}$ cycloalkyloxy, C$_{1-10}$ hetero-cycloalkyl, C$_{1-10}$ heterocycloalkyloxy, aryl, heteroaryl, aryloxy, heteroaryloxy, ethanolamino, benzylamino, and carbamido, is optionally substituted with hydroxyl, halo, nitro, cyano, amino, C$_{1-6}$ alkyl, arylalkyl, C$_{1-6}$ alkoxyl, C$_{1-6}$ carboxyalkyl, aryl, heteroaryl, PO$_3$R$_e$R$_f$, NCOR$_e$, NC(O)OR$_e$, C(O)OR$_e$, COR$_e$, (CH$_2$)$_x$—PO$_3$R$_e$R$_f$, (CH$_2$)$_x$—NCOR$_e$, or (CH$_2$)$_x$—C(O)OR$_e$;
each of R$_e$ and R$_f$, independently, is H, C$_{1-6}$ alkyl, C$_{3-10}$ cycloalkyl, C$_{1-10}$ hetero-cycloalkyl, aryl, or heteroaryl;
each of m and n, independently, is 0, 1, 2, 3, 4, or 5; and
x is 1, 2, 3, or 4.

2. The compound of claim 1, wherein R$_1$ is H and W$_1$ is morpholino.

3. The compound of claim 2, wherein W$_2$ is NH—CH$_2$—Ar2-(CH$_2$)$_n$-A2 and n is 2, 3, or 4.

4. The compound of claim 3, wherein W$_3$ is NR$_a$R$_b$; R$_a$ is H; and R$_b$ is six-membered heterocycloalkyl optionally substituted with hydroxyl, (CH$_2$)$_x$—PO$_3$R$_e$R$_f$, or (CH$_2$)$_x$NCOR$_e$, each of R$_e$ and R$_f$ independently, being H, C$_{1-6}$ alkyl, C$_{3-10}$ cycloalkyl, C$_{1-10}$ hetero-cycloalkyl, aryl, or heteroaryl and x being 2 or 3.

5. The compound of claim 1, wherein
R$_1$ is H;
W$_1$ is C$_{1-10}$ heterocycloalkyl or NH—CH$_2$—Ar1(CH$_2$)$_m$A1;

W$_2$ is NH—CH$_2$—Ar2-(CH$_2$)$_n$-A2;
W$_3$ is NR$_a$R$_b$;
each of A1 and A2, independently, is H, OH, C$_{1-6}$ alkyl, C$_{1-6}$ alkoxy, or NCOR$_c$;
R$_a$ is H or R$_a$ and R$_b$, together with the nitrogen atom to which they are bonded, are six-membered heterocycloalkyl;
R$_b$ is six-membered heterocycloalkyl or R$_b$ and R$_a$, together with the nitrogen atom to which they are bonded, are six-membered heterocycloalkyl;
R$_c$ is C$_{1-6}$ alkyl;
each of C$_{1-6}$ alkyl, C$_{1-6}$ alkoxy, and C$_{1-10}$ hetero-cycloalkyl, is optionally substituted with hydroxyl, NH$_2$, (CH$_2$)$_x$—PO$_3$R$_e$R$_f$, C(O)OR$_e$, or (CH$_2$)$_x$—NCOR$_e$;
each of R$_e$ and R$_f$, independently, is H, C$_{1-6}$ alkyl, C$_{3-10}$ cycloalkyl, C$_{1-10}$ hetero-cycloalkyl, aryl, or heteroaryl;
each of m and n is 2, 3, or 4; and x is 1, 2, 3, or 4.

6. The compound of claim 1, wherein W$_2$ is NH—CH$_2$—Ar2-(CH$_2$)$_n$-A2 and n is 2, 3, or 4.

7. The compound of claim 1, wherein W$_3$ is NR$_a$R$_b$; R$_a$ is H; and R$_b$ is six-membered heterocycloalkyl optionally substituted with hydroxyl, (CH$_2$)$_x$—PO$_3$R$_e$R$_f$ or (CH$_2$)$_x$—NCOR$_e$, each of R$_e$ and R$_f$, independently, being H, C$_{1-6}$ alkyl, C$_{3-10}$ cycloalkyl, C$_{1-10}$ hetero-cycloalkyl, aryl, or heteroaryl and x being 2 or 3.

8. The compound of claim 1, wherein R$_1$ is H; W$_1$ is morpholino; W$_2$ is NH—CH$_2$—Ar2-(CH$_2$)$_n$-A2, in which Ar2 is triazole, n is 2 or 3, and A2 is OH; and W$_3$ is NR$_a$R$_b$, in which R$_a$ is H and R$_b$ is a piperidine moiety optionally substituted with (CH$_2$)$_x$—PO$_3$R$_e$R$_f$, each of R$_e$ and R$_f$, independently, being H or C$_{1-6}$ alkyl and x being 2 or 3.

9. The compound of claim 1, wherein the compound is selected from the group consisting of Compounds 1-148 having the structures as shown below:

1

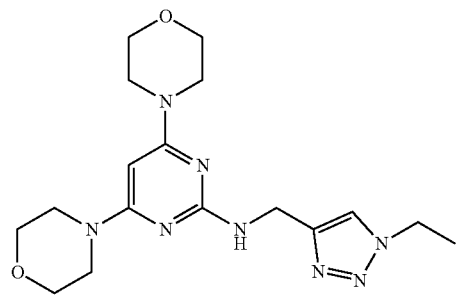

2

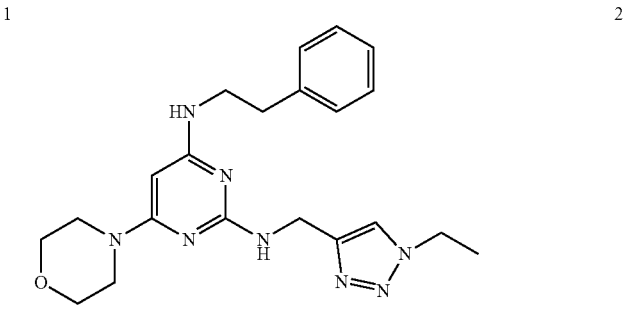

3

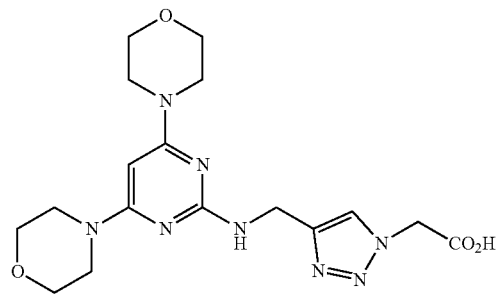

4

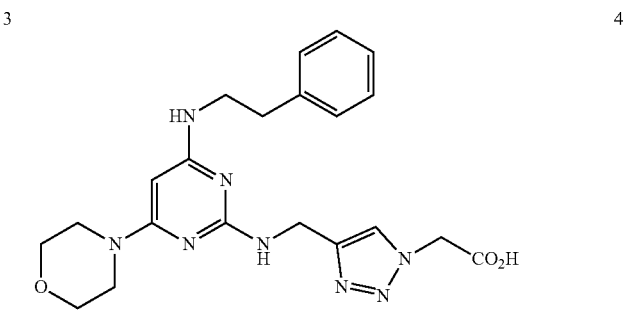

5

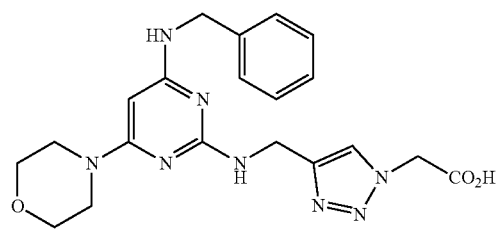

6

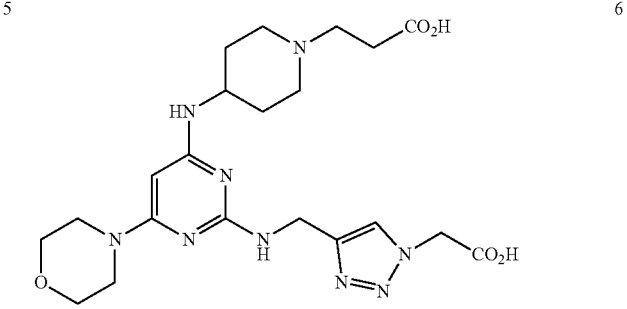

7

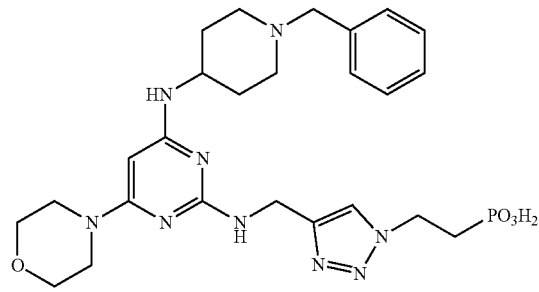

8

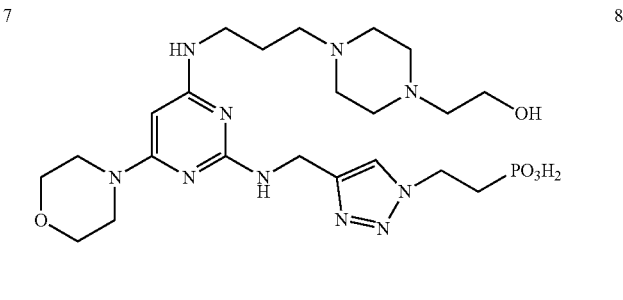

-continued
9
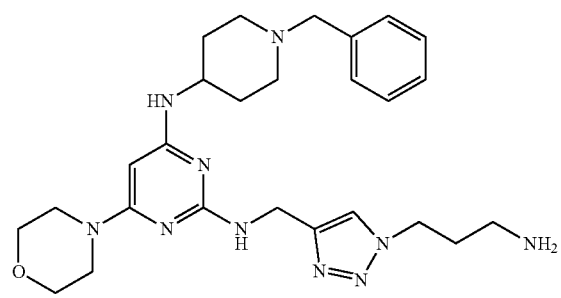
10
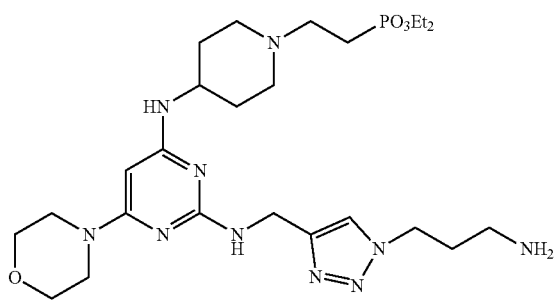
11
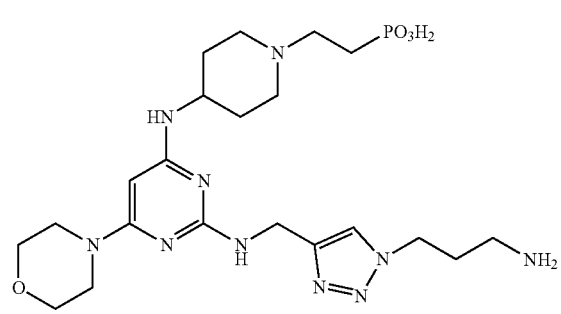
12
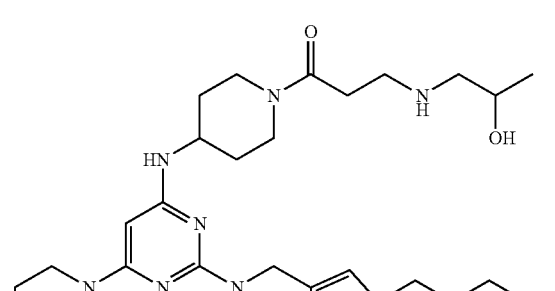
13
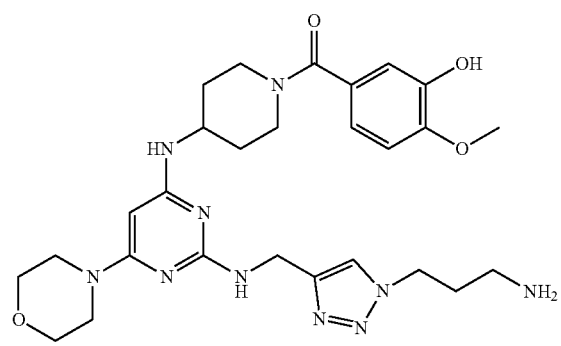
14
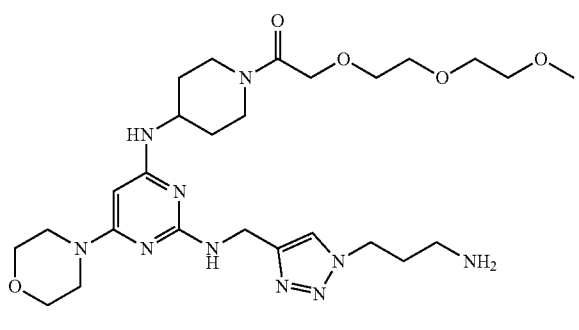
15
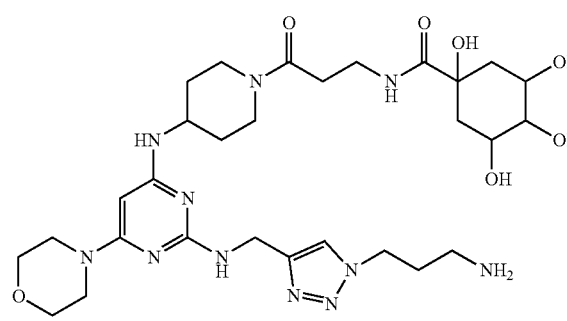
16
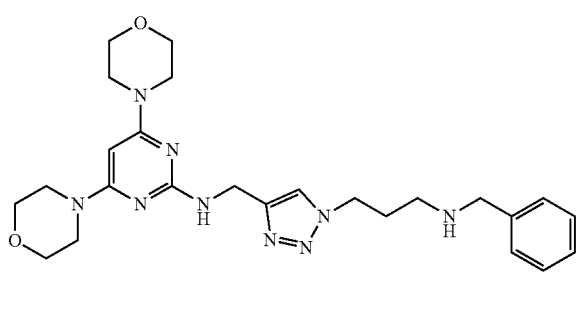
17
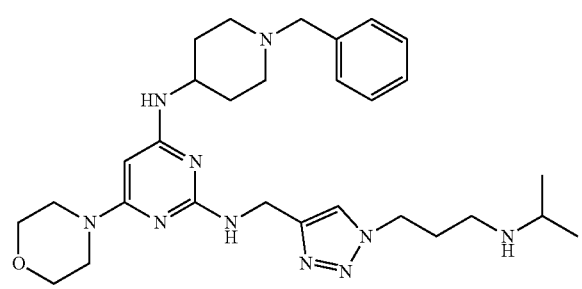
18
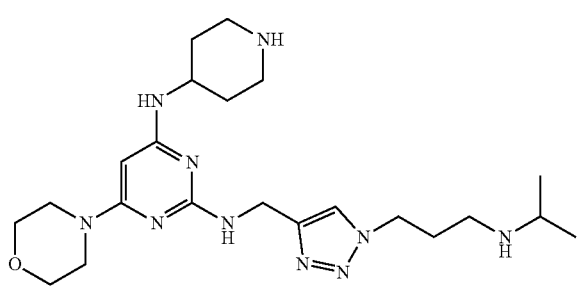

-continued
| 19 | 20 |
|---|---|
| 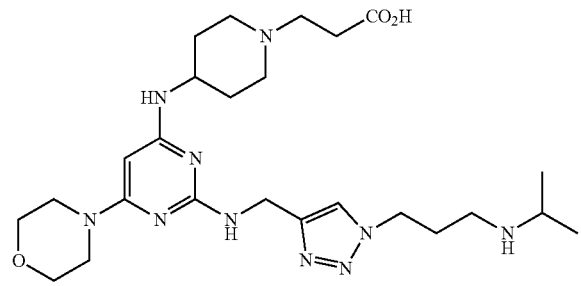 | 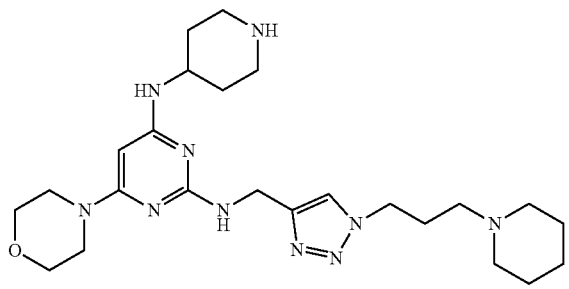 |
| 21 | 22 |
| 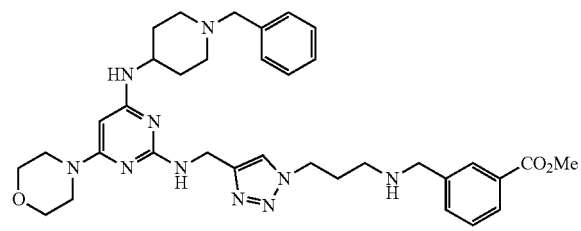 | 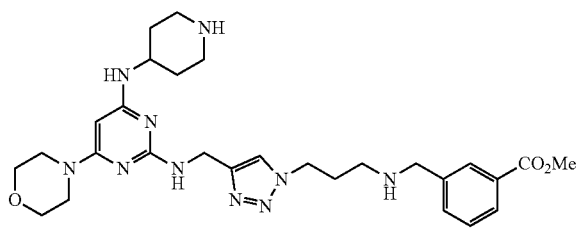 |
| 23 | 24 |
| 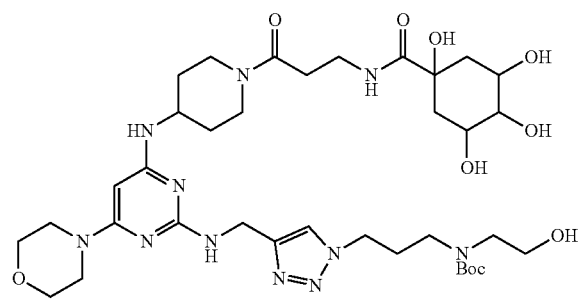 | 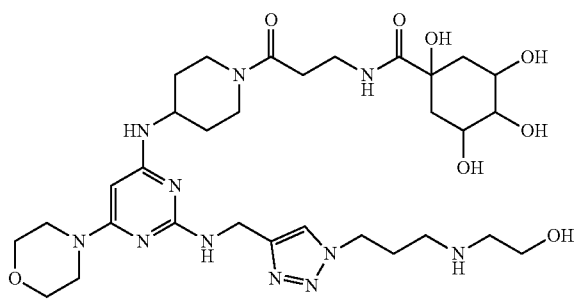 |
| 25 | 26 |
| 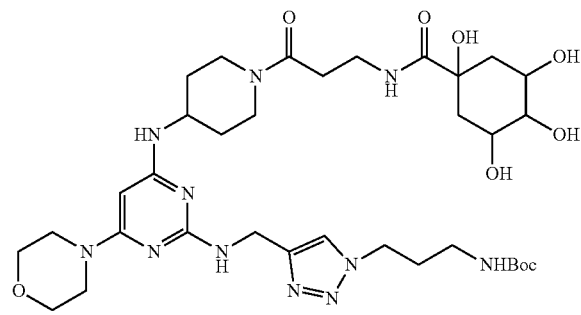 | 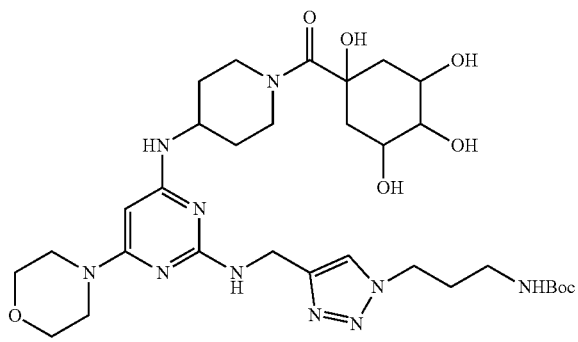 |
| 27 | 28 |
| 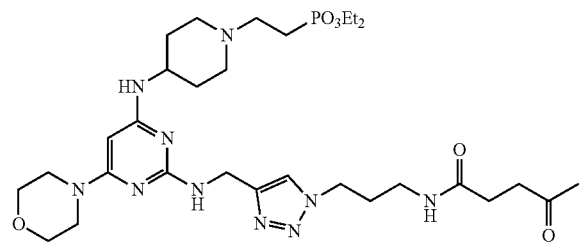 | 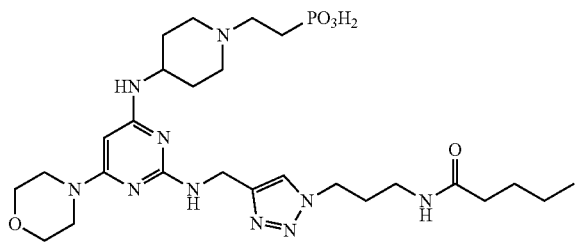 |

29
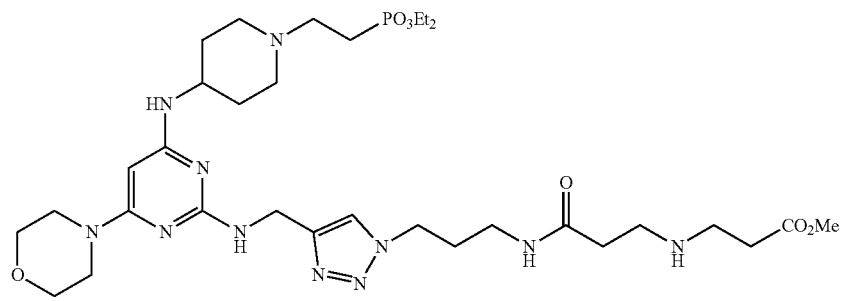
30
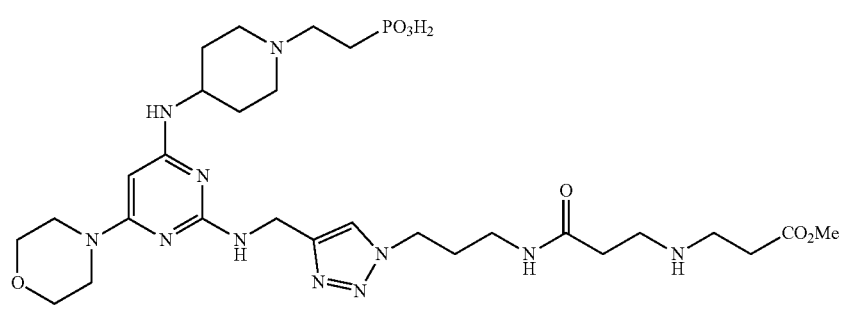
31
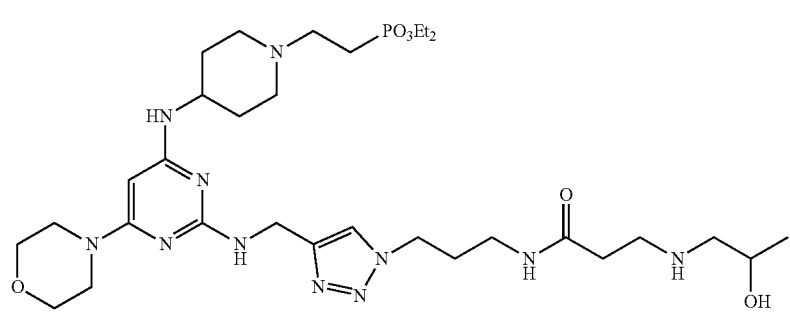
32
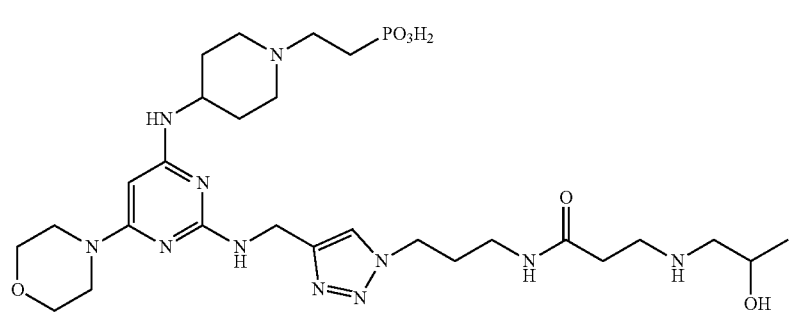
33
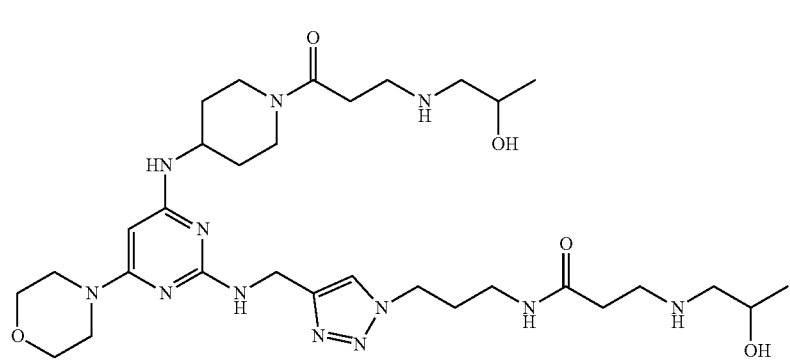

34
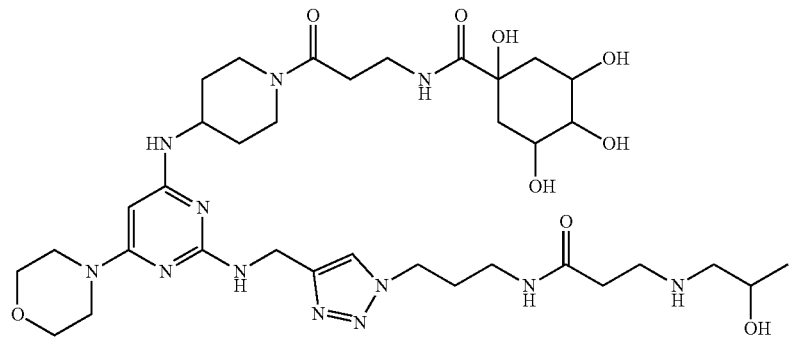
35
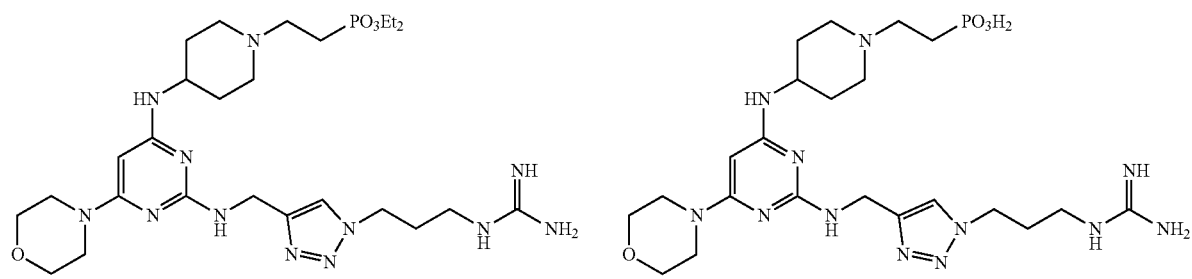
36
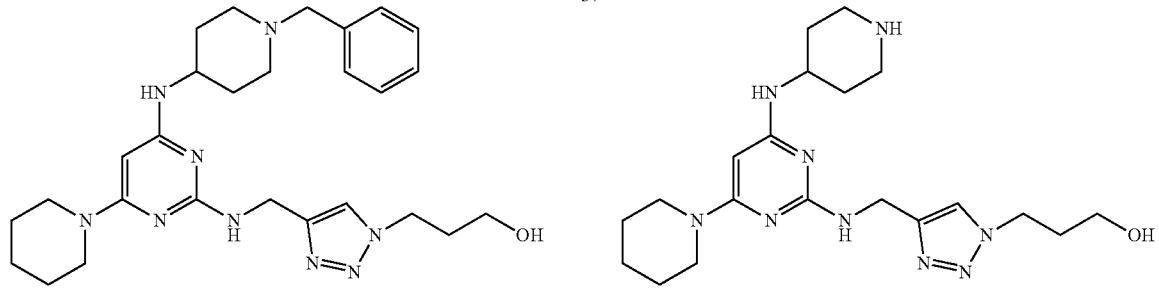
37 38
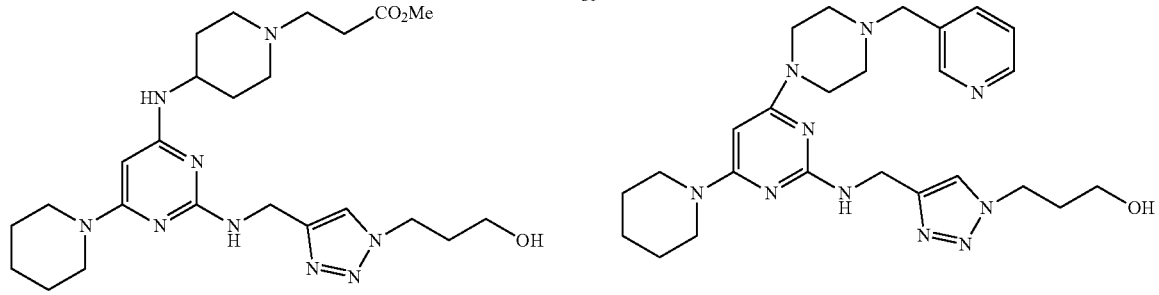
39 40
41 42
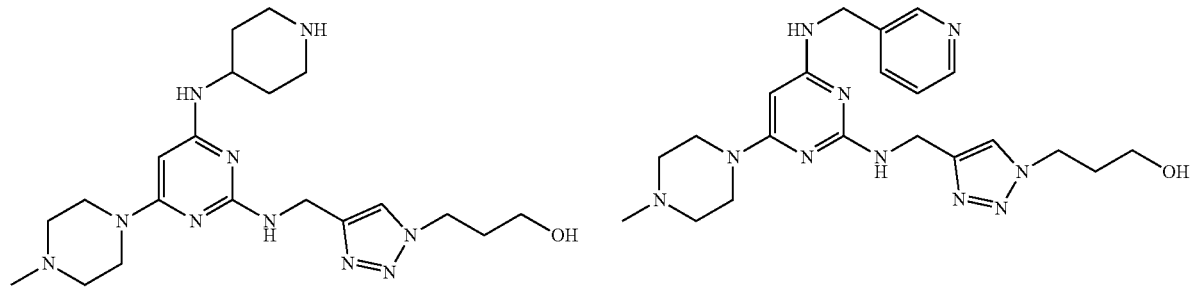

-continued
43
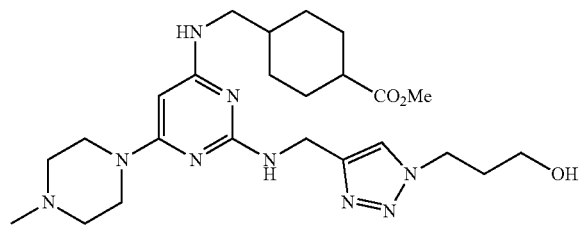
44
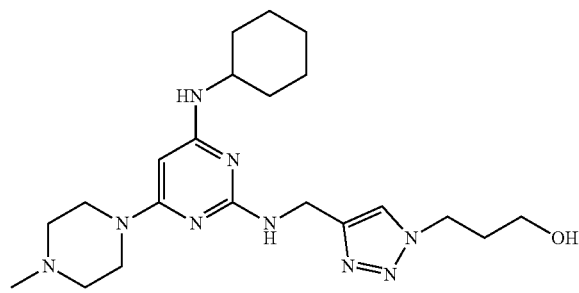
45
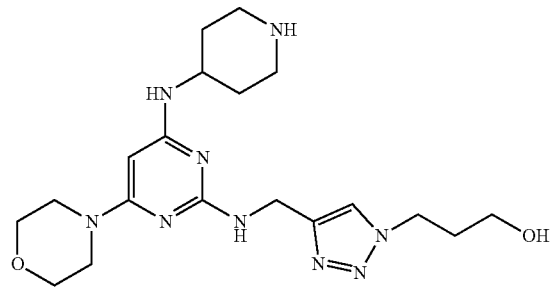
46
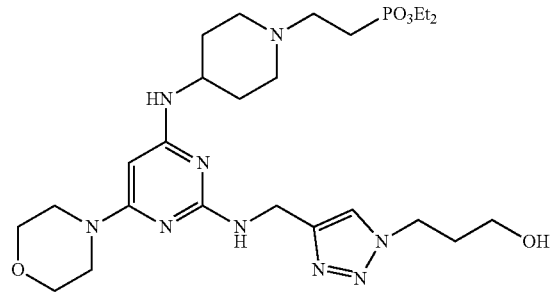
47
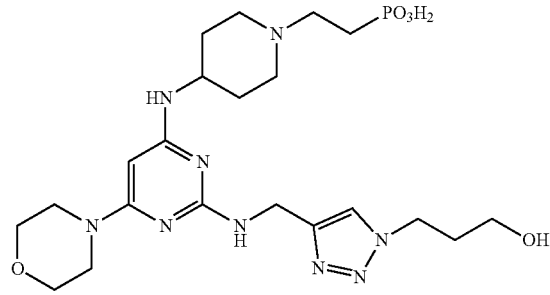
48
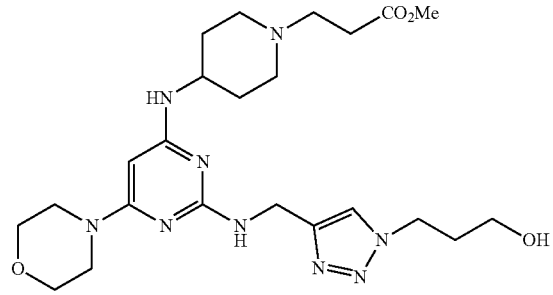
49
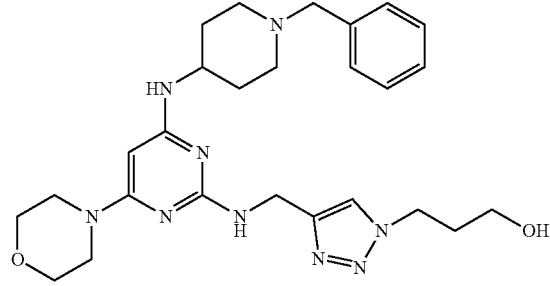
50
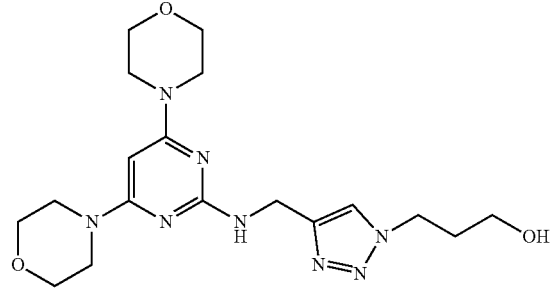
51
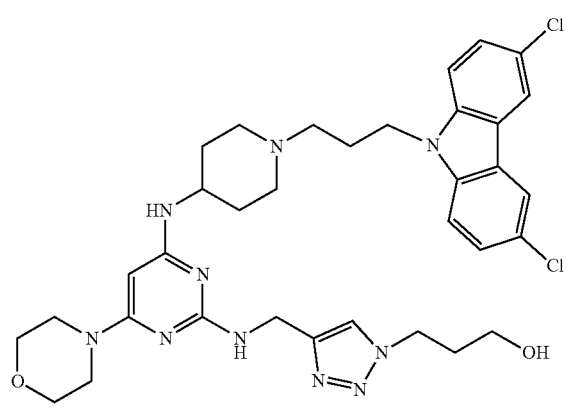
52
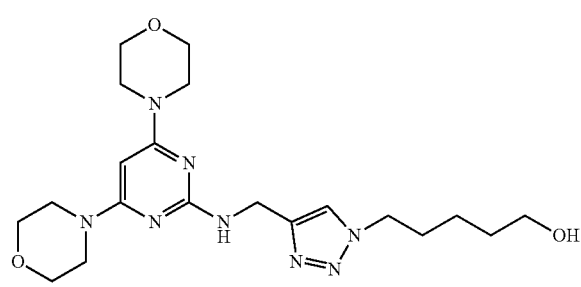

-continued
| 53 | 54 |
|---|---|
| 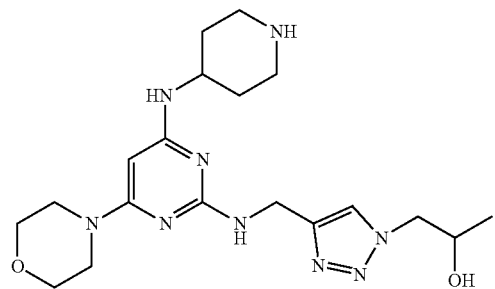 | 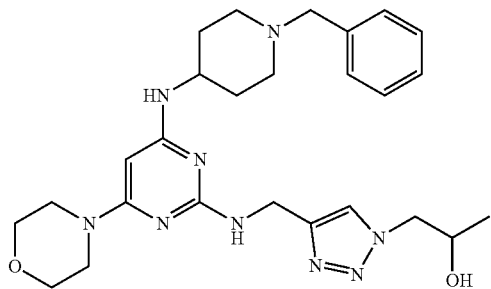 |
| 55 | 56 |
| 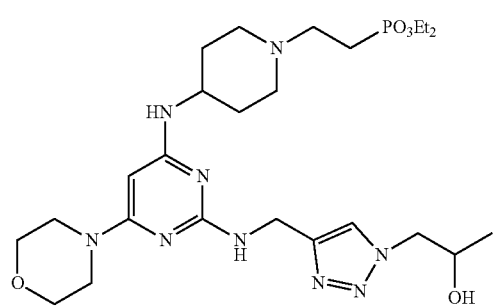 | 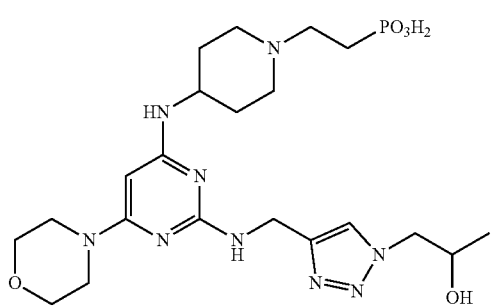 |
| 57 | 58 |
| 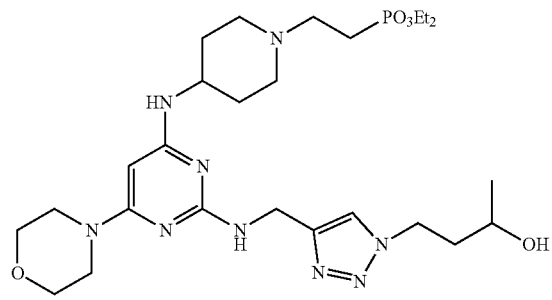 | 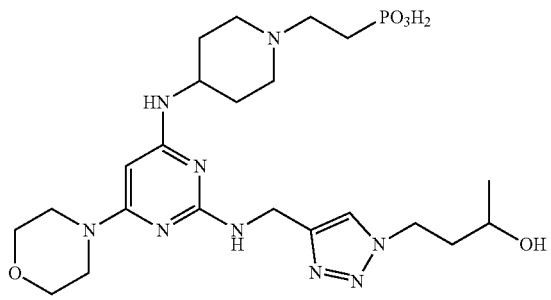 |
| 59 | 60 |
| 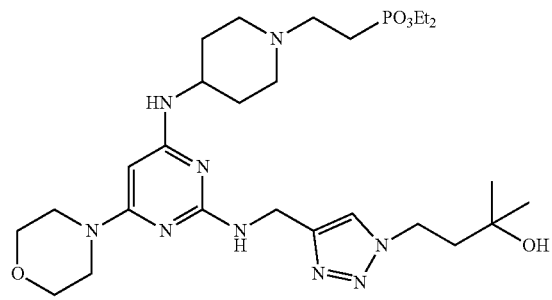 | 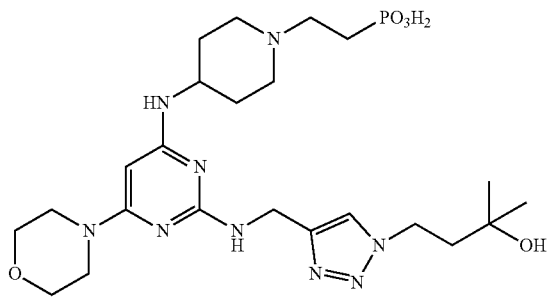 |
| 61 | 62 |
| 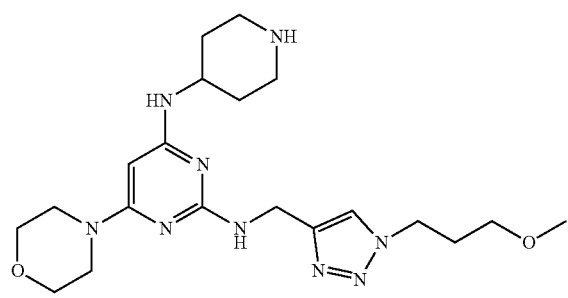 | 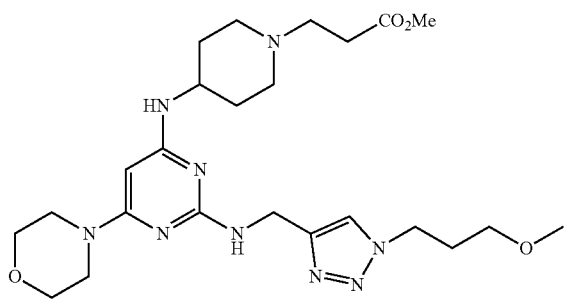 |

-continued
63
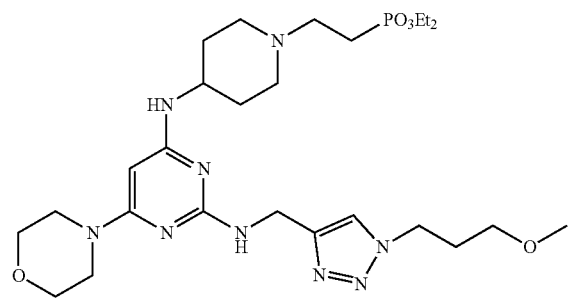
64
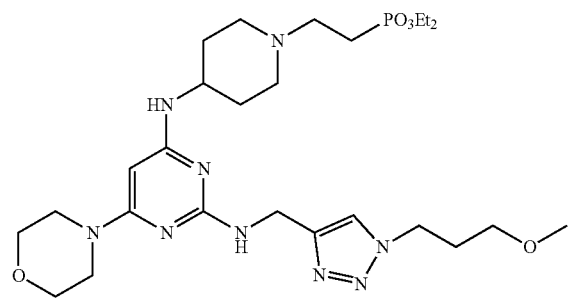
65
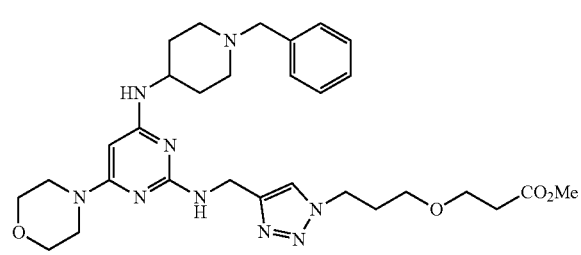
66
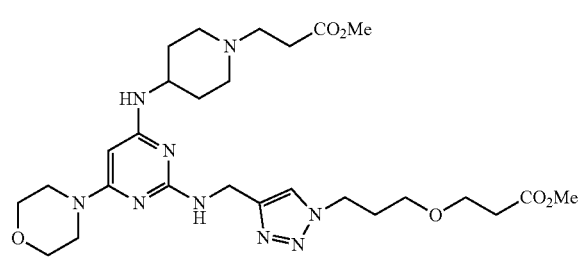
67
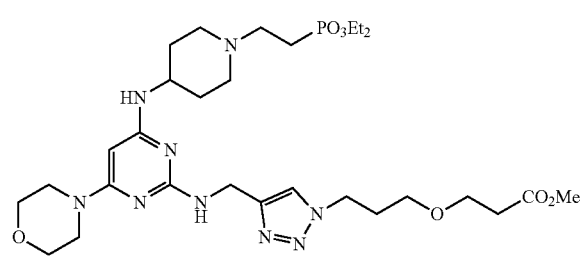
68
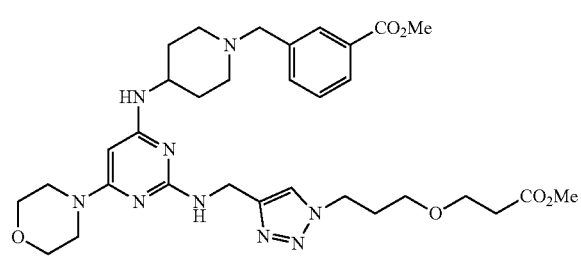
69
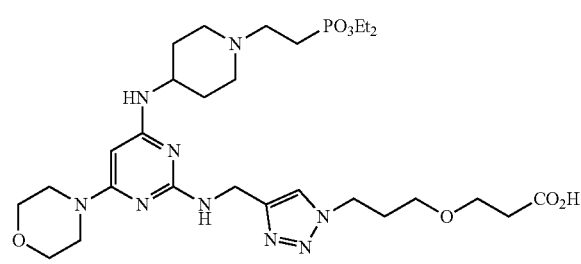
70
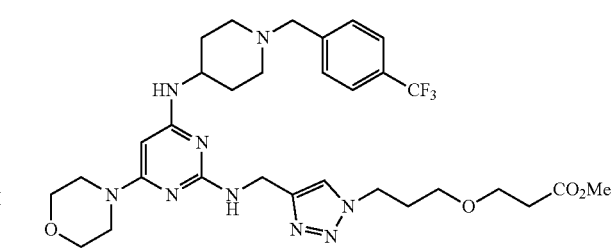
71
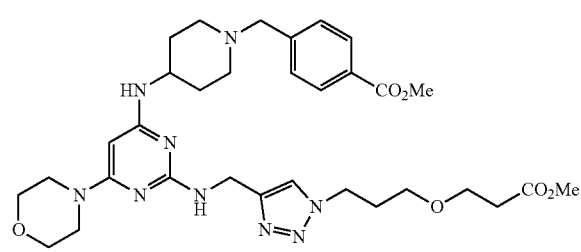
72
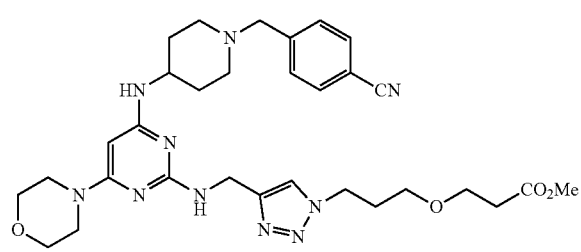

-continued
73
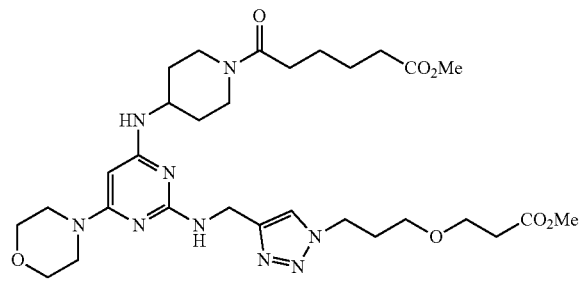
74
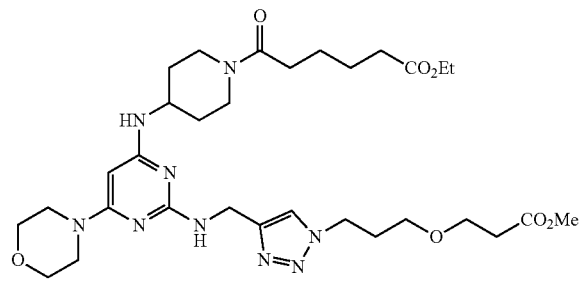
75
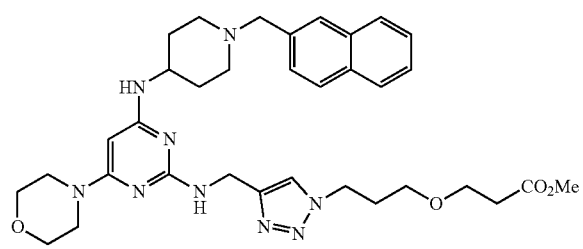
76
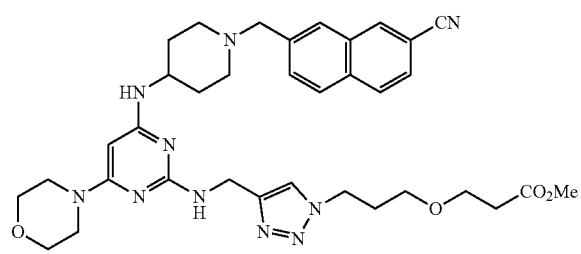
77
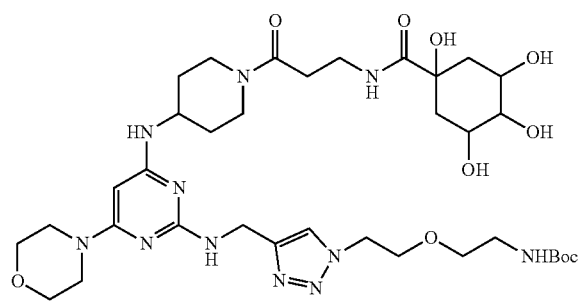
78
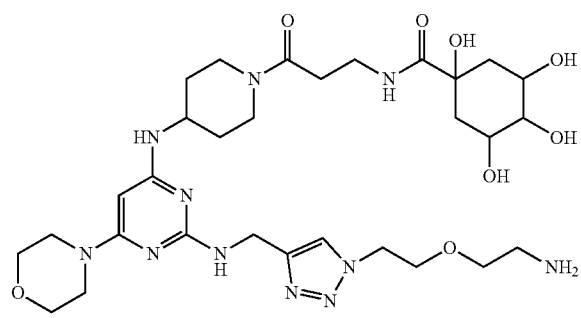
79
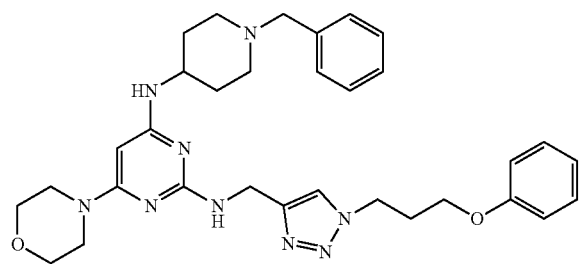
80
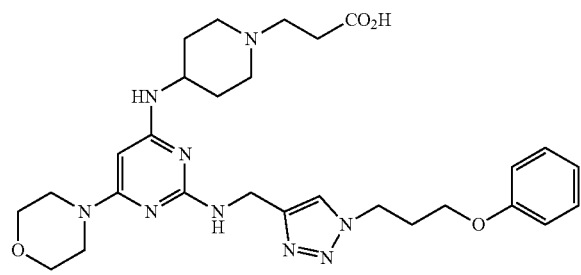
81
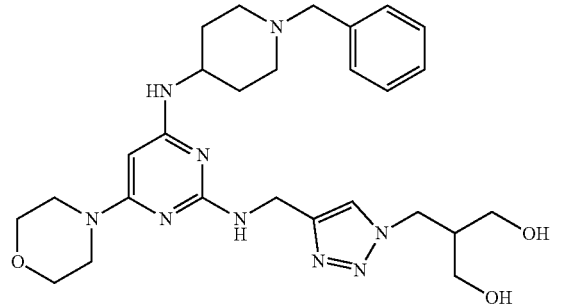
82
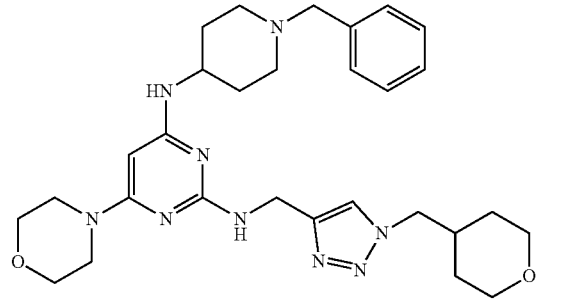

-continued
83
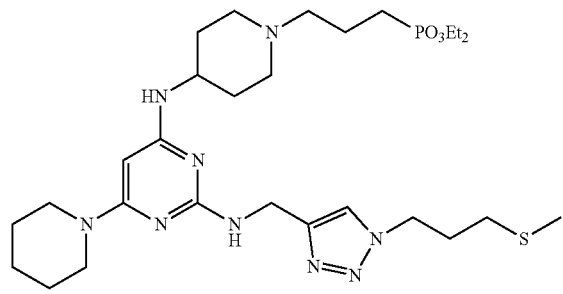
85
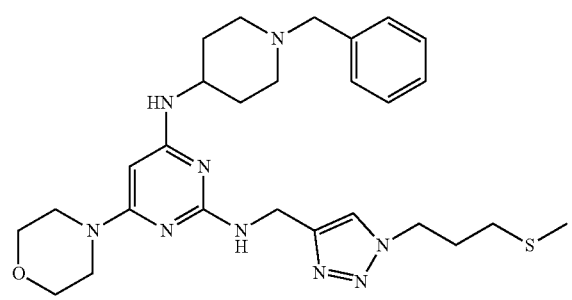
87
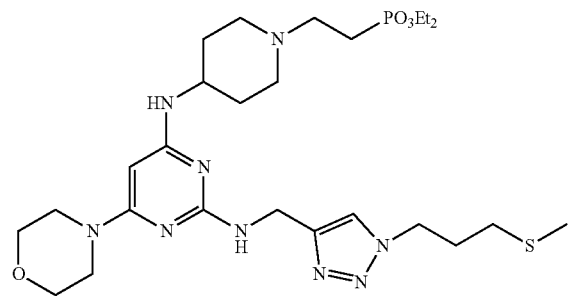
89
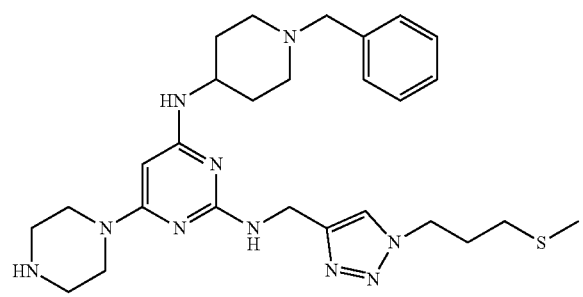
91
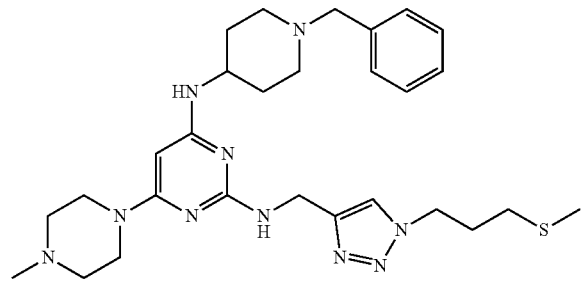
84
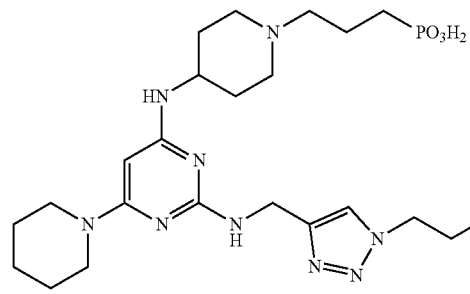
86
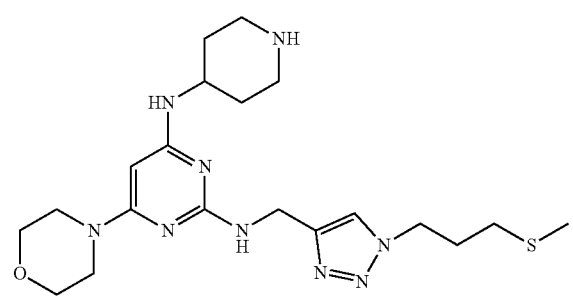
88
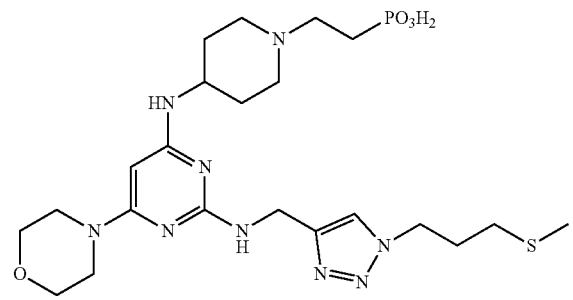
90
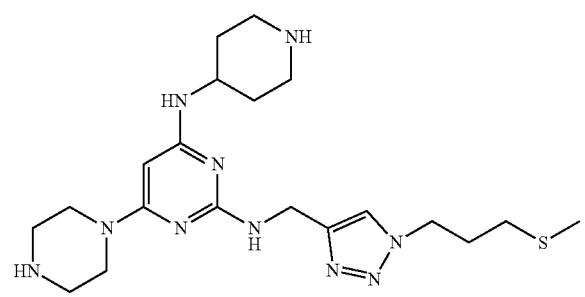
92
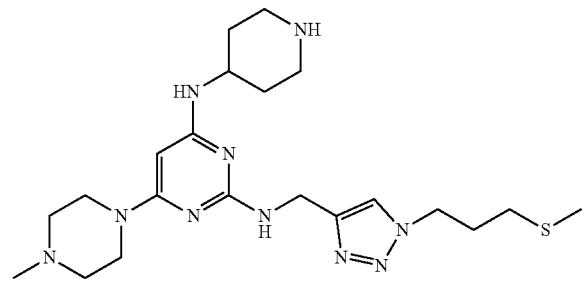

93
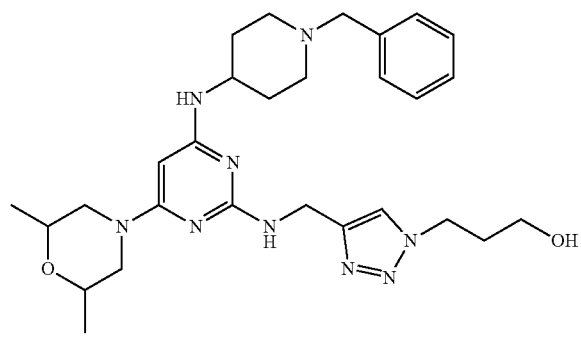
94
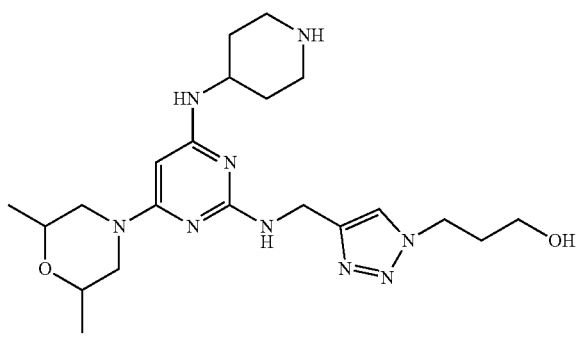
95
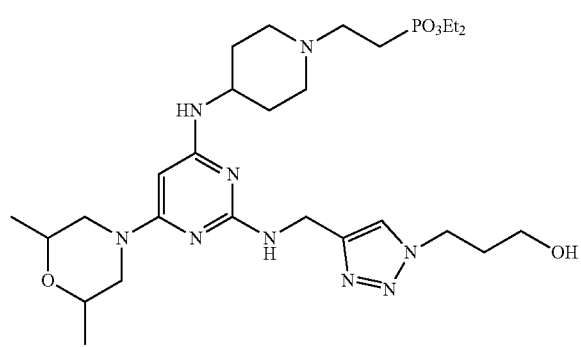
96
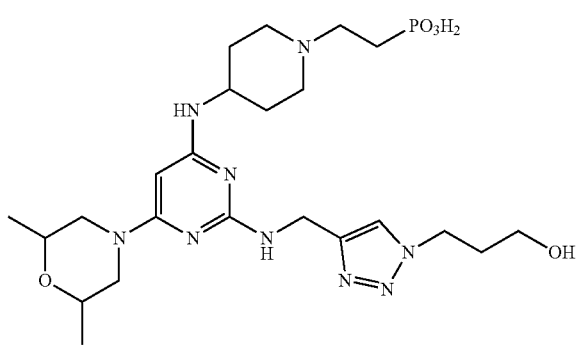
97
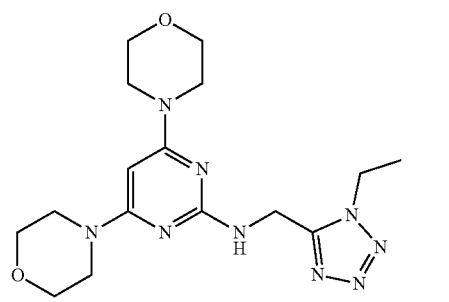
98
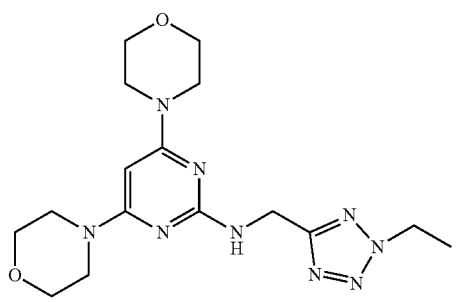
99
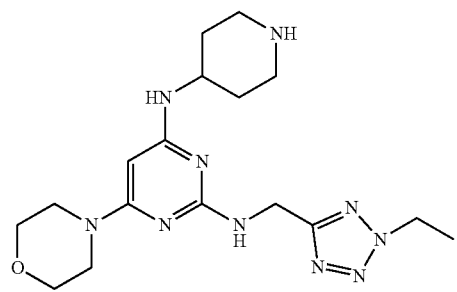
100
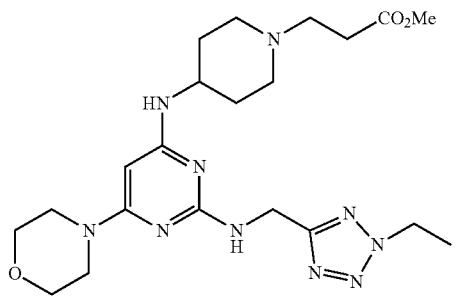
101
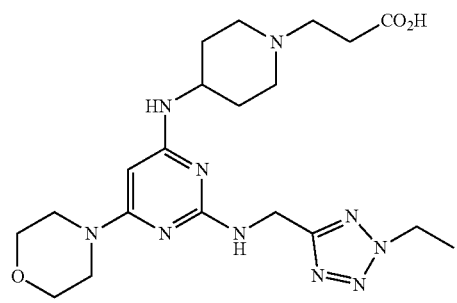
102
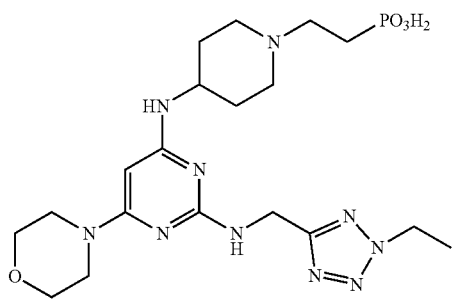

-continued
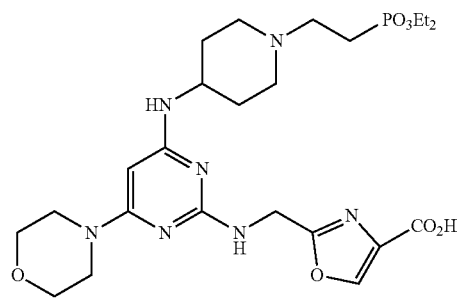
103
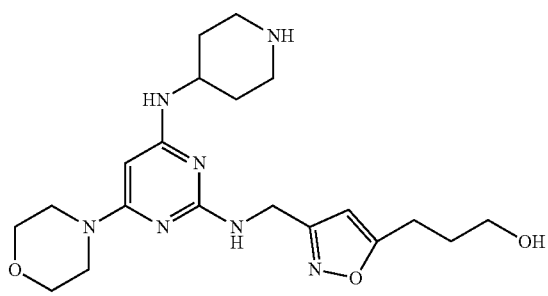
104
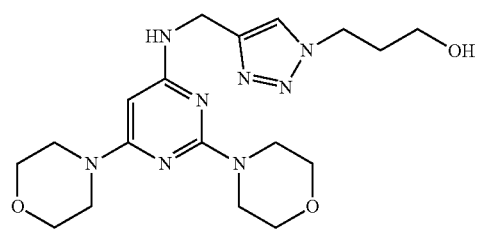
105
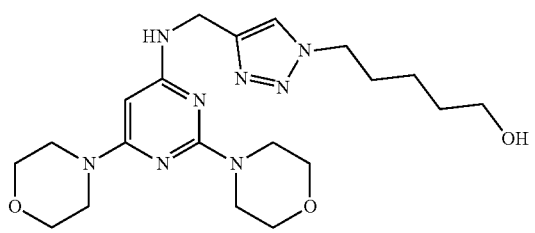
106
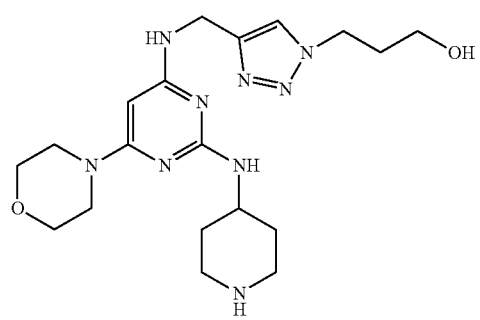
107
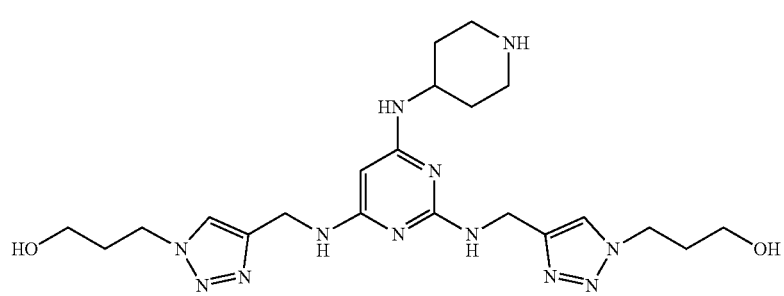
108
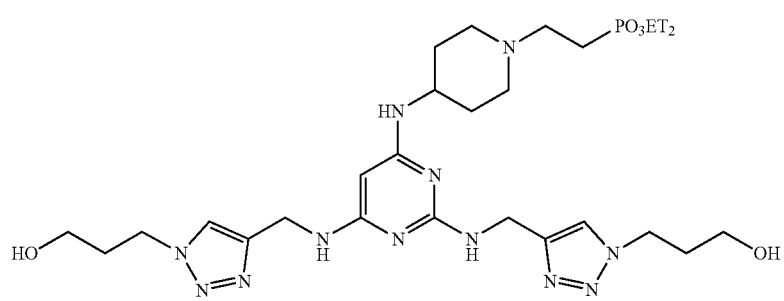
109

-continued
110
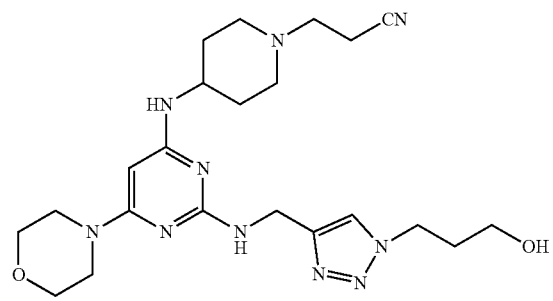
111
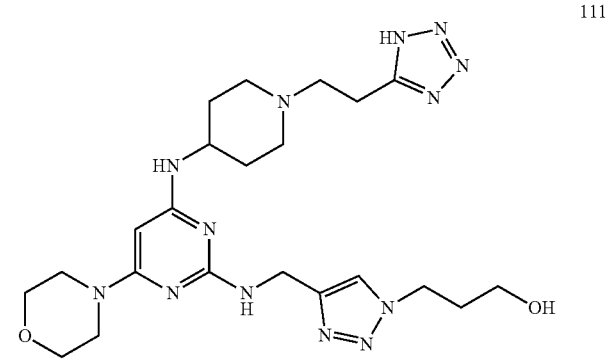
112 113
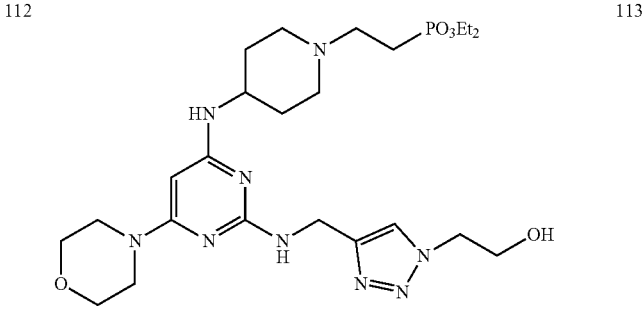
114 115
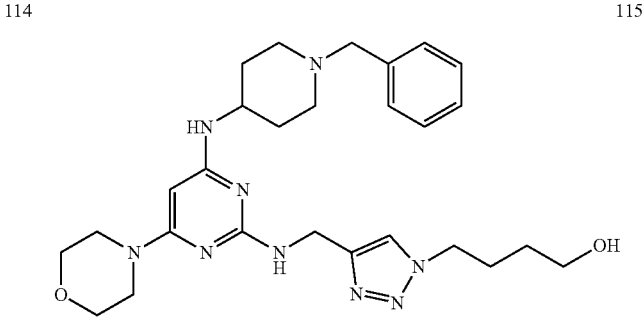
116 117
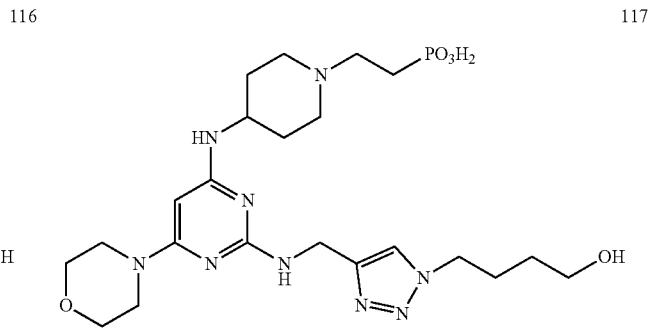
118 119
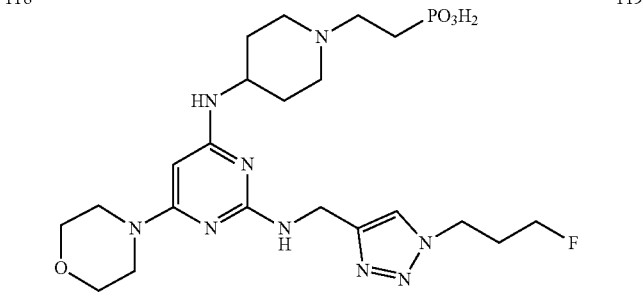

120
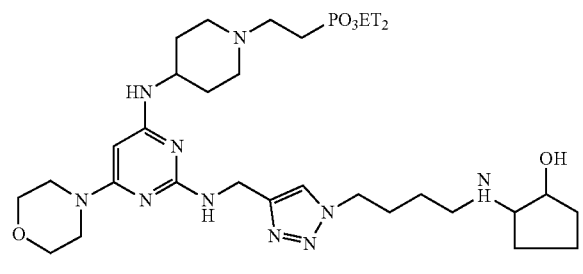
121
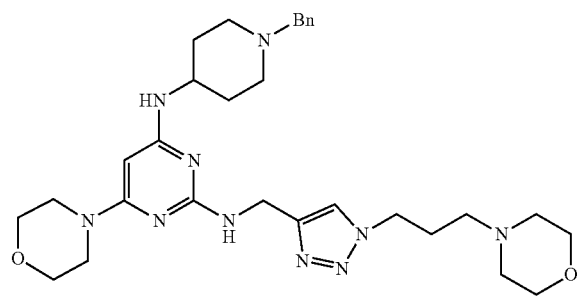
122
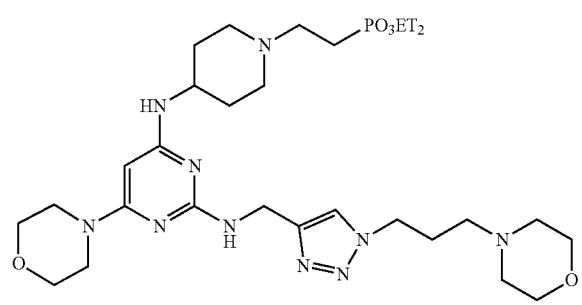
123
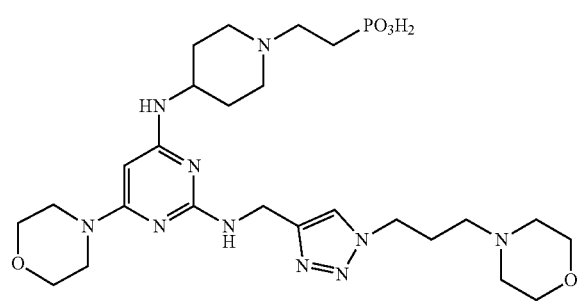
124
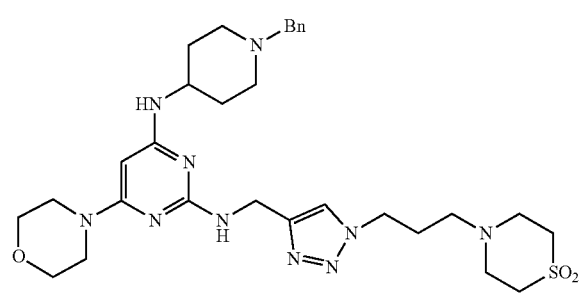
125
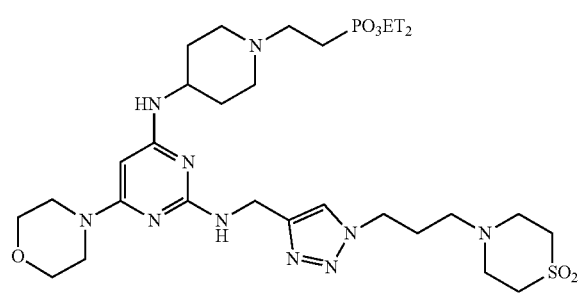
126
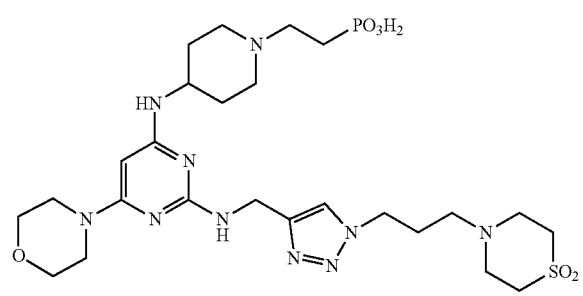
127
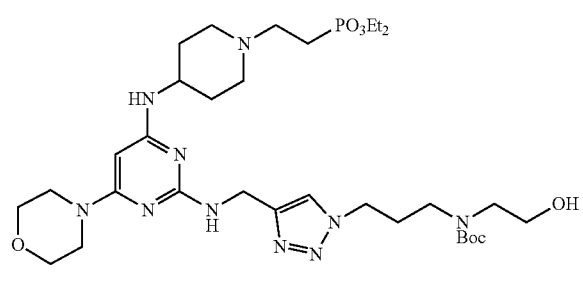
128
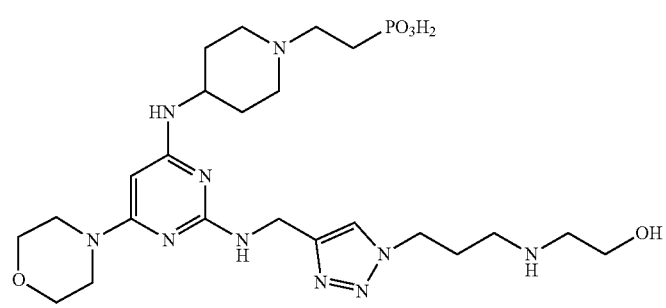

129
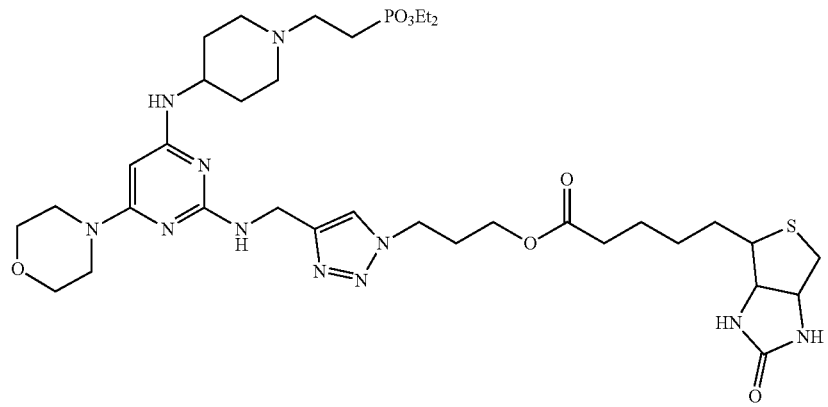
130
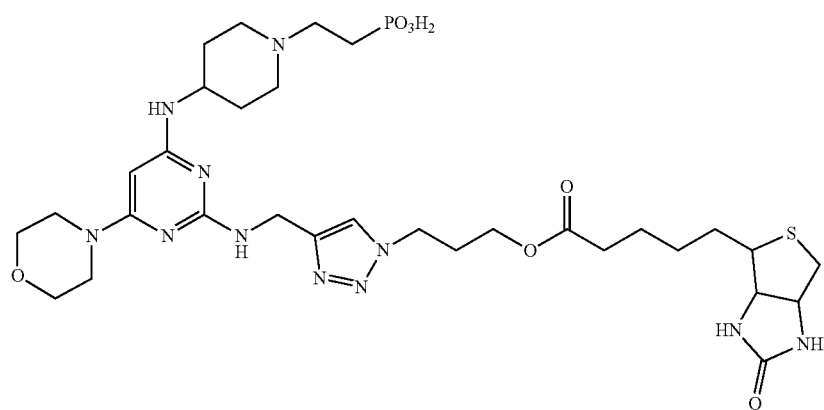
131 132
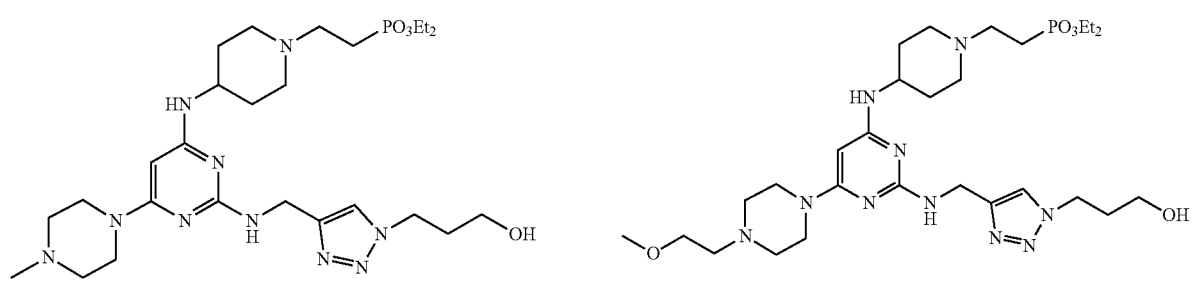
133 134
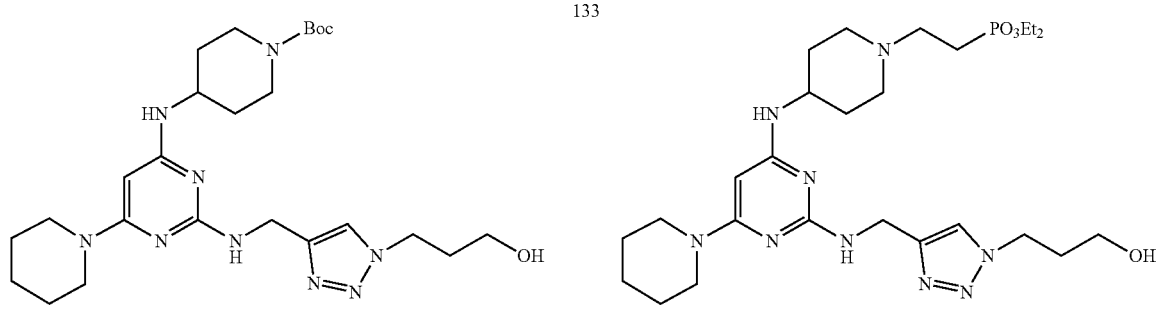

-continued
135
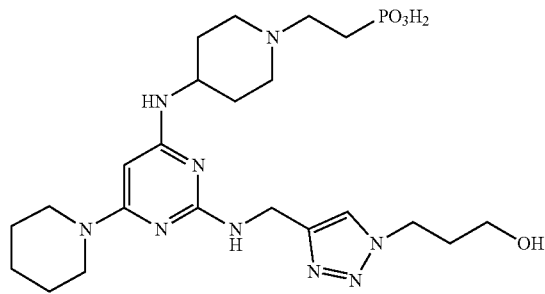
136
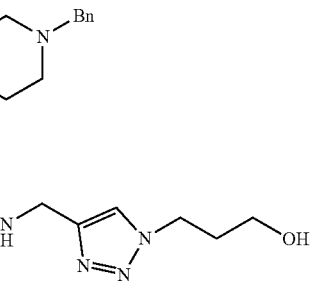
137
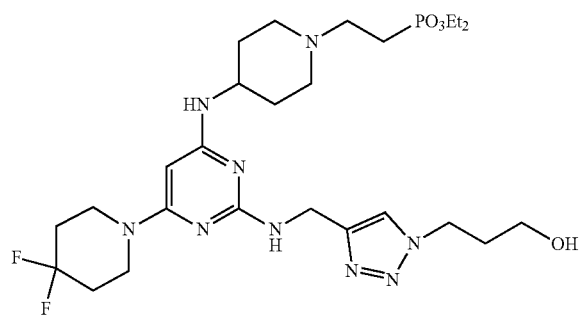
138
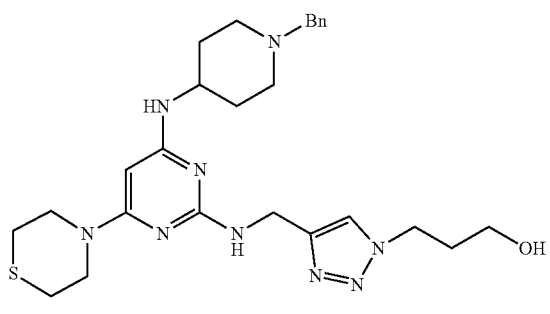
139
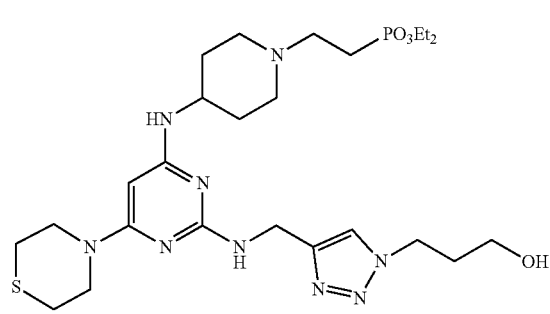
140
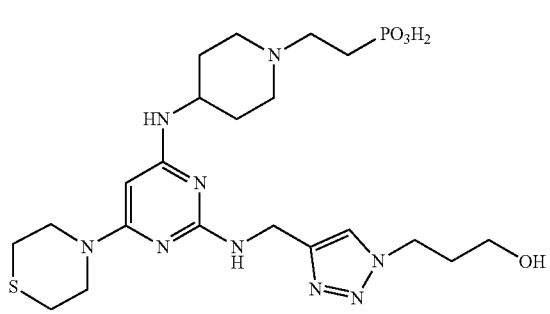
141
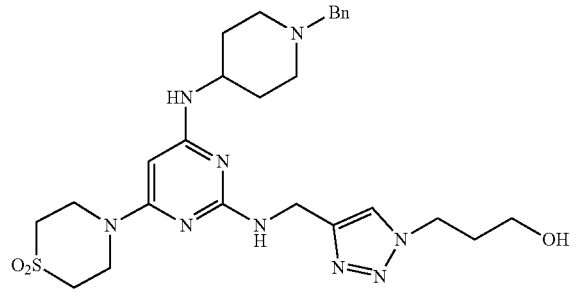
142
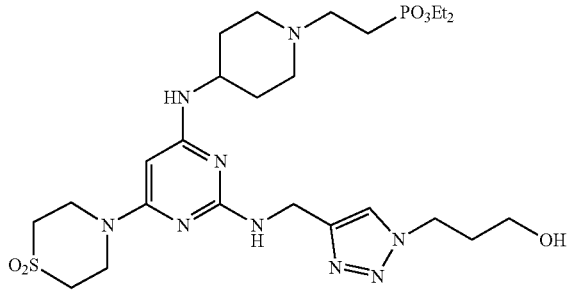
143
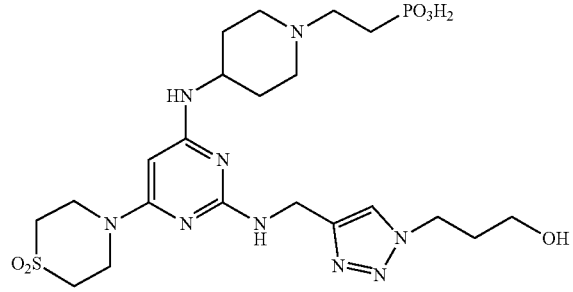
144
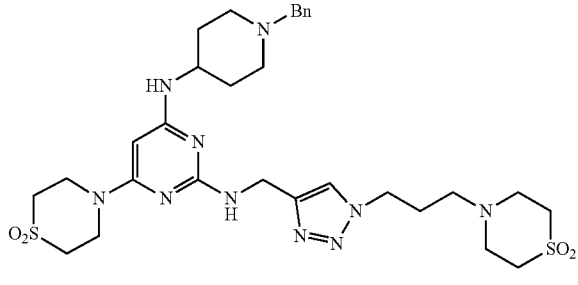

145

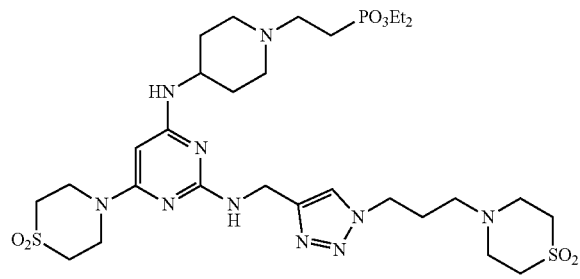

146

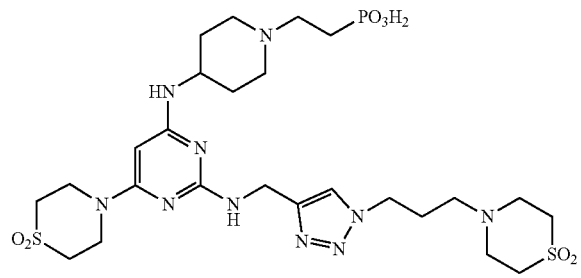

147

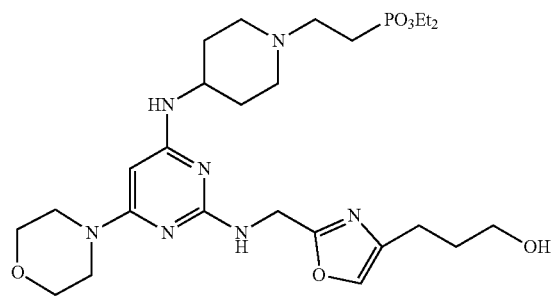

148

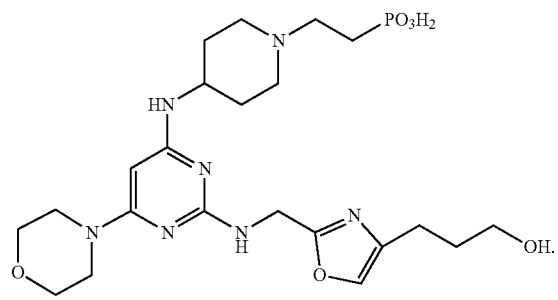

10. The compound of claim 9, wherein the compound is selected from the group consisting of Compounds 28, 46, 47, 58, 67, 69, 78, 97, 104, 109, 114, and 117.

11. The compound of claim 9, wherein the compound is Compound 47.

12. A method of treating chemotherapy-induced peripheral neuropathy, the method comprising administering to a subject in need thereof an effective amount of a compound of claim 1, wherein the chemotherapy-induced peripheral neuropathy is allodynia or thermal sensitivity.

13. The method of claim 12, further comprising administering to the subject an anticancer agent.

14. The method of claim 13, wherein the compound of claim 1 is administered prior to the administration of the anticancer agent.

15. The method of claim 13, wherein the anticancer agent is paclitaxel and oxaliplatin.

16. The method of claim 12, wherein the compound of claim 1 is selected from the group consisting of Compounds 28, 46, 47, 58, 67, 69, 78, 97, 104, 109, 114, and 117.

17. A pharmaceutical composition comprising a compound of claim 1 and a pharmaceutically acceptable carrier thereof.

18. The pharmaceutical composition of claim 17, wherein the compound of claim 1 is selected from the group consisting of Compounds 28, 46, 47, 58, 67, 69, 78, 97, 104, 109, 114, and 117.

19. The method of claim 12, wherein the chemotherapy-induced peripheral neuropathy is allodynia.

20. The method of claim 12, wherein the chemotherapy-induced peripheral neuropathy is thermal sensitivity.

* * * * *